US011643394B2

(12) United States Patent
Mallipattu et al.

(10) Patent No.: US 11,643,394 B2
(45) Date of Patent: May 9, 2023

(54) KRÜPPEL-LIKE FACTOR 15 (KLF15) SMALL MOLECULE AGONISTS IN KIDNEY DISEASE

(71) Applicants: United States Government as represented by the Department of Veterans Affairs, Washington, DC (US); Icahn School of Medicine at Mount Sinai, New York, NY (US); The Research Foundation for The State University of New York, Albany, NY (US)

(72) Inventors: Sandeep Mallipattu, St. James, NY (US); Bhaskar Das, West Nyack, NY (US)

(73) Assignees: Icahn School of Medicine at Mount Sinai, New York, NY (US); The United States Government as represented by the Department of Veterans Affairs, Washington, DC (US); The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 17/244,762

(22) Filed: Apr. 29, 2021

(65) Prior Publication Data
US 2021/0347734 A1 Nov. 11, 2021

Related U.S. Application Data

(60) Provisional application No. 63/018,247, filed on Apr. 30, 2020.

(51) Int. Cl.
*C07D 213/85* (2006.01)
*C07D 213/74* (2006.01)
*A61K 31/573* (2006.01)
*C07C 321/20* (2006.01)

(52) U.S. Cl.
CPC .......... *C07D 213/85* (2013.01); *A61K 31/573* (2013.01); *C07C 321/20* (2013.01); *C07D 213/74* (2013.01)

(58) Field of Classification Search
None
See application file for complete search history.

(56) References Cited

U.S. PATENT DOCUMENTS

| | | | |
|---|---|---|---|
| 5,814,646 A | 9/1998 | Heinz et al. | |
| 2005/0222200 A1 | 10/2005 | Kelly | |

FOREIGN PATENT DOCUMENTS

| | | | | |
|---|---|---|---|---|
| WO | WO 2005046683 A1 | 5/2005 | | |
| WO | WO 2005/113511 | * 12/2005 | ........... C07D 231/50 |
| WO | WO 2005/113511 A1 | 12/2005 | | |
| WO | WO 2006/018662 A2 | 2/2006 | | |
| WO | WO 2007056221 A2 | 5/2007 | | |
| WO | WO 2009/126691 | 10/2009 | | |
| WO | WO 2011088045 A1 | 7/2011 | | |
| WO | WO 2017/192841 A1 | 11/2017 | | |
| WO | WO 2018/057805 A1 | 3/2018 | | |

OTHER PUBLICATIONS

Cas RN 195452-55-2 (entered into STN on Aug. 16, 1997) (Year: 1997).*
U.S. Appl. No. 63/018,247, filed Apr. 30, 2020, Mallipattu, Sandeep.
PCT, PCT/US2021/029986 (WO 2021/22637), Apr. 29, 2021, Mallipattu, Sandeep.
Ahmed M, Gaffen SL. IL-17 inhibits adipogenesis in part via C/EBPalpha, PPARgamma and Kruppel-like factors. Cytokine. 2013;61(3):898-905.
Ahn JM, Boyle NA, MacDonald MT, Janda KD. Peptidomimetics and peptide backbone modifications. Mini Rev Med Chem. 2002; 2(5):463-73.
Ashburner M, Ball CA, Blake JA, Botstein D, Butler H, Cherry JM, Davis AP, Dolinski K, Dwight SS, Eppig JT. Gene Ontology: tool for the unification of biology. Nature genetics. 2000; 25(1):25-9.
Barisoni L, Bruggeman LA, Mundel P, D'Agati VD, Klotman PE. HIV-1 induces renal epithelial dedifferentiation in a transgenic model of HIV-associated nephropathy. Kidney Int. 2000; 58(1):173-81.
Barisoni L. Podocyte biology in segmental sclerosis and progressive glomerular injury. Adv Chronic Kidney Dis. 2012; 19(2):76-83.
Bialkowska AB, Yang VW, Mallipattu SK. Kruppel-like factors in mammalian stem cells and development. Development (2017). doi: 10.1242/dev.145441.
Bonomi R, Mukhopadhyay U, Shavrin A, Yeh HH, Majhi A, Dewage SW, Najjar A, Lu X, Cisneros GA, Tong WP, Alauddin MM, Liu RS, Mangner TJ, Turkman N, Gelovani JG. Novel Histone Deacetylase Class IIa Selective Substrate Radiotracers for PET Imaging of Epigenetic Regulation in the Brain. PLoS One. 2015; 10(8):e0133512.
Bonomi RE, Laws M, Popov V, Kamal S, Potukutchi S, Shavrin A, Lu X, Turkman N, Liu RS, Mangner T, Gelovani JG. A Novel Substrate Radiotracer for Molecular Imaging of SIRT2 Expression and Activity with Positron Emission Tomography. Mol Imaging Biol. 2018; 20(4):594-604.

(Continued)

*Primary Examiner* — Craig D Ricci
(74) *Attorney, Agent, or Firm* — Ballard Spahr LLP

(57) ABSTRACT

The present disclosure is concerned with small molecule modulators of KLF15 signaling useful for treating various disorders such as, for example, kidney disease (e.g., chronic kidney disease), heart disease, obesity, or a neurodegenerative disorder (e.g., amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD)). This abstract is intended as a scanning tool for purposes of searching in the particular art and is not intended to be limiting of the present invention.

9 Claims, 35 Drawing Sheets

(56) References Cited

OTHER PUBLICATIONS

Chen E, Tan C, Kou Y, Duan Q, Wang Z, Meirelles G, Clark N, Ma'ayan A. Enrichr: interactive and collaborative HTML5 gene list enrichment analysis tool. BMC Bioinformatics. 2013; 14(1):128.

Clark NR, Hu KS, Feldmann AS, Kou Y, Chen EY, Duan Q, Ma'ayan A. The characteristic direction: a geometrical approach to identify differentially expressed genes. BMC Bioinformatics. 2014; 15:79.

Czerniecki SM, Cruz NM, Harder JL, Menon R, Annis J, Otto EA, Gulieva RE, Islas LV, Kim YK, Tran LM, Martins TJ, Pippin JW, Fu H, Kretzler M, Shankland SJ, Himmelfarb J, Moon RT, Paragas N, Freedman BS. High-Throughput Screening Enhances Kidney Organoid Differentiation from Human Pluripotent Stem Cells and Enables Automated Multidimensional Phenotyping. Cell Stem Cell. 2018; 22(6):929-40 e4.

Daina A, Michielin 0, Zoete V. SwissADME: a free web tool to evaluate pharmacokinetics, drug-likeness and medicinal chemistry friendliness of small molecules. Sci Rep. 2017; 7:42717.

Das BC, Madhukumar AV, Anguiano J, Mani S. Design, synthesis and biological evaluation of 2H-benzo[b][1,4] oxazine derivatives as hypoxia targeted compounds for cancer therapeutics. Bioorg Med Chem Lett. 2009; 19(15):4204-6.

Das BC, Mahalingam SM, Evans T. Design and synthesis of novel pinacolylboronate containing combretastatin 'antimitotic agent' analogues. Tetrahedron Lett. 2009; 50(25):3031-4.

Das BC, McCartin K, Liu TC, Peterson RT, Evans T. A forward chemical screen in zebrafish identifies a retinoic acid derivative with receptor specificity. PLoS One. 2010; 5(4):e10004.

Das BC, Smith ME, Kalpana GV. Design, synthesis of novel peptidomimetic derivatives of 4-HPR for rhabdoid tumors. Bioorg Med Chem Lett. 2008; 18(14):4177-80.

Das BC, Thapa P, Karki R, Schinke C, Das S, Kambhampati S, Banerjee SK, Van Veldhuizen P, Verma A, Weiss LM, Evans T. Boron chemicals in diagnosis and therapeutics. Future Med Chem. 2013; 5(6):653-76.

Estrada CC, Paladugu P, Guo Y, Pace J, Revelo MP, Salant DJ, Shankland SJ, D'Agati VD, Mehrotra A, Cardona S, Bialkowska AB, Yang VW, He JC, Mallipattu SK. Kruppel-like factor 4 is a negative regulator of STAT3-induced glomerular epithelial cell proliferation. JCI Insight. 2018; 3(12).

Ghali JR, O'Sullivan KM, Eggenhuizen PJ, Holdsworth SR, Kitching AR. Interleukin-17RA Promotes Humoral Responses and Glomerular Injury in Experimental Rapidly Progressive Glomerulonephritis. Nephron. 2017; 135(3):207-23.

Grundy SM, Benjamin IJ, Burke GL, Chait A, Eckel RH, Howard BV, Mitch W, Smith SC, Jr., Sowers JR. Diabetes and cardiovascular disease: a statement for healthcare professionals from the American Heart Association. Circulation. 1999; 100(10):1134-46.

Gu X, Mallipattu SK, Guo Y, Revelo MP, Pace J, Miller T, Gao X, Jain MK, Bialkowska AB, Yang VW, He JC, Mei C. The loss of Kruppel-like factor 15 in Foxdl+ stromal cells exacerbates kidney fibrosis. Kidney Int. 2017.

Guo Y, Pace J, Li Z, Ma'ayan A, Wang Z, Revelo MP, Chen E, Gu X, Attalah A, Yang Y, Estrada C, Yang VW, He JC, Mallipattu SK. Podocyte-Specific Induction of Kruppel-Like Factor 15 Restores Differentiation Markers and Attenuates Kidney Injury in Proteinuric Kidney Disease. J Am Soc Nephrol. 2018; 29(10):2529-45.

Hagmann H, Brinkkoetter PT. Experimental Models to Study Podocyte Biology: Stock-Taking the Toolbox of Glomerular Research. Front Pediatr. 2018; 6:193.

Kanehisa M, Goto S. KEGG: kyoto encyclopedia of genes and genomes. Nucleic Acids Res. 2000; 28(1):27-30.

Kapp TG, Rechenmacher F, Neubauer S, Maltsev OV, Cavalcanti-Adam EA, Zarka R, Reuning U, Notni J, Wester HJ, Mas-Moruno C, Spatz J, Geiger B, Kessler H. A Comprehensive Evaluation of the Activity and Selectivity Profile of Ligands for RGD-binding Integrins. Sci Rep. 2017; 7:39805.

Koh KH, Cao Y, Mangos S, Tardi NJ, Dande RR, Lee HW, Samelko B, Altintas MM, Schmitz VP, Lee H, Mukherjee K, Peev V, Cimbaluk DJ, Reiser J, Hahm E. Nonimmune cell-derived ICOS ligand functions as a renoprotective alphavbeta3 integrin-selective antagonist. J Clin Invest. 2019; 129(4):1713-26.

Kuleshov MV, Jones MR, Rouillard AD, Fernandez NF, Duan Q, Wang Z, Koplev S, Jenkins SL, Jagodnik KM, Lachmann A, McDermott MG, Monteiro CD, Gundersen GW, Ma'ayan A. Enrichr: a comprehensive gene set enrichment analysis web server 2016 update. Nucleic Acids Res. 2016; 44(W1):W90-7.

Lachmann A, Torre D, Keenan AB, Jagodnik KM, Lee HJ, Wang L, Silverstein MC, Ma'ayan A. Massive mining of publicly available RNA-seq data from human and mouse. Nature communications. 2018; 9(1):1366.

Lee HW, Khan SQ, Faridi MH, Wei C, Tardi NJ, Altintas MM, Elshabrawy HA, Mangos S, Quick KL, Sever S, Reiser J, Gupta V. A Podocyte-Based Automated Screening Assay Identifies Protective Small Molecules. J Am Soc Nephrol. 2015; 26(11):2741-52.

Lovering F, Bikker J, Humblet C. Escape from flatland: increasing saturation as an approach to improving clinical success. J Med Chem. 2009; 52(21):6752-6.

Mallipattu SK, Guo Y, Revelo MP, Roa-Pena L, Miller T, Ling J, Shankland SJ, Bialkowska AB, Ly V, Estrada C, Jain MK, Lu Y, Ma'ayan A, Mehrotra A, Yacoub R, Nord EP, Woroniecki RP, Yang VW, He JC. Kruppel-Like Factor 15 Mediates Glucocorticoid-Induced Restoration of Podocyte Differentiation Markers. J Am Soc Nephrol. 2017; 28(1):166-84.

Mallipattu SK, Horne SJ, D'Agati V, Narla G, Liu R, Frohman MA, Dickman K, Chen EY, Ma'ayan A, Bialkowska AB, Ghaleb AM, Nandan MO, Jain MK, Daehn I, Chuang PY, Yang VW, He JC. Kruppel-like factor 6 regulates mitochondrial function in the kidney. J Clin Invest. 2015; 125(3):1347-61.

Mallipattu SK, Liu R, Zheng F, Nada G, Ma'ayan A, Dikman S, Jain MK, Saleem M, D'Agati V, Klotman P, Chuang PY, He JC. Kruppel-Like factor 15 (KLF15) is a key regulator of podocyte differentiation. J Biol Chem. 2012.

Mallipattu SK, Estrada CC, He JC. The critical role of Kruppel-like factors in kidney disease. American journal of physiology Renal physiology (2016).

Mao Q, Wang L, Goodison S, Sun Y. Dimensionality Reduction Via Graph Structure Learning. Proceedings of the 21th ACM SIGKDD International Conference on Knowledge Discovery and Data Mining; Sydney, NSW, Australia. 2783309: ACM; 2015. p. 765-74.

McCarren P, Springer C, Whitehead L. An investigation into pharmaceutically relevant mutagenicity data and the influence on Ames predictive potential. J Cheminform. 2011; 3:51.

Meyrier A. Mechanisms of disease: focal segmental glomerulosclerosis. Nature clinical practice Nephrology. 2005; 1(1):44-54.

Mould AP, Craig SE, Byron SK, Humphries MJ, Jowitt TA. Disruption of integrin-fibronectin complexes by allosteric but not ligand-mimetic inhibitors. Biochem J. 2014; 464(3):301-13.

Muller PY, Milton MN. The determination and interpretation of the therapeutic index in drug development. Nat Rev Drug Discov. 2012; 11(10):751-61.

Naik, et al. (2018) "Synthesis and Evaluation of a new [18]F-Labeled Radiotracer for Studying the $GABA_B$ Receptor in the Mouse Brain," ACS Chemical Neuroscience, 9, pp. 1453-1461.

Neuhoff S, Artursson P, Zamora I, Ungell AL. Impact of extracellular protein binding on passive and active drug transport across Caco-2 cells. Pharm Res. 2006; 23(2):350-9.

Noack C, Haupt LP, Zimmermann WH, Streckfuss-Bomeke K, Zelarayan LC. Generation of a KLF15 homozygous knockout human embryonic stem cell line using paired CRISPR/Cas9n, and human cardiomyocytes derivation. Stem Cell Res. 2017; 23:127-31.

Ohse T, Vaughan MR, Kopp JB, Krofft RD, Marshall CB, Chang AM, Hudkins KL, Alpers CE, Pippin JW, Shankland SJ. De novo expression of podocyte protein in parietal epithelial cells during experimental glomerular disease. Am J Physiol Renal Physiol. 2010; 298(3):F702-11.

Onakpoya IJ, Heneghan CJ, Aronson JK. Post-marketing withdrawal of 462 medicinal products because of adverse drug reactions: a systematic review of the world literature. BMC Med. 2016; 14:10.

Pearson R, Fleetwood J, Eaton S, Crossley M, Bao S. Kruppel-like transcription factors: a functional family. Int J Biochem Cell Biol. 2008; 40(10):1996-2001.

(56) References Cited

OTHER PUBLICATIONS

Pico AR, Kelder T, Van Iersel MP, Hanspers K, Conklin BR, Evelo C. WikiPathways: pathway editing for the people. PLoS Biol. 2008; 6(7):e184.

Ponticelli C, Locatelli F. Glucocorticoids in the Treatment of Glomerular Diseases: Pitfalls and Pearls. Clin J Am Soc Nephrol. 2018; 13(5):815-22.

Ramani K, Pawaria S, Maers K, Huppler AR, Gaffen SL, Biswas PS. An essential role of interleukin-17 receptor signaling in the development of autoimmune glomerulonephritis. J Leukoc Biol. 2014; 96(3):463-72.

Rane MJ, Zhao Y, Cai L. Kruppel-like factors (KLFs) in renal physiology and disease. EBioMedicine. 2019; 40:743-50.

Reiser J, Mundel P. Danger signaling by glomerular podocytes defines a novel function of inducible B7-1 in the pathogenesis of nephrotic syndrome. Journal of the American Society of Nephrology : JASN. 2004; 15(9):2246-8.

Reiser J, von Gersdorff G, Loos M, Oh J, Asanuma K, Giardino L, Rastaldi MP, Calvaresi N, Watanabe H, Schwarz K, Faul C, Kretzler M, Davidson A, Sugimoto H, Kalluri R, Sharpe AH, Kreidberg JA, Mundel P. Induction of B7-1 in podocytes is associated with nephrotic syndrome. J Clin Invest. 2004; 113(10):1390-7.

Sai, et al. (2017) "Radiolabeling and Initial Biological Evaluation of [F]KBM-1 for imaging RAR-Receptors in Neuroblastoma," Bioorg Med Chem Lett. 27(6) pp. 1425-1427.

Scarfe L, Schock-Kusch D, Ressel L, Murray P, Wilm B, de Caestecker M. Transdermal Measurement of Glomerular Filtration Rate in Mice. J Vis Exp. 2018(140).

Schinke C, Goel S, Bhagat TD, Zhou L, Mo Y, Gallagher R, Kabalka GW, Platanias LC, Verma A, Das B. Design and synthesis of novel derivatives of all-trans retinoic acid demonstrate the combined importance of acid moiety and conjugated double bonds in its binding to PML-RAR-alpha oncogene in acute promyelocytic leukemia. Leuk Lymphoma. 2010; 51(6):1108-14.

Torban E, Braun F, Wanner N, Takano T, Goodyer PR, Lennon R, Ronco P, Cybulsky AV, Huber TB. From podocyte biology to novel cures for glomerular disease. Kidney Int. 2019; 96(4):850-61.

VA/DoD Clinical Practice Guideline: Management of Chronic Kidney Disease in Primary Care. 2014.

Van Husen M, Kemper MJ. New therapies in steroid-sensitive and steroid-resistant idiopathic nephrotic syndrome. Pediatr Nephrol. 2011; 26(6):881-92.

Waldman M, Crew RJ, Valeri A, Busch J, Stokes B, Markowitz G, D'Agati V, Appel G. Adult minimal-change disease: clinical characteristics, treatment, and outcomes. Clin J Am Soc Nephrol. 2007; 2(3):445-53.

Walsky RL, Boldt SE. In vitro cytochrome P450 inhibition and induction. Curr Drug Metab. 2008; 9(9):928-39.

Wang L, Lin W, Chen J. Kruppel-like Factor 15: A Potential Therapeutic Target For Kidney Disease. Int J Biol Sci. 2019; 15(9):1955-61.

Wannamethee SG, Shaper AG, Perry IJ. Serum creatinine concentration and risk of cardiovascular disease: a possible marker for increased risk of stroke. Stroke. 1997; 28(3):557-63.

Yang S, Wang Y, Mei K, Zhang S, Sun X, Ren F, Liu S, Yang Z, Wang X, Qin Z, Chang Z. Tumor necrosis factor receptor 2 (TNFR2).interleukin-17 receptor D (IL-17RD) heteromerization reveals a novel mechanism for NF-kappaB activation. J Biol Chem. 2015; 290(2):861-71.

Zappia L, Phipson B, Oshiack A. Exploring the single-cell RNA-seq analysis landscape with the scRNA-tools database. PLOS Computational Biology. 2018; 14(6):e1006245.

Zhang B, Liu C, Qian W, Han Y, Li X, Deng J. Structure of the unigue SEFIR domain from human interleukin 17 receptor A reveals a composite ligand-binding site containing a conserved alpha-helix for Actl binding and IL-17 signaling. Acta Crystallogr D Biol Crystallogr. 2014; 70(Pt 5):1476-83.

Zhang J, Pippin JW, Liu ZH, Shankland SJ. Podocyte repopulation by renal progenitor cells following glucocorticoids treatment in experimental FSGS. Am J Physiol Renal Physiol. 2013; 304(11):F1375-89.

Zhang JH, Chung TD, Oldenburg KR. A Simple Statistical Parameter for Use in Evaluation and Validation of High Throughput Screening Assays. J Biomol Screen. 1999; 4(2):67-73.

Zhong Y, Wu Y, Liu R, Li Z, Chen Y, Evans T, Chuang P, Das B, He JC. Novel retinoic acid receptor alpha agonists for treatment of kidney disease. PLoS One. 2011; 6(11):e27945.

Brozewicz et al. (2012) European J of Medicinal Chemistry, 55:384-394.

* cited by examiner (A)  +  →

(B)  +  →

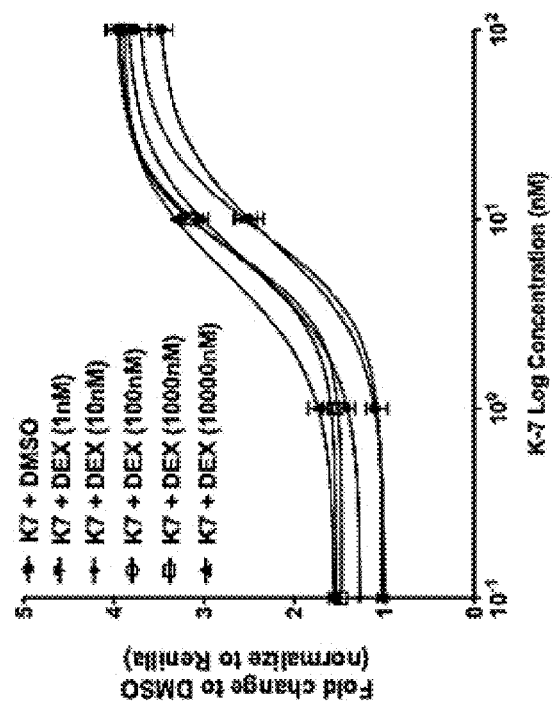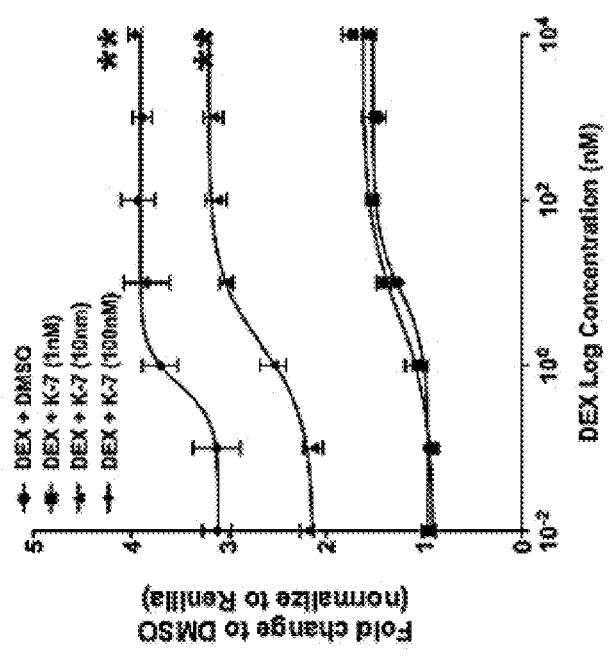
FIG. 20A
FIG. 20B

KRÜPPEL-LIKE FACTOR 15 (KLF15) SMALL MOLECULE AGONISTS IN KIDNEY DISEASE

CROSS-REFERENCE TO RELATED APPLICATIONS

This application claims the benefit of U.S. Application No. 63/018,247, filed on Apr. 30, 2020, the contents of which are hereby incorporated by reference in their entirety.

STATEMENT REGARDING FEDERALLY SPONSORED RESEARCH

This invention was made with government support under grant number 1I01BX003698 awarded by the Department of Veterans Affairs and grant number DK102519 awarded by the National Institutes of Health. The government has certain rights in the invention.

BACKGROUND

Chronic kidney disease (CKD) is a leading risk factor for cardiovascular disease (1, 2), with a disproportionate burden on U.S. Veterans (3). The primary etiology of CKD is a direct consequence of initial dysfunction and injury to the glomerulus, the kidney filtration barrier. Podocytes (visceral epithelial cells) in normal mature glomerulus are regarded as highly differentiated and quiescent cells. In many glomerular diseases such as Focal Segmental Glomerulosclerosis (FSGS) and HIV-associated nephropathy (HIVAN), podocytes are injured (4) and undergo a major change in phenotype resulting in a loss of podocyte cytoskeleton, actin stress fiber formation, and their terminal differentiation markers (5). Over the past two decades, identification of novel mediators has contributed significantly to an understanding of the mechanisms mediating podocytopathy in glomerular diseases (6). However, the lack of novel therapeutics that can make a significant impact in the prevention and treatment of these diseases remains a major gap in the field.

Over the past 10 years, the critical role of Krüppel-Like Factor 15 (KLF15) in podocytopathies has been investigated. KLF15 belongs to a subclass of zinc-finger family of DNA-binding transcriptional regulators that are involved in a broad range of cellular processes (i.e., cell differentiation, apoptosis, cell proliferation) (7). Specifically, the salutary benefits of KLF15 in kidney disease were demonstrated through a series of in vitro and in vivo loss of function and gain of function studies in podocytes (8-10). Furthermore, these studies underscored the mechanisms by which KLF15 transcriptionally regulates key podocyte-specific genes that are required to stabilize the actin cytoskeleton in the setting of cell stress. In addition, it was reported that KLF15 is required to prevent the progression of kidney fibrosis in murine models of progressive kidney fibrosis (11). To contribute to the scientific rigor of these data, recent studies have validated these findings on the salutary effects of KLF15 in kidney disease (8-13). Finally, it was also observed that KLF15 expression is reduced in kidney biopsies with FSGS as compared to healthy donor nephrectomies (8).

Glucocorticoids (GCs) are the initial treatment option for many glomerular diseases, such as Minimal Change Disease (MCD) and FSGS (14). In many instances, alternate immunosuppressive therapy is typically not considered until patients have failed GC therapy. Although GCs can be effective at times, it has been challenging for nephrologists to determine early which individuals are likely to respond to GC therapy (15). For instance, treatment with FSGS requires a minimum of 16 weeks of GC therapy (15), thereby resulting in their prolonged use leading to systemic adverse effects, ranging from weight gain, hyperglycemia, and systemic infections. It was recently demonstrated that KLF15 is a GC-responsive gene and the loss of KLF15 in podocytes attenuated the salutary effects of GCs in two preclinical proteinuric murine models (9). In addition, it was observed that the podocyte-specific expression of KLF15 in human kidney biopsies correlated with responsiveness to GCs in primary glomerulopathies such as FSGS and MCD (9). Based on these data collectively, an investigation into the mechanisms mediating the salutary effects of GC-KLF15 signaling in podocytes was undertaken. It was demonstrated that induction of podocyte-specific human KLF15 (hKLF15) ameliorated albuminuria, podocyte injury, FSGS, interstitial fibrosis, and overall kidney function in two preclinical proteinuric murine models (10).

Despite this strong rigor of prior research, the identification and development of KLF15 agonists as therapeutics in primary glomerulopathies has remained elusive.

Without wishing to be bound by theory, the identification of therapeutic targets that attenuate the progression of CKD is of major interest to the medical community, given the high cardiovascular morbidity and mortality among U.S. Veterans. Glomerular disease is the major cause of CKD and targeted therapy is unfortunately very limited. Since podocyte injury is a major cause of glomerular disease, identification and optimization of small molecules that restore podocyte health is a logical therapeutic strategy. To date, the initial treatment in the management of primary glomerulopathies remains high-dose GCs. Although some individuals respond to GCs, many are nonresponsive and resort to use of other immunomodulatory agents (15). Recent data suggest that KLF15 acts not only as an injury response gene, but a loss of KLF15 increases the susceptibility to podocyte injury (8). It was also recently reported that KLF15 is required for the renal protective effects of GCs in primary glomerulopathies and that induction of KLF15 ameliorated kidney disease in preclinical murine models without the systemic toxicity observed in chronic GC use (10). Consequently, targeting molecules downstream of the GC-signaling pathway, such as KLF15, may minimize systemic toxicity without jeopardizing therapeutic efficacy. Accordingly, the development and optimization of lead KLF15 agonists for use in preclinical models of proteinuric diseases is therefore highly significant and clinically relevant. These needs and others are met by the present invention.

SUMMARY

In accordance with the purpose(s) of the invention, as embodied and broadly described herein, the invention, in one aspect, relates to compounds and compositions for use in the prevention and treatment of disorders associated with Krüppel-Like Factor 15 (KLF15) signaling dysfunction such as, for example, kidney disease (e.g., chronic kidney disease), heart disease, obesity, and neurodegenerative disorders (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)).

Thus, disclosed are compounds having a structure represented by a formula selected from:

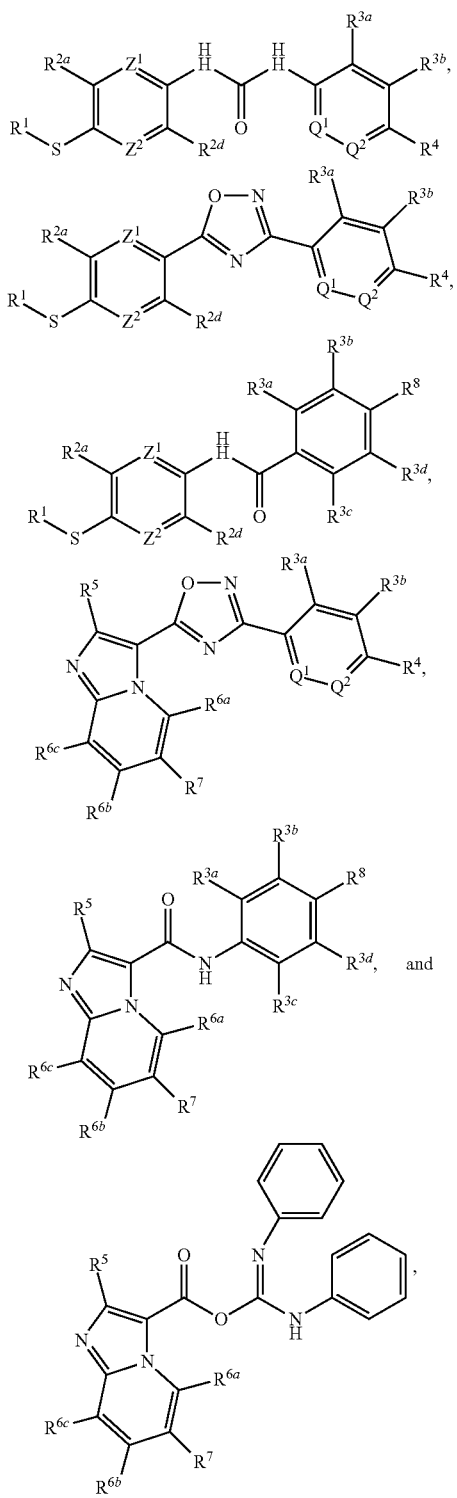

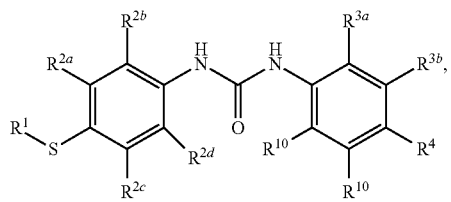

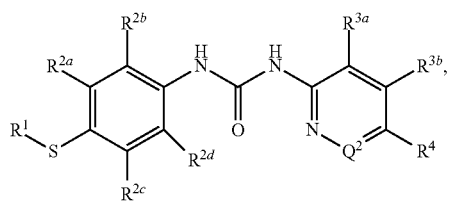

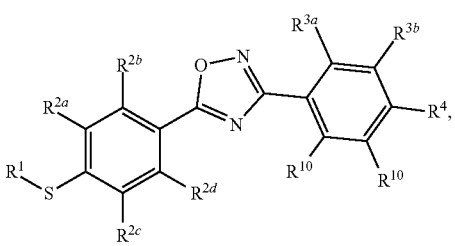

wherein each of $Q^1$ and $Q^2$, when present, is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$, when present, is independently selected from halogen, —CN, —OH, C1-C4 alkyl, C1-C4 alkoxy, —B(OR$^{11}$)$_2$, and —B(R$^{12}$)$_3$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —B(OR$^{11}$)$_2$ and —B(R$^{12}$)$_3$, provided that when the compound has a structure represented by a formula then $R^4$ is —B(OR$^{11}$)$_2$, provided that when the compound has a structure represented by a formula:

then $R^4$ is not halogen, and provided that when the compound has a structure represented by a formula:

then $R^4$ is not —OH, or a pharmaceutically acceptable salt thereof.

Also disclosed are compounds having a structure represented by a formula selected from:

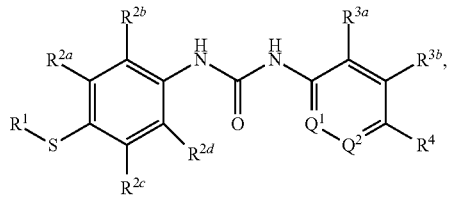

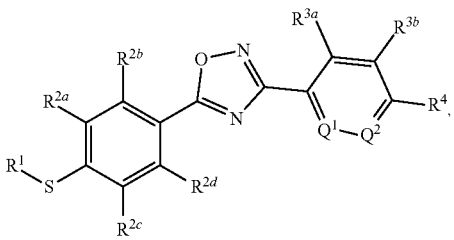

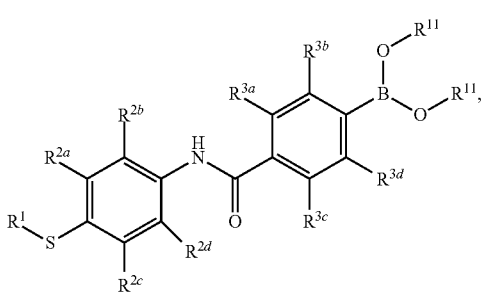

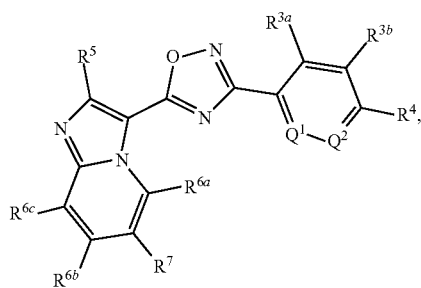

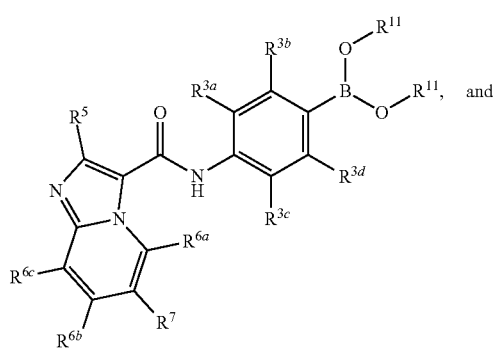

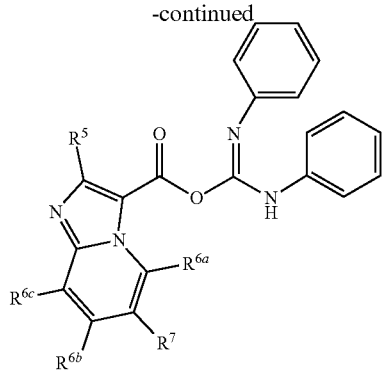

wherein each of $Q^1$ and $Q^2$, when present, is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$, when present, is independently selected from halogen, —CN, —OH, C1-C4 alkyl, C1-C4 alkoxy, and —B(OR$^{11}$)$_2$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^7$, when present, is halogen, provided that when the compound has a structure represented by a formula:

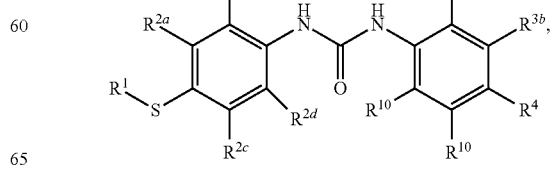

then R⁴ is —B(OR¹¹)₂, provided that when the compound has a structure represented by a formula:

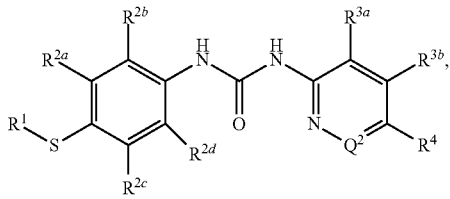

then R⁴ is not halogen, and provided that when the compound has a structure represented by a formula:

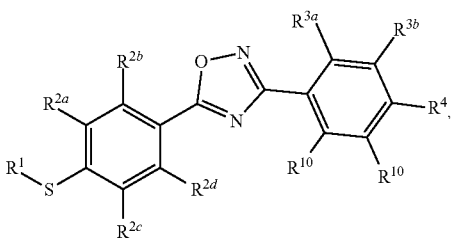

then R⁴ is not —OH, or a pharmaceutically acceptable salt thereof.

Also disclosed are pharmaceutical compositions comprising an effective amount of a disclosed compound and a pharmaceutically acceptable carrier.

Also disclosed are methods for treating a disorder associated with Krüppel-Like Factor 15 (KLF15) signaling dysfunction in a subject in need thereof, the method comprising administering to the subject an effective amount of a compound having a structure represented by a formula selected from:

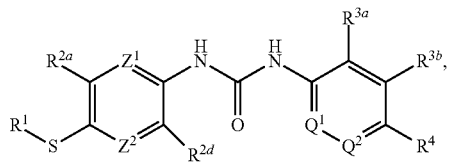

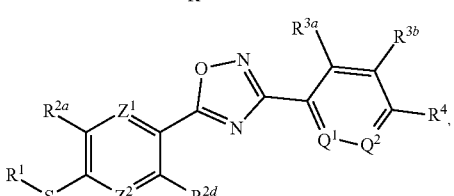

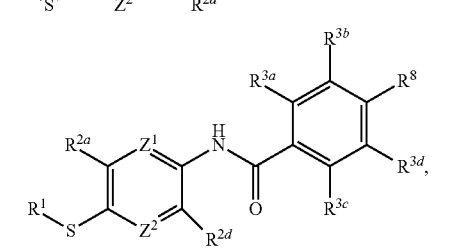

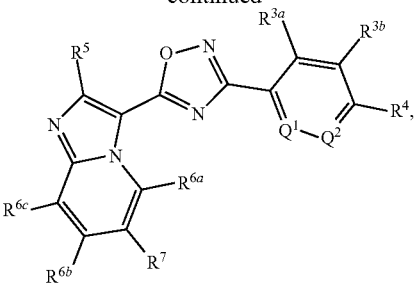

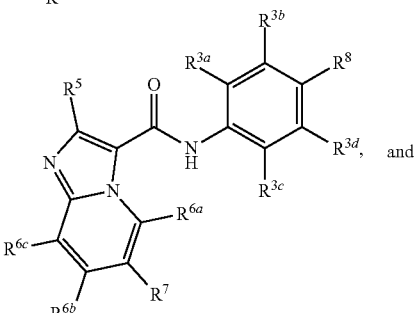

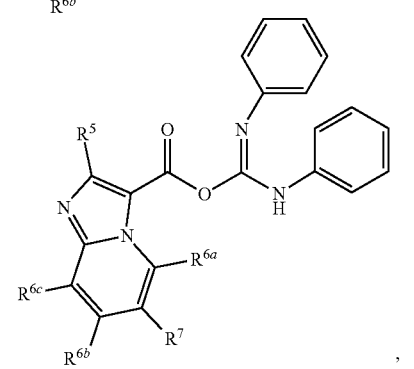

wherein each of $Q^1$ an $Q^2$ is independently selected from N and $CR^{10}$; wherein $R^{10}$, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, —B(OR¹¹)₂, and —B(R¹²)₃; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —B(OR$^{11}$)$_2$ and —B(R$^{12}$)$_3$, provided that when the compound has a structure represented by a formula:

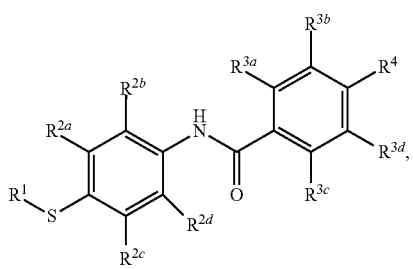

then $R^4$ is —OH, C1-C4 alkyl, C1-C4 alkoxy, or —B(OR$^{11}$)$_2$; or a pharmaceutically acceptable salt thereof, thereby treating the disorder associated with KLF15 signaling dysfunction in the subject.

Also disclosed are methods for treating a disorder associated with Krüppel-Like Factor 15 (KLF15) signaling dysfunction in a subject in need thereof, the method comprising administering to the subject an effective amount of a compound having a structure represented by a formula selected from:

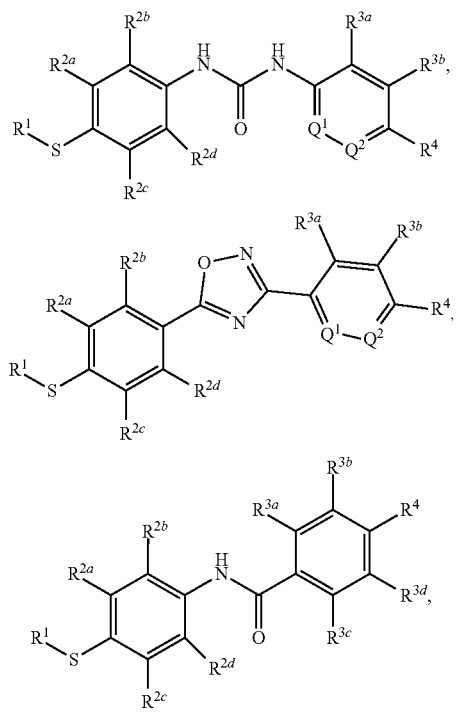

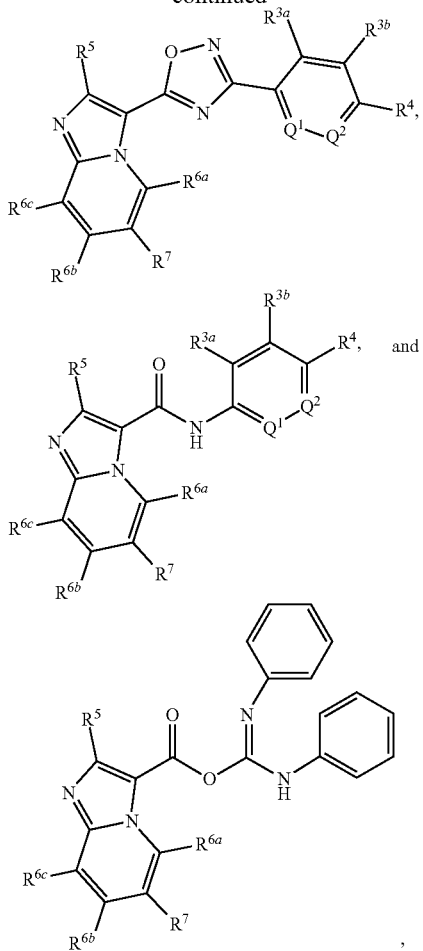

wherein each of $Q^1$ and $Q^2$ is independently selected from N and CR$^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, and —B(OR$^{11}$)$_2$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^7$, when present, is halogen, provided that when the compound has a structure represented by a formula:

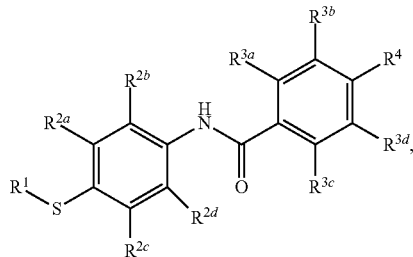

then R$^4$ is —OH, C1-C4 alkyl, C1-C4 alkoxy, or —B(OR$^{11}$)$_2$; or a pharmaceutically acceptable salt thereof, thereby treating the disorder associated with KLF15 signaling dysfunction in the subject.

Also disclosed are methods for modifying KLF15 signaling in a subject, the method comprising administering to the subject an effective amount of a compound having a structure selected from:

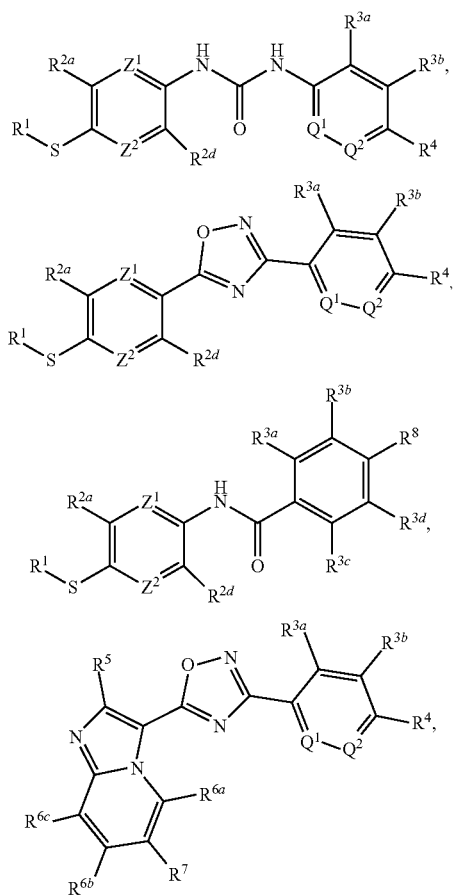

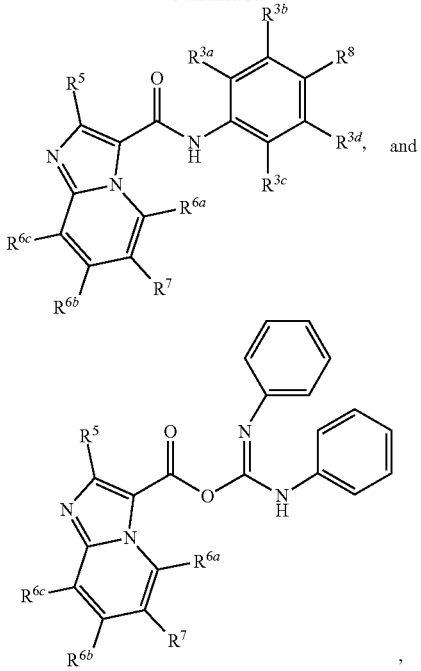

wherein each of Q$^1$ and Q$^2$ is independently selected from N and CR$^{10}$; wherein R$^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Z$^1$, when present, is selected from N and CR$^{2b}$; wherein Z$^2$, when present, is selected from N and CR$^{2c}$; wherein R$^1$, when present, is C1-C4 alkyl; wherein each of R$^{2a}$, R$^{2b}$, R$^{2c}$, R$^{2d}$, R$^{3a}$, and R$^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{3c}$ and R$^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is independently selected from halogen, —CN, —OH, C1-C4 alkyl, C1-C4 alkoxy, —B(OR$^{11}$)$_2$, and —B(R$^{12}$)$_3$; wherein each occurrence of R$^{11}$, when present, is independently selected from hydrogen and C1-C8 alkyl, or wherein each occurrence of R$^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of R$^{12}$, when present, is independently halogen; wherein each of R$^5$, R$^{6a}$, R$^{6b}$, and R$^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^7$, when present, is halogen; and wherein R$^8$, when present, is selected from —B(OR$^{11}$)$_2$ and —B(R$^{12}$)$_3$, provided that when the compound has a structure represented by a formula:

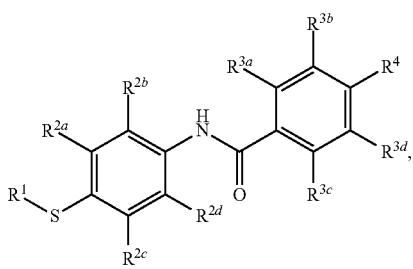

then R⁴ is —OH, C1-C4 alkyl, C1-C4 alkoxy, or —B(OR¹¹)₂; or a pharmaceutically acceptable salt thereof, thereby modifying KLF15 signaling in the subject.

Also disclosed are methods for modifying KLF15 signaling in a subject, the method comprising administering to the subject an effective amount of a compound having a structure selected from:

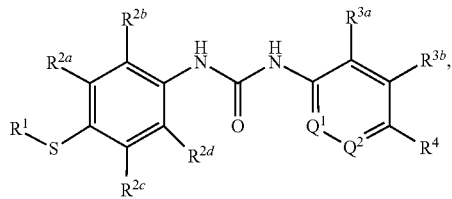

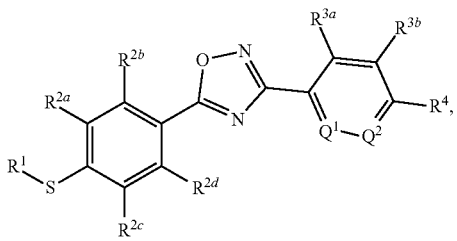

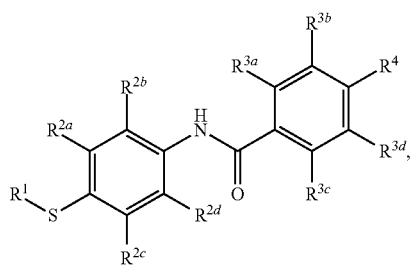

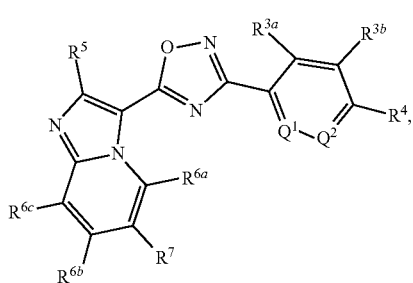

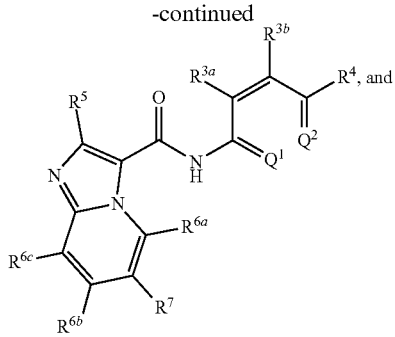

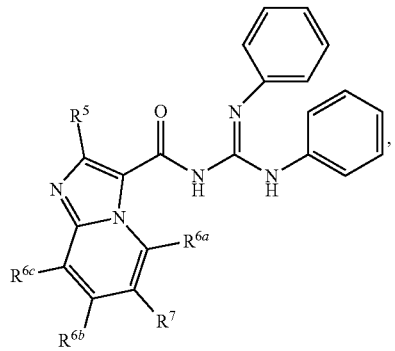

wherein each of Q¹ and Q² is independently selected from N and CR¹⁰; wherein R¹⁰, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹, when present, is C1-C4 alkyl; wherein each of R²ᵃ, R²ᵇ, R²ᶜ, R²ᵈ, R³ᵃ, and R³ᵇ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R³ᶜ and R³ᵈ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is independently selected from halogen, —CN, —OH, C1-C4 alkyl, C1-C4 alkoxy, and —B(OR¹¹)₂; wherein each occurrence of R¹¹, when present, is independently selected from hydrogen and C1-C8 alkyl, or wherein each occurrence of R¹¹, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of R⁵, R⁶ᵃ, R⁶ᵇ, and R⁶ᶜ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R⁷, when present, is halogen, provided that when the compound has a structure represented by a formula:

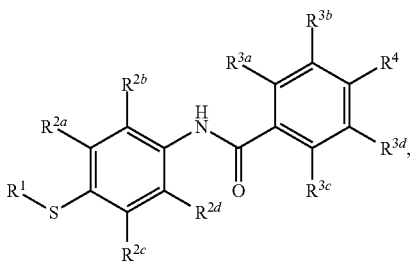

then R⁴ is —OH, C1-C4 alkyl, C1-C4 alkoxy, or —B(OR¹¹)₂; or a pharmaceutically acceptable salt thereof, thereby modifying KLF15 signaling in the subject.

Also disclosed are methods for modifying KLF15 in a cell, the method comprising contacting the cell with an effective amount of a compound having a structure selected from:

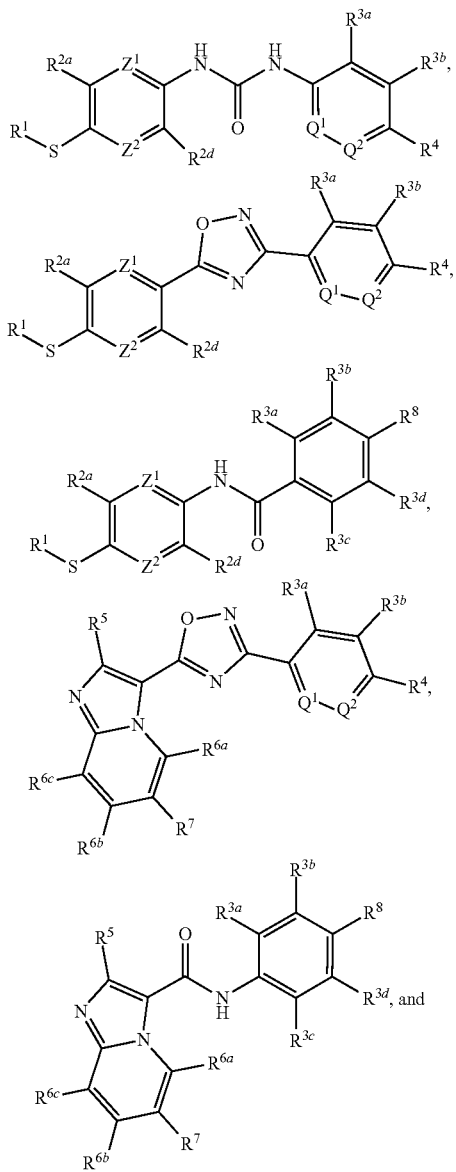

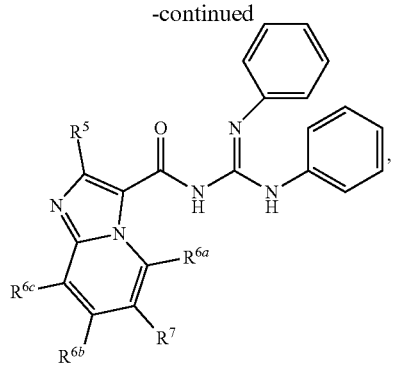

wherein each of $Q^1$ and $Q^2$ is independently selected from N and $CR^{10}$; wherein $R^{10}$, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, —B(OR¹¹)₂, and —B(R¹²)₃; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —B(OR¹¹)₂ and —B(R¹²)₃, provided that when the compound has a structure represented by a formula:

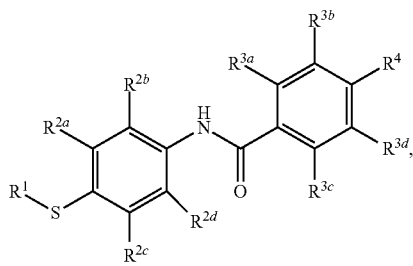

then R⁴ is —OH, C1-C4 alkyl, C1-C4 alkoxy, or —B(OR¹¹)₂; or a pharmaceutically acceptable salt thereof, thereby modifying KLF15 signaling in the cell.

Also disclosed are methods for modifying KLF15 in a cell, the method comprising contacting the cell with an effective amount of a compound having a structure represented by a formula selected from:

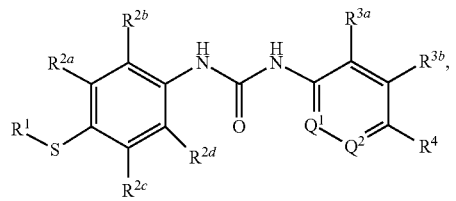

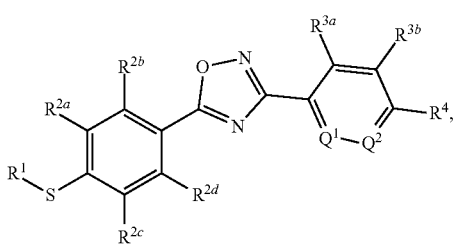

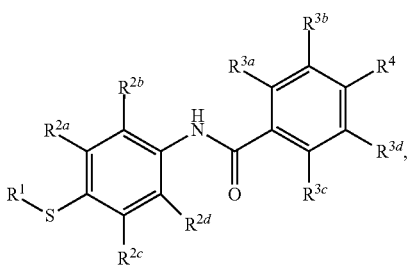

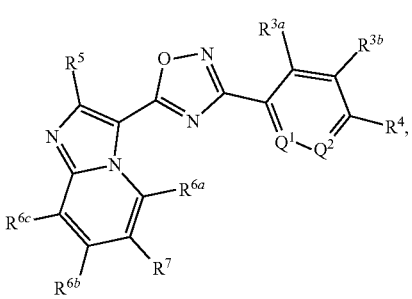

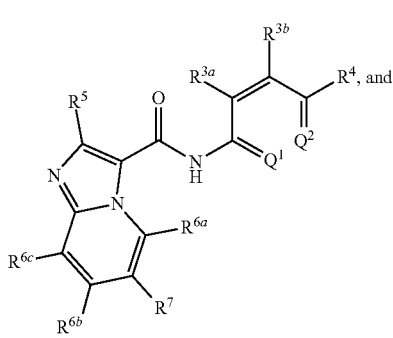

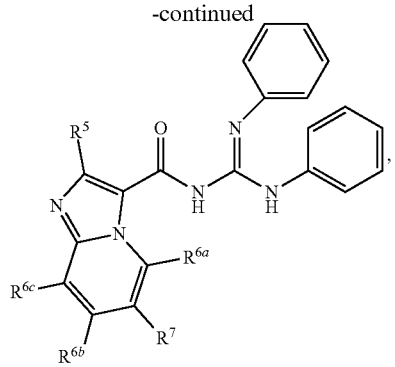

wherein each of $Q^1$ and $Q^2$ is independently selected from N and $CR^{10}$; wherein $R^{10}$, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, and —B(OR¹¹)₂; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^7$, when present, is halogen, provided that when the compound has a structure represented by a formula:

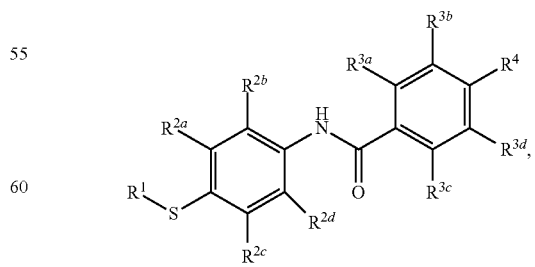

then R⁴ is —OH, C1-C4 alkyl, C1-C4 alkoxy, or —B(OR¹¹)₂; or a pharmaceutically acceptable salt thereof, thereby modifying KLF15 signaling in the cell.

Also disclosed are kits comprising a compound having a structure represented by a formula selected from:

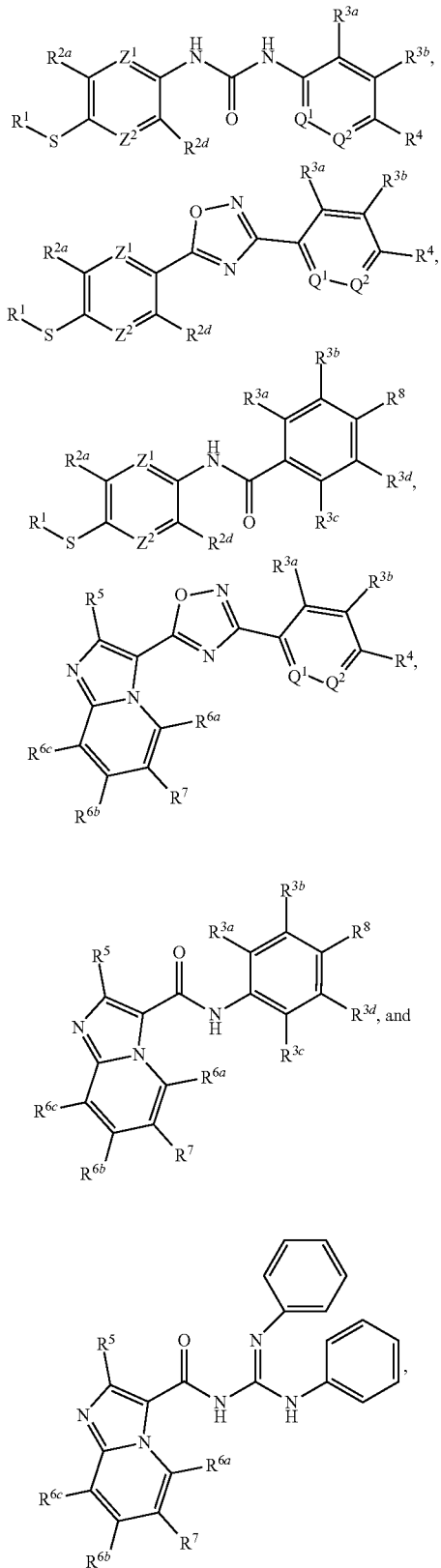

wherein each of $Q^1$ and $Q^2$ is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, —B(OR$^{11}$)$_2$, and —B(R$^{12}$)$_3$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —B(OR$^{11}$)$_2$ and —B(R$^{12}$)$_3$, provided that when the compound has a structure represented by a formula:

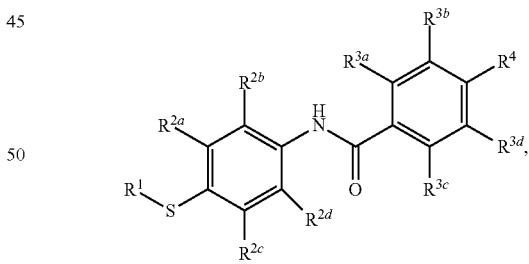

then $R^4$ is —OH, C1-C4 alkyl, C1-C4 alkoxy, or —B(OR$^{11}$)$_2$; or a pharmaceutically acceptable salt thereof, and one or more of: (a) an agent associated with the treatment of a disorder associated with KLF15 signaling dysfunction; (b) instructions for administering the compound in connection with treating a disorder associated with KLF15 signaling dysfunction; and (c) instructions for treating a disorder associated with KLF15 signaling dysfunction.

Also disclosed are kits comprising a compound having a structure represented by a formula selected from:

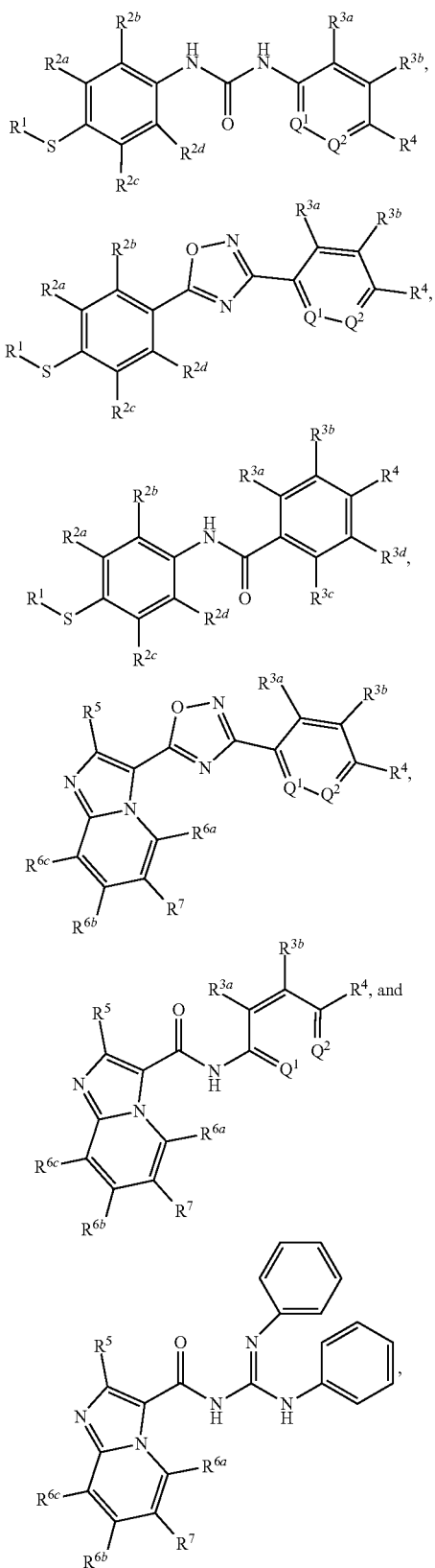

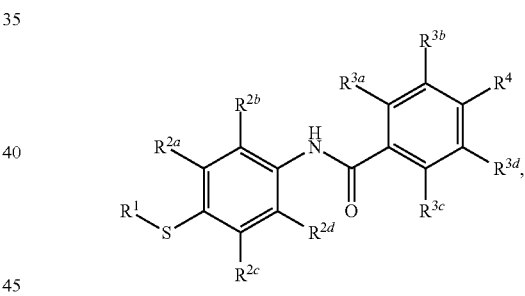

wherein each of $Q^1$ and $Q^2$ is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, and —B(OR$^{11}$)$_2$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^7$, when present, is halogen, provided that when the compound has a structure represented by a formula:

then $R^4$ is —OH, C1-C4 alkyl, C1-C4 alkoxy, or —B(OR$^{11}$)$_2$; or a pharmaceutically acceptable salt thereof, and one or more of: (a) an agent associated with the treatment of a disorder associated with KLF15 signaling dysfunction; (b) a glucocorticoid; (c) instructions for administering the compound in connection with treating a disorder associated with KLF15 signaling dysfunction; and (d) instructions for treating a disorder associated with KLF15 signaling dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including mat-

BRIEF DESCRIPTION OF THE FIGURES

The accompanying figures, which are incorporated in and constitute a part of this specification, illustrate several aspects and together with the description serve to explain the principles of the invention.

FIG. 20A-C show representative data illustrating a dose-response curve with DEX with and without escalating dose of K-7 (1, 10, and 100 nM) (FIG. 20A), a dose-response curve with K-7 and escalating dose of DEX (1, 10, 100, 1000, and 10,000 nM) (FIG. 20B), and fold change in KLF15 reporter activity (relative to renilla) in K-7 (1 μM), DEX (1 μM), DEX (0.5 μM)+K-7 (10 nM), and DEX (0.5 μM)+K-7 (100 nM) (FIG. 20C).

Figure 1B:
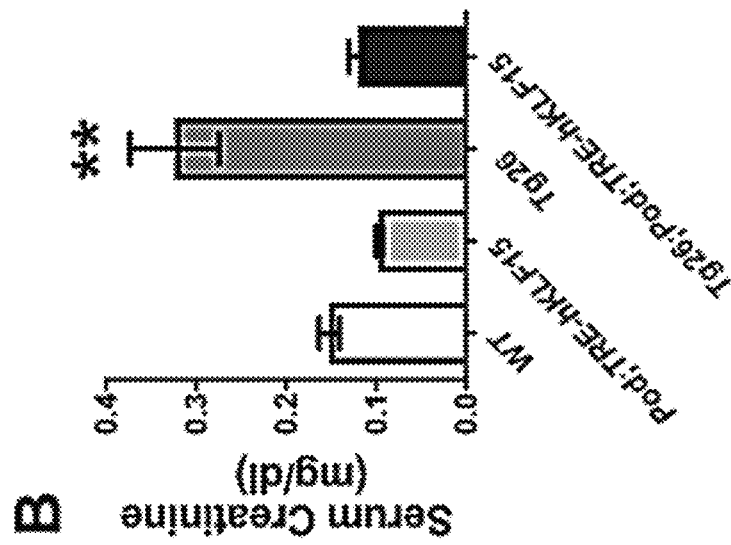
FIG. 1A-D show representative data illustrating albuminuria (FIG. 1A), serum creatinine (FIG. 1B), % mouse survival over time (FIG. 1C), and scoring of % fibrosis and inflammation score (FSGS), Global Sclerosis, tubulointerstitial fibrosis and inflammation in PODTA, PODTA; TRE-KLF15, Tg26; TRE-KLF15, and Tg26; PODTA; TRE-KLF15 mice (FIG. 1D). All mice are DOX treated (FVB/N strain).
Figure 1A:
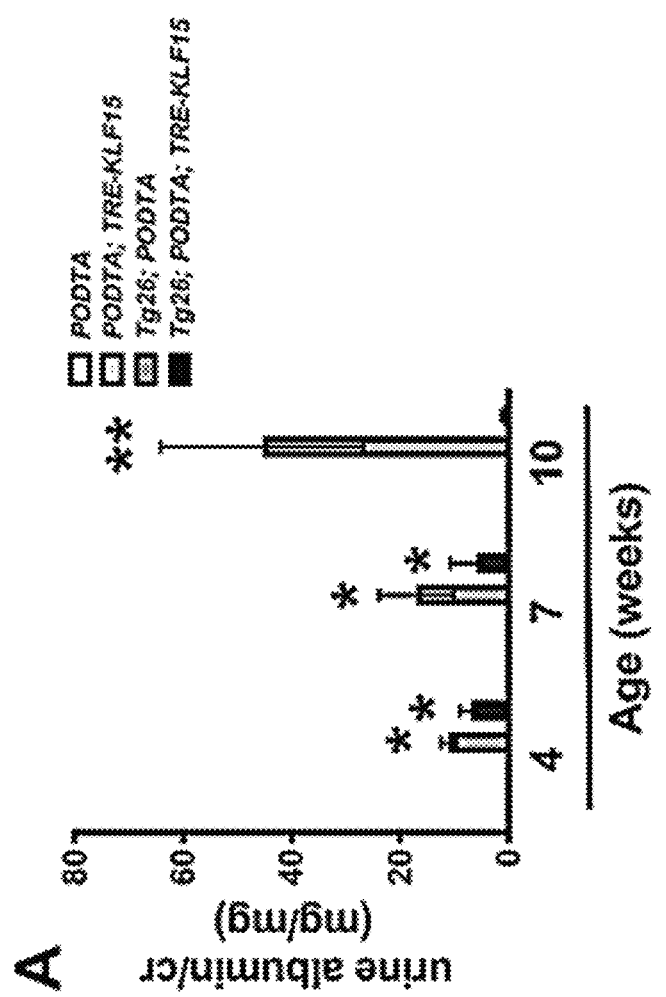
Figures 1C, 1D:
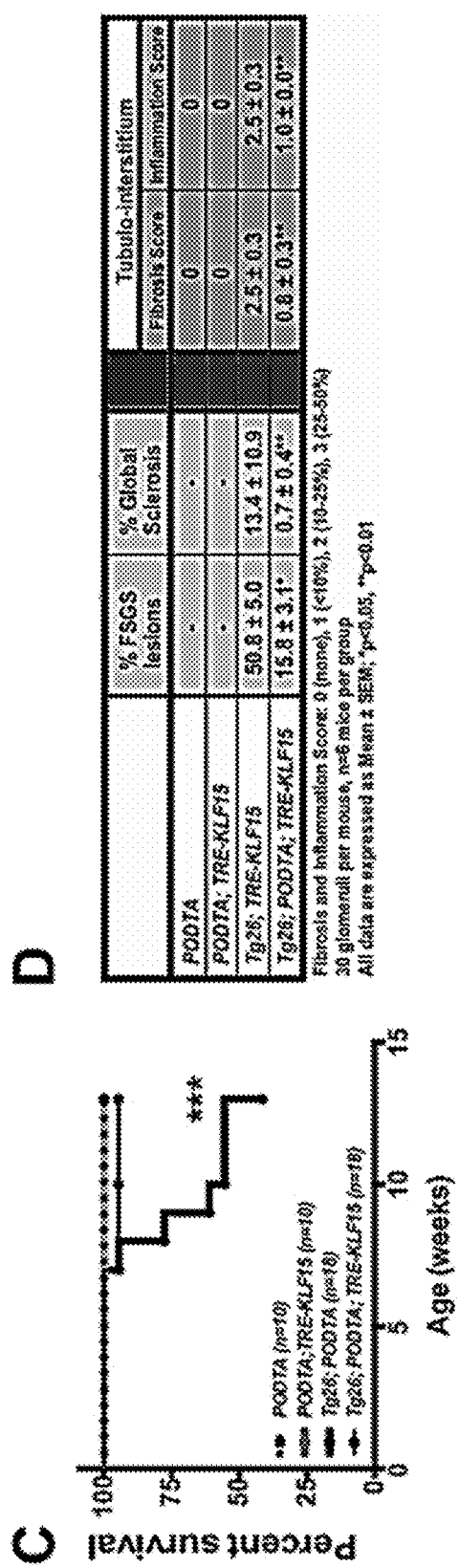

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of".

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half-maximal (50%) inhibitory concentration (IC) of a substance.

As used herein, "$EC_{50}$" is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-cancer and antineoplastic agents such as kinase inhibitors, poly ADP ribose polymerase (PARP) inhibitors and other DNA damage response modifiers, epigenetic agents such as bromodomain and extra-terminal (BET) inhibitors, histone deacetylase (HDAc) inhibitors, iron chelators and other ribonucleotides reductase inhibitors, proteasome inhibitors and Nedd8-activating enzyme (NAE) inhibitors, mammalian target of rapamycin (mTOR) inhibitors, traditional cytotoxic agents such as paclitaxel, dox, irinotecan, and platinum compounds, immune checkpoint blockade agents such as cytotoxic T lymphocyte antigen-4 (CTLA-4) monoclonal antibody (mAB), programmed cell death protein 1 (PD-1)/programmed cell death-ligand 1 (PD-L1) mAB, cluster of differentiation 47 (CD47) mAB, toll-like receptor (TLR) agonists and other immune modifiers, cell therapeutics such as chimeric antigen receptor T-cell (CAR-T)/chimeric antigen receptor natural killer (CAR-NK) cells, and proteins such as interferons (IFNs), interleukins (ILs), and mAbs; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a non-aromatic carbon-based ring type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group that has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

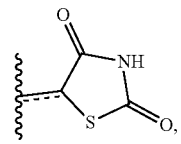

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

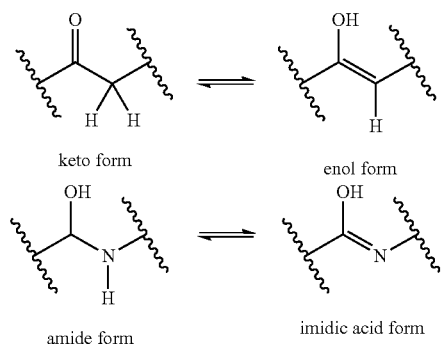

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

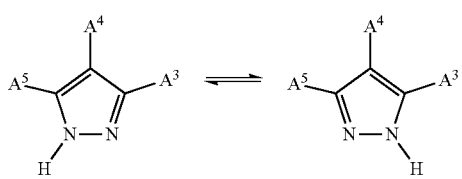

Unless stated to the contrary, the invention includes all such possible tautomers.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

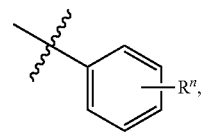

which is understood to be equivalent to a formula:

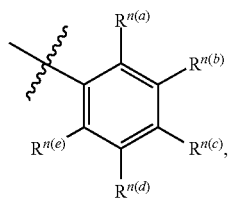

wherein n is typically an integer. That is, R is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in treating disorders associated with KLF15 signaling dysfunction such as, for example, kidney disease (e.g., chronic kidney disease), heart disease, obesity, and neurodegenerative disorders (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)).

In one aspect, the compounds of the invention are useful in activating KLF15 signaling in a mammal. In a further aspect, the compounds of the invention are useful in activating KLF15 in at least one cell.

In one aspect, the compounds of the invention are useful in the treatment of kidney disease, as further described herein. In one aspect, the compounds of the invention are useful in the treatment of a neurodegenerative disorder, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

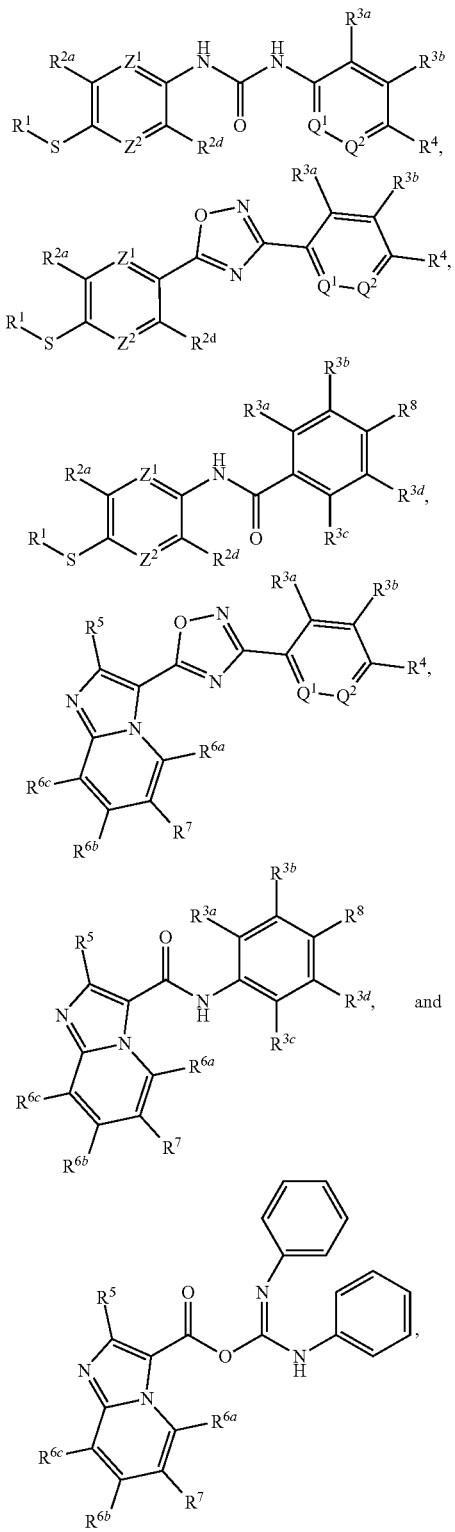

wherein each of $Q^1$ and $Q^2$, when present, is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Z$^1$, when present, is selected from N and CR$^{2b}$; wherein Z$^2$, when present, is selected from N and CR$^{2c}$; wherein R$^1$, when present, is C1-C4 alkyl; wherein each of R$^{2a}$, R$^{2b}$, R$^{2c}$, R$^{2d}$, R$^{3a}$, and R$^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{3c}$ and R$^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$, when present, is independently selected from halogen, —CN, —OH, C1-C4 alkyl, C1-C4 alkoxy, —B(OR$^{11}$)$_2$, and —B(R$^{12}$)$_3$; wherein each occurrence of R$^{11}$, when present, is independently selected from hydrogen and C1-C8 alkyl, or wherein each occurrence of R$^1$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of R$^{12}$, when present, is independently halogen; wherein each of R$^5$, R$^{6a}$, R$^{6b}$, and R$^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^7$, when present, is halogen; and wherein R$^8$, when present, is selected from —B(OR$^{11}$)$_2$ and —B(R$^{12}$)$_3$, provided that when the compound has a structure represented by a formula:

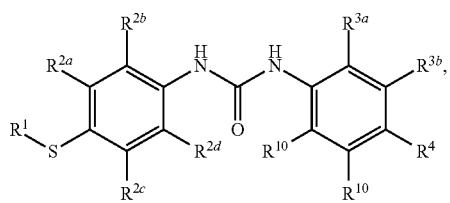

then R$^4$ is —B(OR$^{11}$)$_2$, provided that when the compound has a structure represented by a formula:

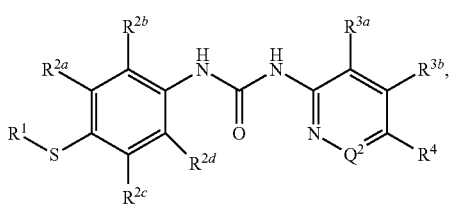

then R$^4$ is not halogen, and provided that when the compound has a structure represented by a formula:

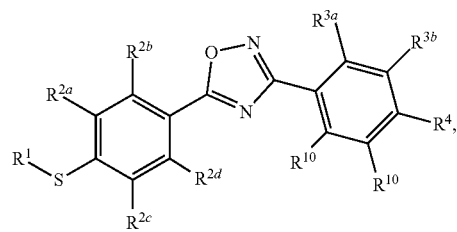

then R$^4$ is not —OH, or a pharmaceutically acceptable salt thereof.

In one aspect, disclosed are compounds having a structure represented by a formula selected from:

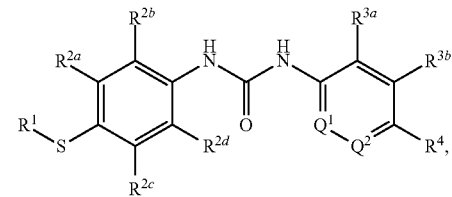

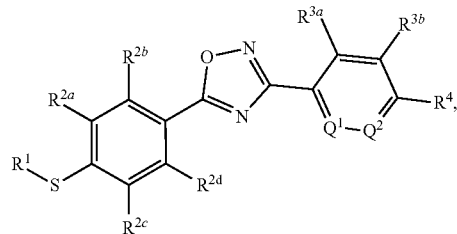

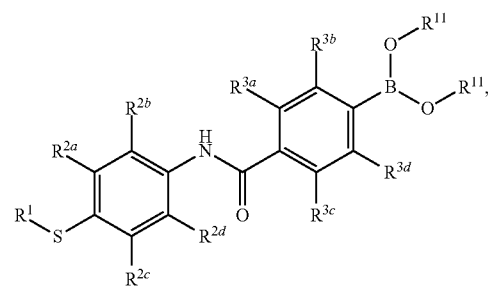

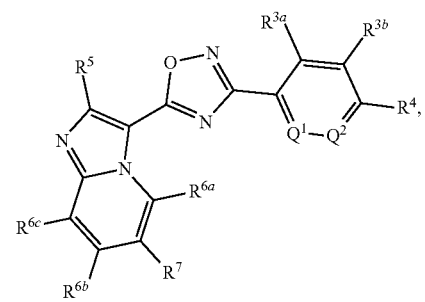

-continued

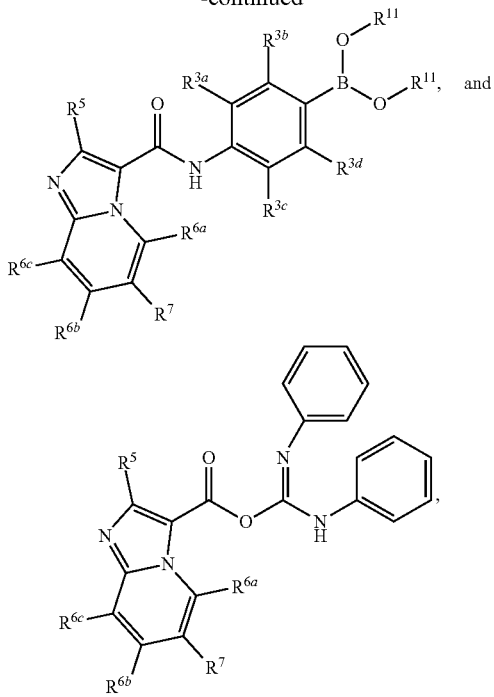

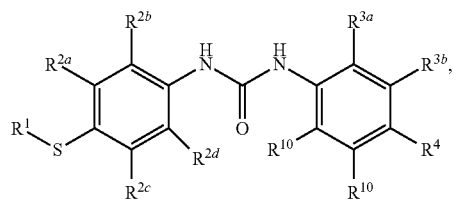

then $R^4$ is —B(OR$^{11}$)$_2$, provided that when the compound has a structure represented by a formula:

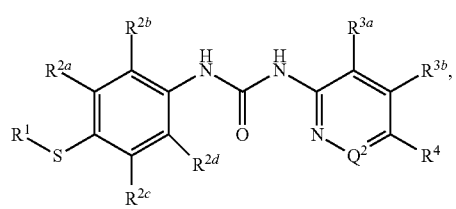

then $R^4$ is not halogen, and provided that when the compound has a structure represented by a formula:

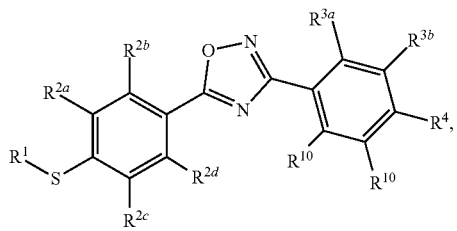

then $R^4$ is not —OH, or a pharmaceutically acceptable salt thereof.

In one aspect, disclosed are compounds having a structure represented by a formula selected from:

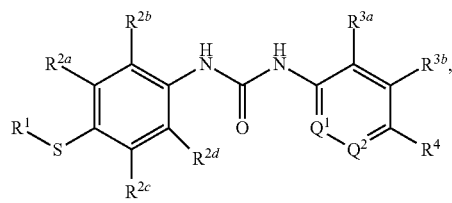

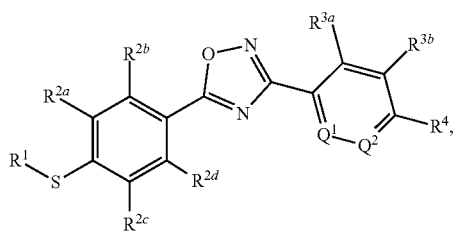

wherein each of $Q^1$ and $Q^2$, when present, is independently selected from N and CR$^{10}$; wherein R$^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^1$, when present, is C1-C4 alkyl; wherein each of R$^{2a}$, R$^{2b}$, R$^{2c}$, R$^{2d}$, R$^{3a}$, and R$^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{3c}$ and R$^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$, when present, is independently selected from halogen, —CN, —OH, C1-C4 alkyl, C1-C4 alkoxy, and —B(OR$^{11}$)$_2$; wherein each occurrence of R$^{11}$, when present, is independently selected from hydrogen and C1-C8 alkyl, or wherein each occurrence of R$^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of R$^5$, R$^{6a}$, R$^{6b}$, and R$^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^7$, when present, is halogen, provided that when the compound has a structure represented by a formula:

-continued

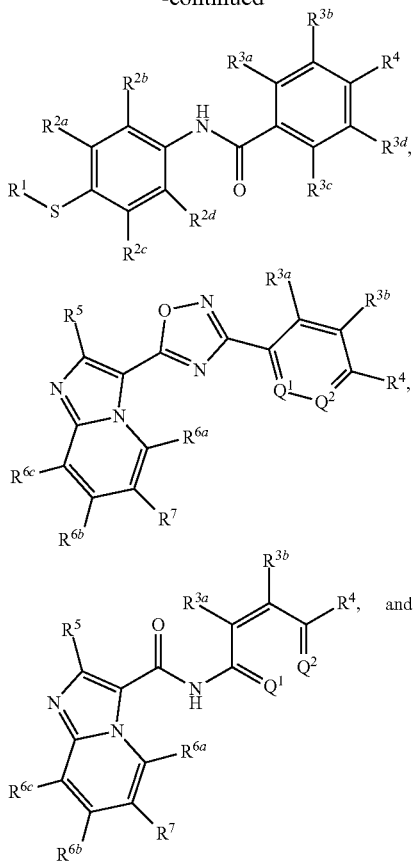

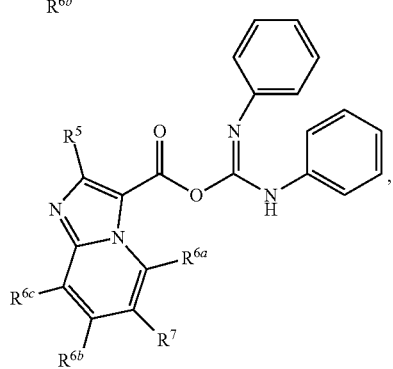

wherein each of Q¹ and Q² is independently selected from N and CR¹⁰; wherein R¹⁰, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is independently selected from halogen, —CN, —OH, C1-C4 alkyl, C1-C4 alkoxy, and —B(OR¹¹)₂; wherein each occurrence of R¹¹, when present, is independently selected from hydrogen and C1-C8 alkyl, or wherein each occurrence of R¹¹, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of R⁵, $R^{6a}$, $R^{6b}$, and $R^{6c}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R⁷, when present, is halogen, provided that when the compound has a structure represented by a formula:

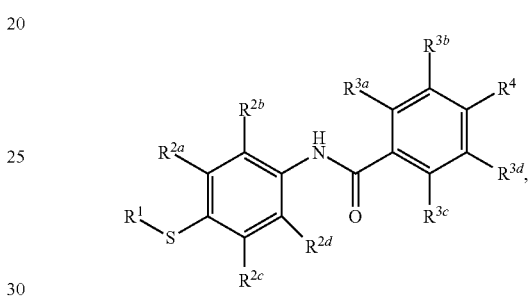

then R⁴ is —OH, C1-C4 alkyl, C1-C4 alkoxy, or —B(OR¹¹)₂.

In one aspect, disclosed are compounds selected from:

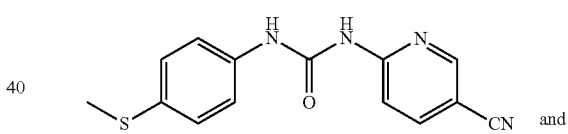

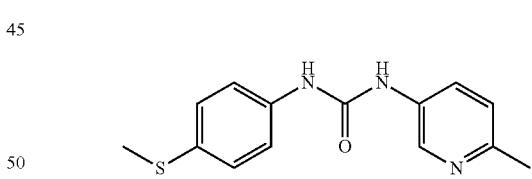

or a pharmaceutically acceptable salt thereof.

In a further aspect, the compound has a structure represented by a formula:

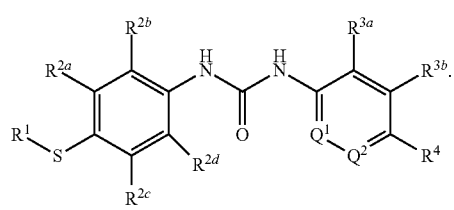

In a further aspect, the compound has a structure represented by a formula:

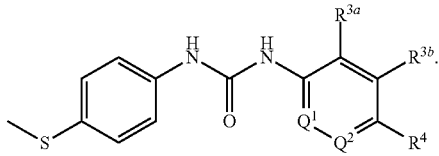

In a further aspect, the compound has a structure represented by a formula selected from:

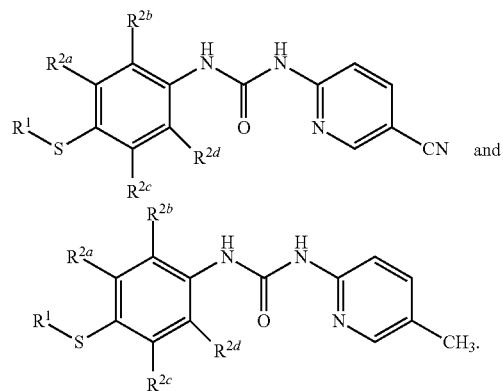

In a further aspect, the compound has a structure represented by a formula:

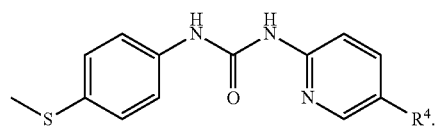

In a further aspect, the compound has a structure represented by a formula:

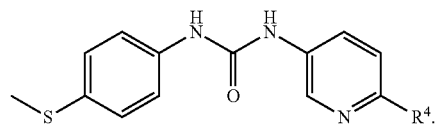

In a further aspect, the compound has a structure represented by a formula selected from:

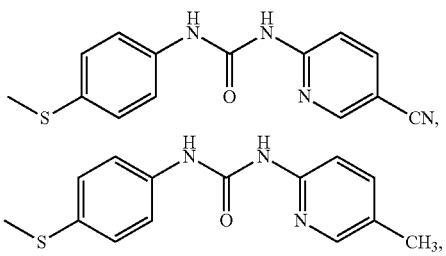

In a further aspect, the compound has a structure represented by a formula selected from:

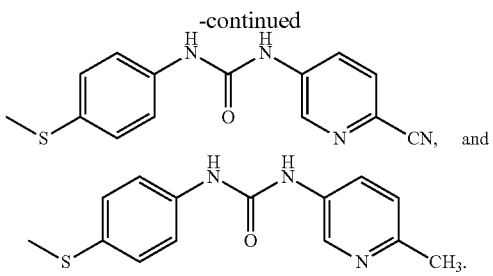

In a further aspect, the compound has a structure represented by a formula:

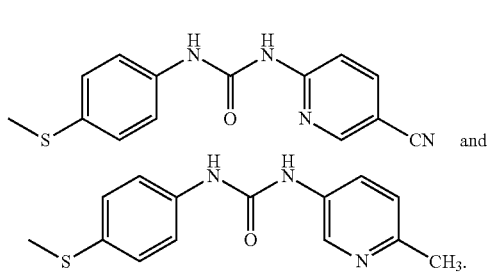

In a further aspect, the compound has a structure represented by a formula:

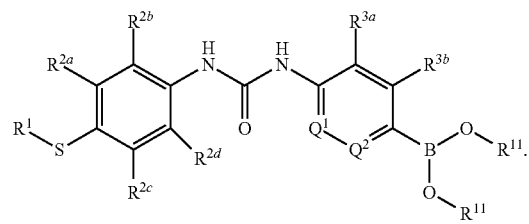

In a further aspect, the compound has a structure represented by a formula:

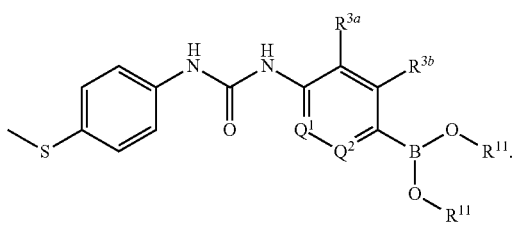

In a further aspect, the compound has a structure represented by a formula:

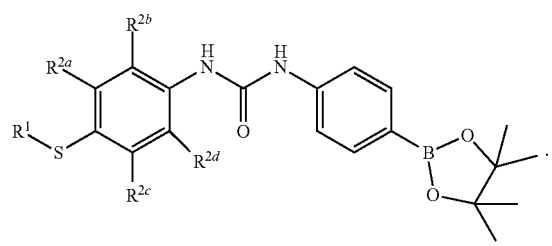

In a further aspect, the compound has a structure represented by a formula:

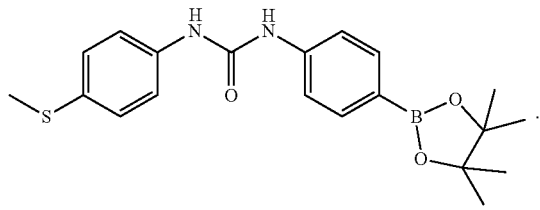

In a further aspect, the compound has a structure represented by a formula:

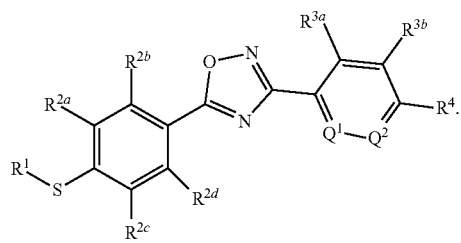

In a further aspect, the compound has a structure represented by a formula:

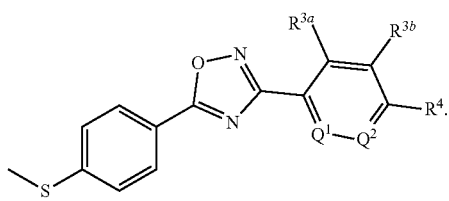

In a further aspect, the compound has a structure represented by a formula:

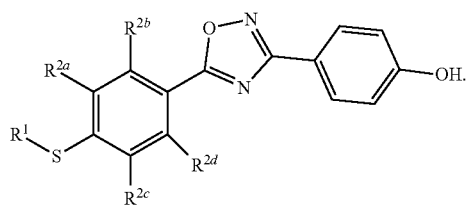

In a further aspect, the compound has a structure represented by a formula:

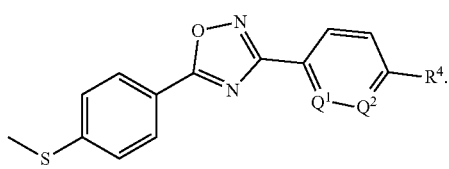

In a further aspect, the compound has a structure represented by a formula:

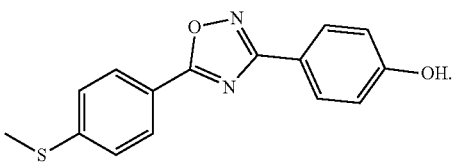 [SMILES: CSc1ccc(-c2nc(-c3ccc(O)cc3)no2)cc1]

In a further aspect, the compound has a structure represented by a formula:

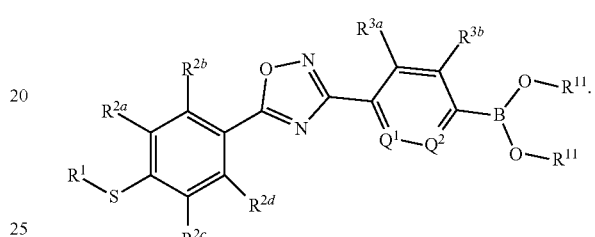

In a further aspect, the compound has a structure represented by a formula:

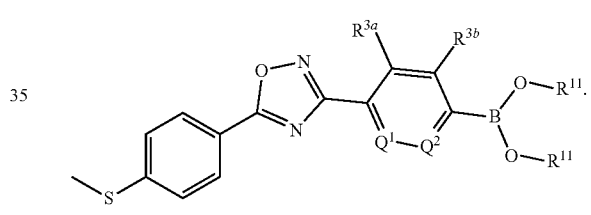

In a further aspect, the compound has a structure represented by a formula:

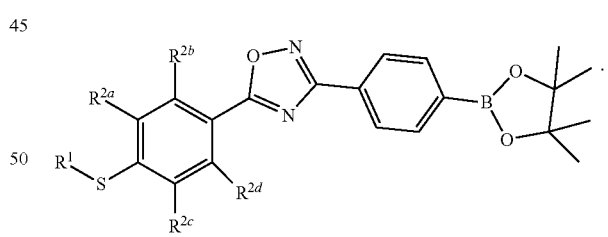

In a further aspect, the compound has a structure represented by a formula:

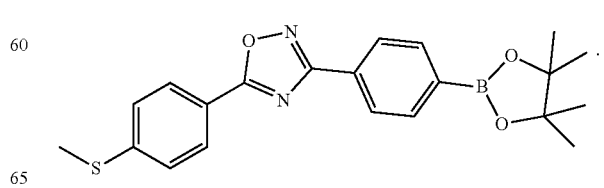

In a further aspect, the compound has a structure represented by a formula:

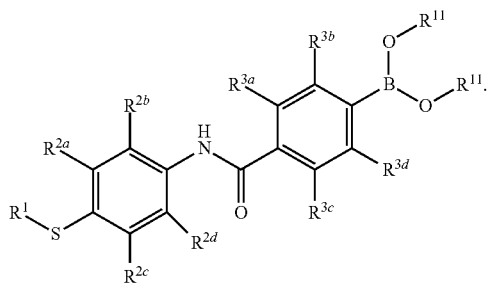

In a further aspect, the compound has a structure represented by a formula:

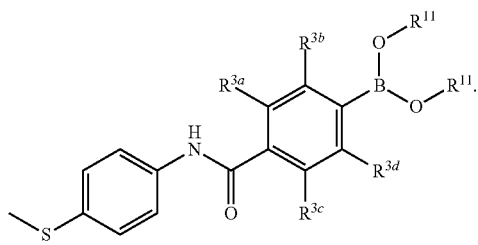

In a further aspect, the compound has a structure represented by a formula:

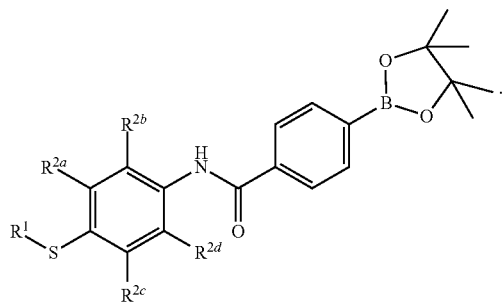

In a further aspect, the compound has a structure represented by a formula:

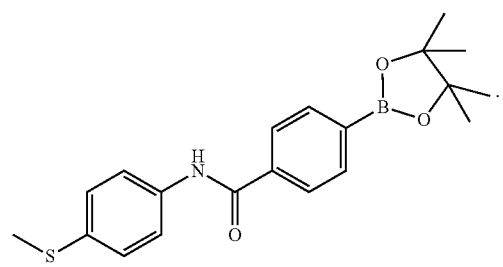

In a further aspect the compound has a structure represented by a formula:

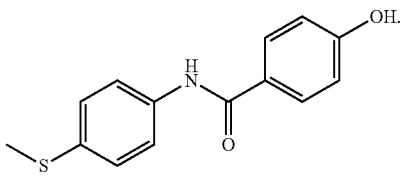 [SMILES: CSc1ccc(NC(=O)c2ccc(O)cc2)cc1]

In a further aspect, the compound has a structure represented by a formula:

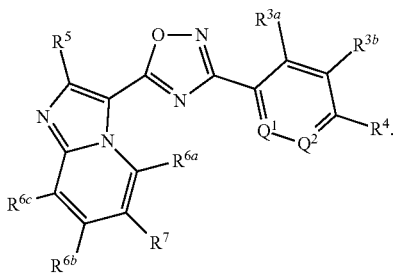

In a further aspect, the compound has a structure represented by a formula:

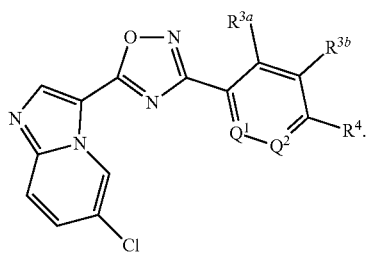

In a further aspect, the compound has a structure represented by a formula:

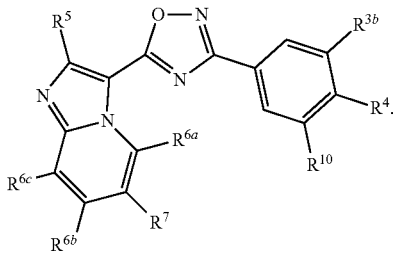

In a further aspect, the compound has a structure represented by a formula selected from:

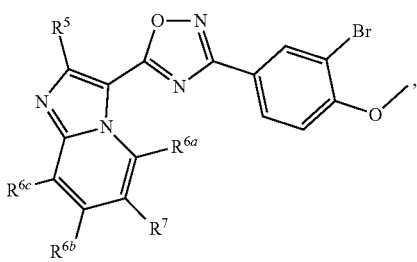

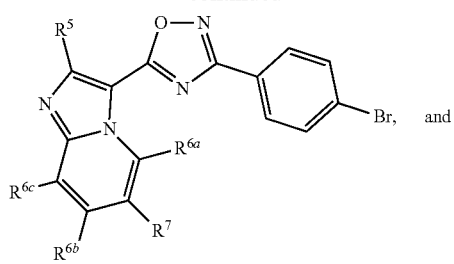

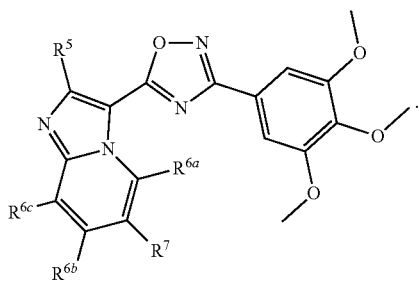

In a further aspect, the compound has a structure represented by a formula selected from:

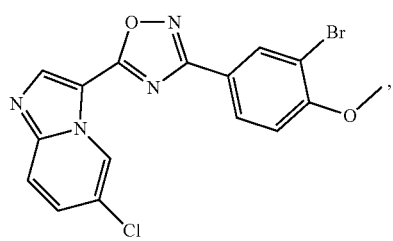

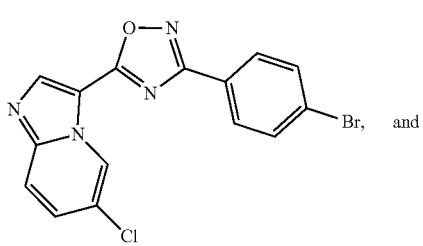

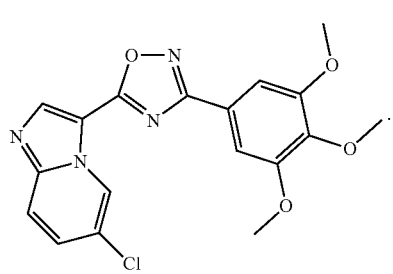

In a further aspect, the compound has a structure represented by a formula:

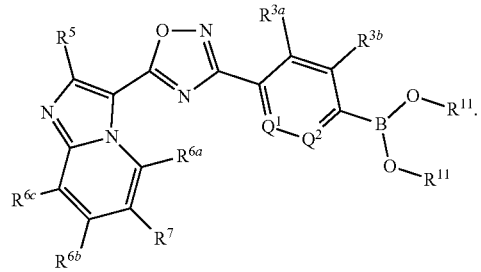

In a further aspect, the compound has a structure represented by a formula:

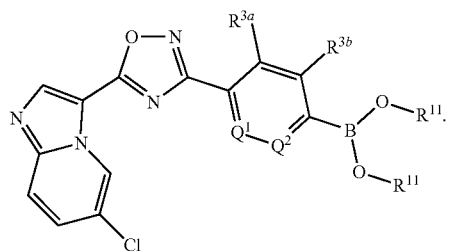

In a further aspect, the compound has a structure represented by a formula:

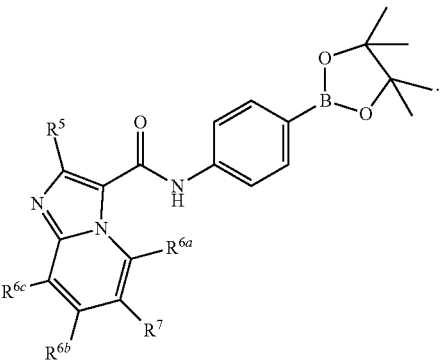

In a further aspect, the compound has a structure represented by formula:

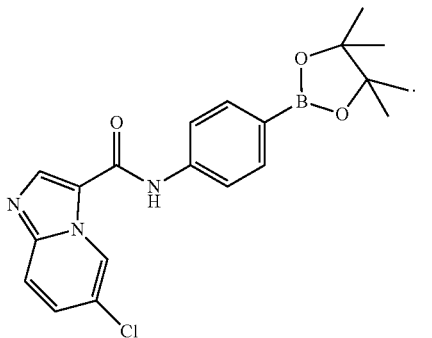 [SMILES: CC1(C)OB(c2ccc(NC(=O)c3cnc4ccc(Cl)cn34)cc2)OC1(C)C]

In a further aspect, the compound has a structure represented by a formula:
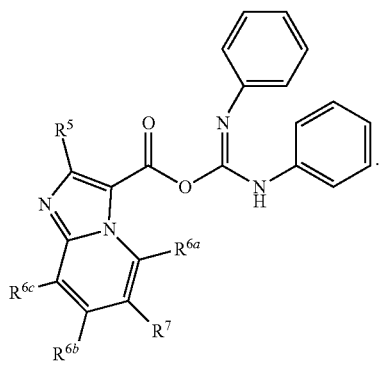
In a further aspect, the compound has a structure represented by a formula:
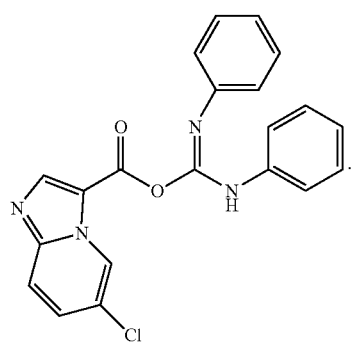 [SMILES: O=C(O/C(=N/c1ccccc1)Nc1ccccc1)c1cnc2ccc(Cl)cn12]
In a further aspect, the compound has a structure represented by a formula selected from:
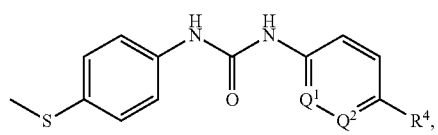
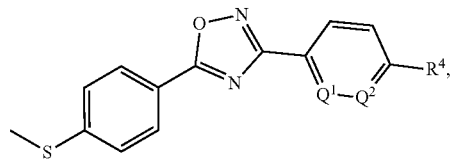
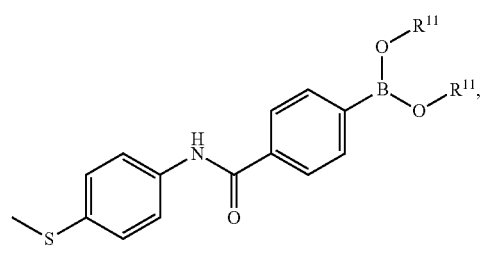
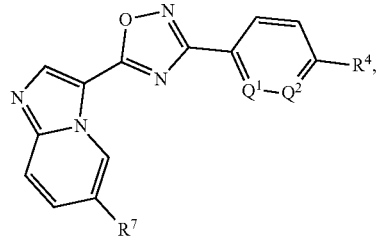
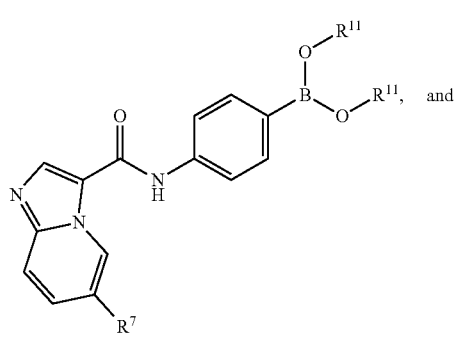
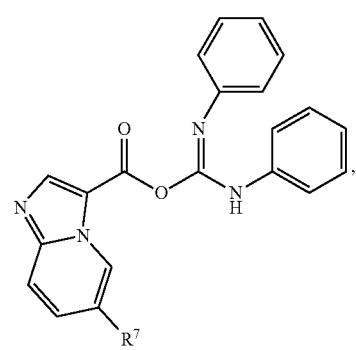
In a further aspect, the compound has a structure represented by a formula selected from:
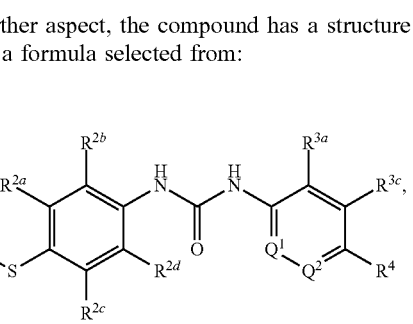
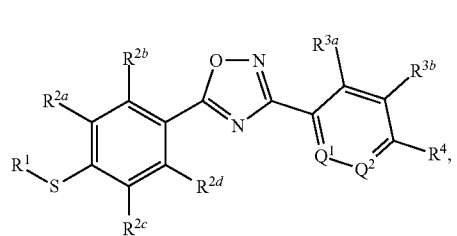

-continued

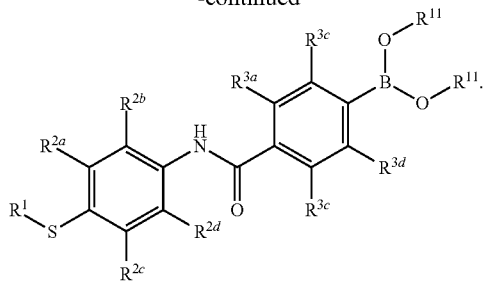

In a further aspect, R¹ is methyl. In a still further aspect, each of $R^{2a}$, $R^{2b}$, $R^{2c}$, $R^{2d}$, $R^{3a}$, and $R^{3b}$ is hydrogen. In yet a further aspect, $R^4$, when present, is —B(OR¹¹)₂.

In a further aspect, the compound has a structure represented by a formula:

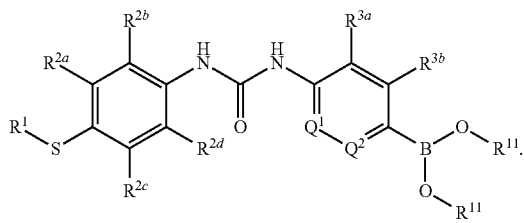

In a further aspect, the compound is selected from:

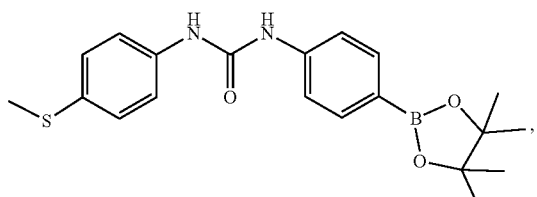

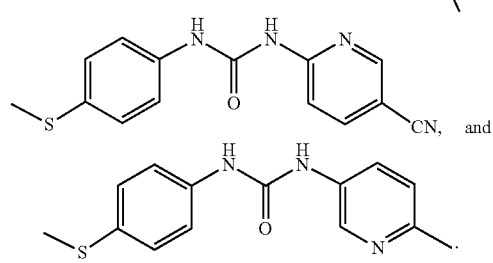

In a further aspect, the compound is:

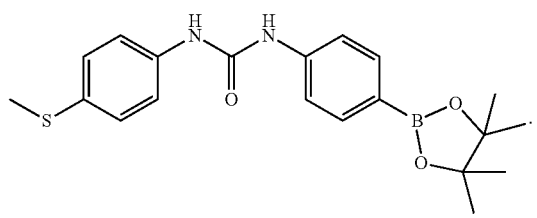

In a further aspect, the compound has a structure represented by a formula selected from:

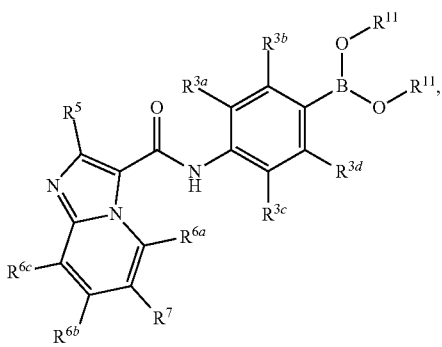

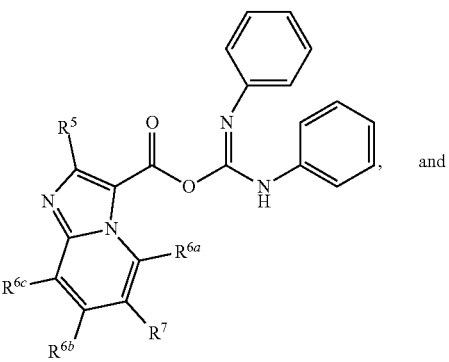

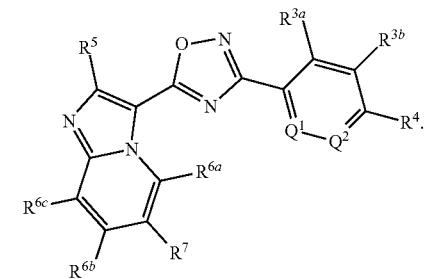

In a further aspect, each of $R^{3a}$ and $R^{3b}$, when present, is hydrogen. In a still further aspect, $R^4$, when present, is —B(OR¹¹)₂. In yet a further aspect, each of $R^5$, $R^{6a}$, $R^{6b}$ and $R^{6c}$ is hydrogen. In an even further aspect, $R^7$ is —Cl.

In a further aspect, the compound is selected from:

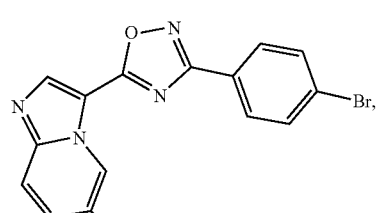

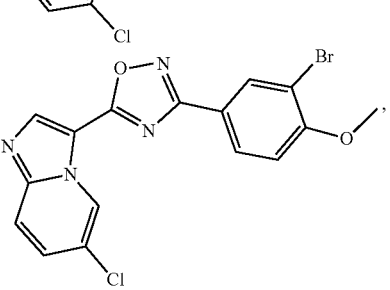

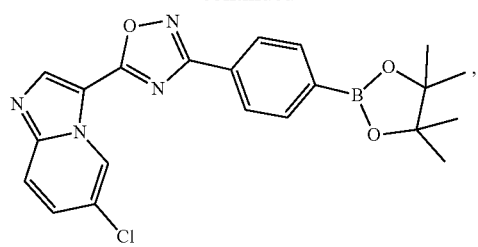
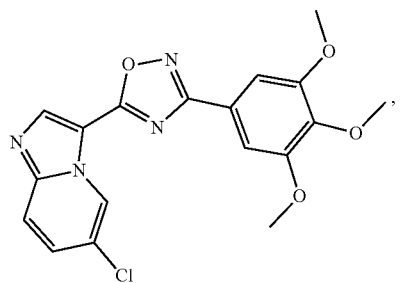
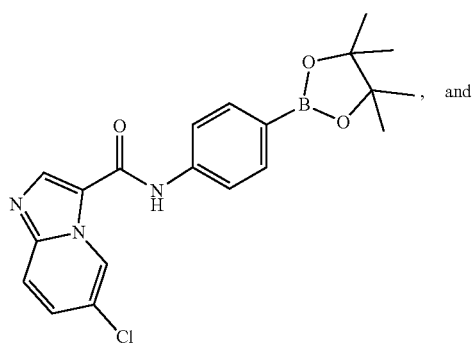
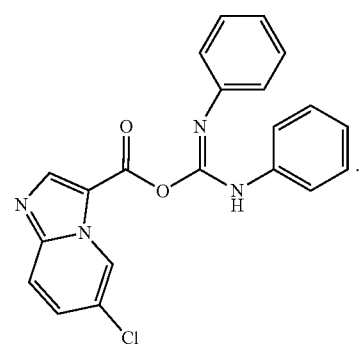
In a further aspect, the compound is selected from:
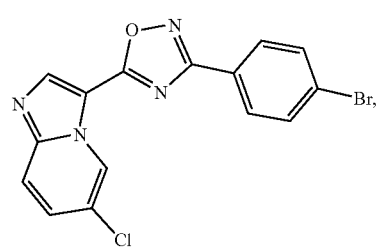
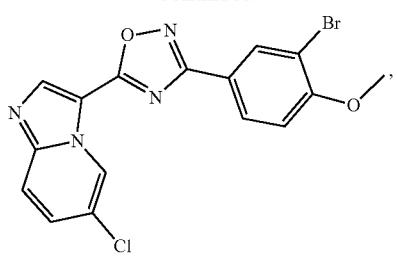
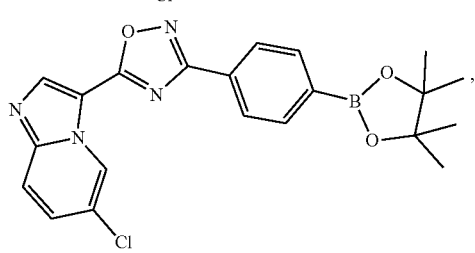
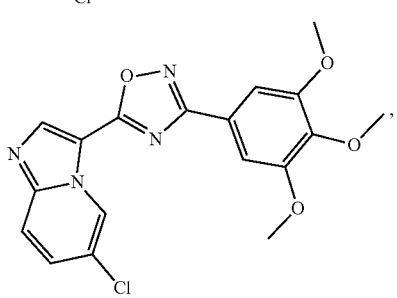
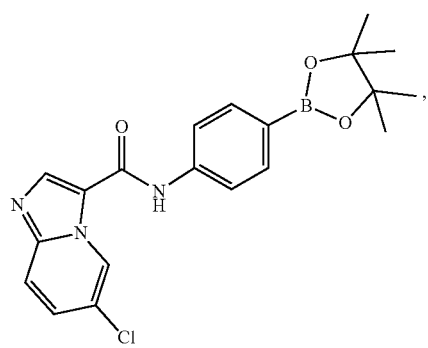
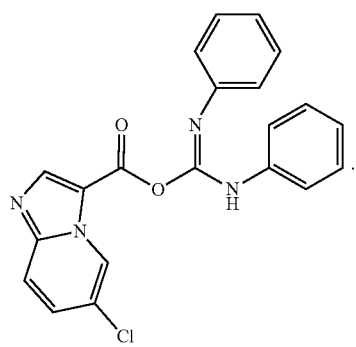
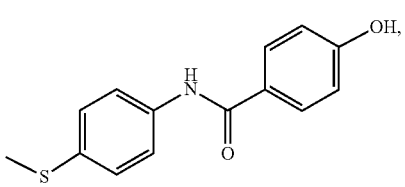

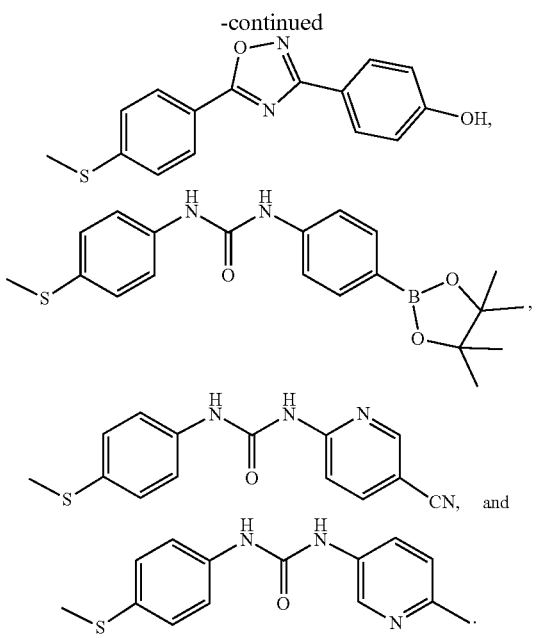

In a further aspect, the compound is:

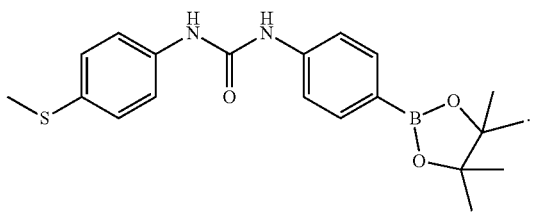

A. $Q^1$ and $Q^2$ Groups

In one aspect, each of $Q^1$ and $Q^2$, when present, is independently selected from N and $CR^{10}$. In a further aspect, one of $Q^1$ and $Q^2$, when present, is N, and one of $Q^1$ and $Q^2$, when present, is $CR^{10}$. In a still further aspect, each of $Q^1$ and $Q^2$, when present, is N. In yet a further aspect, each of $Q^1$ and $Q^2$, when present, is $CR^{10}$. In an even further aspect, each of $Q^1$ and $Q^2$, when present, is CH.

In a further aspect, $Q^1$, when present, is N, and $Q^2$, when present, is $CR^{10}$. In a still further aspect, $Q^1$, when present, is N, and $Q^2$, when present, is CH.

In a further aspect, $Q^1$, when present, is $CR^{10}$, and $Q^2$, when present, is N. In a still further aspect, $Q^1$, when present, is CH, and $Q^2$, when present, is N.

B. $Z^1$ and $Z^2$ Groups

In one aspect, $Z^1$, when present, is selected from N and $CR^{2b}$. In a further aspect, $Z^1$, when present, is N. In a still further aspect, $Z^1$, when present, is $CR^{2b}$.

In one aspect, $Z^2$, when present, is selected from N and $CR^{2c}$. In a further aspect, $Z^2$, when present, is N. In a still further aspect, $Z^2$, when present, is $CR^{2c}$.

In various aspects, $Z^1$, when present, is N, and $Z^2$, when present, is N. In a further aspect, $Z^1$, when present, is $CR^{2b}$, and $Z^2$, when present, is N. In a still further aspect, $Z^1$, when present, is N, and $Z^2$, when present, is $CR^{2c}$. In yet a further aspect, $Z^1$, when present, is $CR^{2b}$, and $Z^2$, when present, is $CR^{2c}$.

c. $R^1$ Groups

In one aspect, $R^1$, when present, is C1-C4 alkyl. In a further aspect, $R^1$, when present, is selected from methyl, ethyl, n-propyl, and isopropyl. In a still further aspect, $R^1$, when present, is selected from methyl and ethyl. In yet a further aspect, $R^1$, when present, is ethyl. In an even further aspect, $R^1$, when present, is methyl.

d. $R^{2a}$, $R^{2b}$, $R^{2c}$, $R^{2d}$, $R^{3a}$, and $R^{3b}$ Groups

In one aspect, each of $R^{2a}$, $R^{2b}$, $R^{2c}$, $R^{2d}$, $R^{3a}$, and $R^{3b}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, methyl, ethyl, n-propyl, isopropyl, ethenyl, n-propenyl, isopropenyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCF_3$, —$OCH_2CF_3$, —$OCH_2CH_2CF_3$, —$OCH(CH_3)CF_3$, —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In a still further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, methyl, ethyl, ethenyl, —$CH_2F$, —$CH_2Cl$, —$CH_2CH_2F$, —$CH_2CH_2Cl$, —$CH_2CN$, —$CH_2CH_2CN$, —$CH_2OH$, —$CH_2CH_2OH$, —$OCF_3$, —$OCH_2CF_3$, —$OCH_3$, —$OCH_2CH_3$, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In yet a further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, methyl, —$CH_2F$, —$CH_2Cl$, —$CH_2CN$, —$CH_2OH$, —$OCF_3$, —$OCH_3$, —$NHCH_3$, —$N(CH_3)_2$, and —$CH_2NH_2$.

In various aspects, each of $R^{2a}$, $R^{2b}$, $R^{2c}$, $R^{2d}$, $R^{3a}$, and $R^{3b}$, when present, is independently selected from hydrogen, halogen, —CN, —$NH_2$, —OH, —$NO_2$, C1-C4 alkyl, and C2-C4 alkenyl. In a further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, methyl, ethyl, n-propyl, isopropyl, ethenyl, n-propenyl, and isopropenyl. In a still further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, methyl, ethyl, and ethenyl. In yet a further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, and methyl.

In various aspects, each of $R^{2a}$, $R^{2b}$, $R^{2c}$, $R^{2d}$, $R^{3a}$, and $R^{3b}$, when present, is independently selected from hydrogen, halogen, —CN, —$NH_2$, —OH, —$NO_2$, C1-C4 haloalkyl, and C1-C4 cyanoalkyl. In a further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, and —$CH(CH_3)CH_2CN$. In a still further aspect, each of $R^{2a}$, $R^{2b}$, $R^{2c}$, $R^{2d}$, $R^{3a}$, and $R^{3b}$, when present, is independently selected from hydrogen, —F, —Cl, —CN, —$NH_2$, —OH, —$NO_2$, —$CH_2F$, —$CH_2Cl$, —CH$_2$CH$_2$F, —CH$_2$CH$_2$Cl, —CH$_2$CN, and —CH$_2$CH$_2$CN. In yet a further aspect, each of R$^{2a}$, R$^{2b}$, R$^{2c}$, R$^{2d}$, R$^{3a}$, and R$^{3b}$, when present, is independently selected from hydrogen, —F, —Cl, —CN, —NH$_2$, —OH, —NO$_2$, —CH$_2$F, —CH$_2$Cl, and —CH$_2$CN.

In various aspects, each of R$^{2a}$, R$^{2b}$, R$^{2c}$, R$^{2d}$, R$^{3a}$, and R$^{3b}$, when present, is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of R$^{2a}$, R$^{2b}$, R$^{2c}$, R$^{2a}$, R$^{3a}$, and R$^{3b}$, when present, is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, and —OCH(CH$_3$)CH$_3$. In a still further aspect, each of R$^{2a}$, R$^{2b}$, R$^{2c}$, R$^{2d}$, R$^{3a}$, and R$^{3b}$, when present, is independently selected from hydrogen, —F, —Cl, —CN, —NH$_2$, —OH, —NO$_2$, —CH$_2$OH, —CH$_2$CH$_2$OH, —OCF$_3$, —OCH$_2$CF$_3$, —OCH$_3$, and —OCH$_2$CH$_3$. In yet a further aspect, each of R$^{2a}$, R$^{2b}$, R$^{2c}$, R$^{2d}$, R$^{3a}$, and R$^{3b}$, when present, is independently selected from hydrogen, —F, —Cl, —CN, —NH$_2$, —OH, —NO$_2$, —CH$_2$OH, —OCF$_3$, and —OCH$_3$.

In various aspects, each of R$^{2a}$, R$^{2b}$, R$^{2c}$, R$^{2d}$, R$^{3a}$, and R$^{3b}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of R$^{2a}$, R$^{2b}$, R$^{2c}$, R$^{2a}$, R$^{3a}$, and R$^{3b}$, when present, is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{2a}$, R$^{2b}$, R$^{2c}$, R$^{2d}$, R$^{3a}$, and R$^{3b}$, when present, is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In yet a further aspect, each of R$^{2a}$, R$^{2b}$, R$^{2c}$, R$^{2d}$, R$^{3a}$, and R$^{3b}$, when present, is independently selected from hydrogen, —F, —Cl, —CN, —NH$_2$, —OH, —NO$_2$, —NHCH$_3$, —N(CH$_3$)$_2$, and —CH$_2$NH$_2$.

In a further aspect, each of R$^{2a}$, R$^{2b}$, R$^{2c}$, R$^{2d}$, R$^{3a}$, and R$^{3b}$, when present, is independently selected from hydrogen and C1-C4 alkyl. In a still further aspect, each of R$^{2a}$, R$^{2b}$, R$^{2c}$, R$^{2d}$, R$^{3a}$, and R$^{3b}$, when present, is independently selected from hydrogen, methyl, ethyl, n-propyl, and isopropyl. In yet a further aspect, each of R$^{2a}$, R$^{2b}$, R$^{2c}$, R$^{2d}$, R$^{3a}$, and R$^{3b}$, when present, is independently selected from hydrogen, methyl, and ethyl. In an even further aspect, each of R$^{2a}$, R$^{2b}$, R$^{2c}$, R$^{2d}$, R$^{3a}$, and R$^{3b}$, when present, is independently selected from hydrogen and ethyl. In a still further aspect, each of R$^{2a}$, R$^{2b}$, R$^{2c}$, R$^{2d}$, R$^{3a}$, and R$^{3b}$, when present, is independently selected from hydrogen and methyl.

In a further aspect, each of R$^{2a}$, R$^{2b}$, R$^{2c}$, R$^{2d}$, R$^{3a}$, and R$^{3b}$, when present, is independently selected from hydrogen and halogen. In a still further aspect, each of R$^{2a}$, R$^{2b}$, R$^{2c}$, R$^{2a}$, R$^{3a}$, and R$^{3b}$, when present, is independently selected from hydrogen, —F, —Cl, and —Br. In yet a further aspect, each of R$^{2a}$, R$^{2b}$, R$^{2c}$, R$^{2d}$, R$^{3a}$, and R$^{3b}$, when present, is independently selected from hydrogen, —F, and —Cl. In an even further aspect, each of R$^{2a}$, R$^{2b}$, R$^{2c}$, R$^{2a}$, R$^{3a}$, and R$^{3b}$, when present, is independently selected from hydrogen and —Cl. In a still further aspect, each of R$^{2a}$, R$^{2b}$, R$^{2c}$, R$^{2d}$, R$^{3a}$, and R$^{3b}$, when present, is independently selected from hydrogen and —F.

In a further aspect, each of R$^{2a}$, R$^{2b}$, R$^{2c}$, R$^{2d}$, R$^{3a}$, and R$^{3b}$, when present, is hydrogen.

e. R$^{3c}$ and R$^{3d}$ Groups

In one aspect, each of R$^{3c}$ and R$^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of R$^{3c}$ and R$^{3d}$, when present, is independently selected from hydrogen, —F, —Cl, —CN, —NH$_2$, —OH, —NO$_2$, methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{3c}$ and R$^{3d}$, when present, is independently selected from hydrogen, —F, —Cl, —CN, —NH$_2$, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In yet a further aspect, each of R$^{3c}$ and R$^{3d}$, when present, is independently selected from hydrogen, —F, —Cl, —CN, —NH$_2$, —OH, —NO$_2$, methyl, —CH$_2$F, —CH$_2$Cl, —CH$_2$CN, —CH$_2$OH, —OCF$_3$, —OCH$_3$, —NHCH$_3$, —N(CH$_3$)$_2$, and —CH$_2$NH$_2$.

In various aspects, each of R$^{3c}$ and R$^{3d}$, when present, is independently selected from hydrogen, halogen, —CN, —NH$_2$, —OH, —NO$_2$, C1-C4 alkyl, and C2-C4 alkenyl. In a further aspect, each of R$^{3c}$ and R$^{3d}$, when present, is independently selected from hydrogen, —F, —Cl, —CN, —NH$_2$, —OH, —NO$_2$, methyl, ethyl, n-propyl, isopropyl, ethenyl, n-propenyl, and isopropenyl. In a still further aspect, each of R$^{3c}$ and R$^{3d}$, when present, is independently selected from hydrogen, —F, —Cl, —CN, —NH$_2$, —OH, —NO$_2$, methyl, ethyl, and ethenyl. In yet a further aspect, each of R$^{3c}$ and R$^{3d}$, when present, is independently selected from hydrogen, —F, —Cl, —CN, —NH$_2$, —OH, —NO$_2$, and methyl.

In various aspects, each of R$^{3c}$ and R$^{3d}$, when present, is independently selected from hydrogen, halogen, —CN, —NH$_2$, —OH, —NO$_2$, C1-C4 haloalkyl, and C1-C4 cyanoalkyl. In a further aspect, each of R$^{3c}$ and R$^{3d}$, when present, is independently selected from hydrogen, —F, —Cl, —CN, —NH$_2$, —OH, —NO$_2$, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, and —CH(CH$_3$)CH$_2$CN. In a still further aspect, each of R$^{3c}$ and R$^{3d}$, when present, is independently selected from hydrogen, —F, —Cl, —CN, —NH$_2$, —OH, —NO$_2$, —CH$_2$F, —CH$_2$Cl, —CH$_2$CH$_2$F, —CH$_2$CH$_2$Cl, —CH$_2$CN, and —CH$_2$CH$_2$CN. In yet a further aspect, each of R$^{3c}$ and R$^{3d}$, when present, is independently selected from hydrogen, —F, —Cl, —CN, —NH$_2$, —OH, —NO$_2$, —CH$_2$F, —CH$_2$Cl, and —CH$_2$CN.

In various aspects, each of $R^{3c}$ and $R^{3d}$, when present, is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{3c}$ and $R^{3d}$, when present, is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, and —OCH(CH$_3$)CH$_3$. In a still further aspect, each of $R^{3c}$ and $R^{3d}$, when present, is independently selected from hydrogen, —F, —Cl, —CN, —NH$_2$, —OH, —NO$_2$, —CH$_2$OH, —CH$_2$CH$_2$OH, —OCF$_3$, —OCH$_2$CF$_3$, —OCH$_3$, and —OCH$_2$CH$_3$. In yet a further aspect, each of $R^{3c}$ and $R^{3d}$, when present, is independently selected from hydrogen, —F, —Cl, —CN, —NH$_2$, —OH, —NO$_2$, —CH$_2$OH, —OCF$_3$, and —OCH$_3$.

In various aspects, each of $R^{3c}$ and $R^{3d}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of $R^{3c}$ and $R^{3d}$, when present, is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{3c}$ and $R^{3d}$, when present, is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In yet a further aspect, each of $R^{3c}$ and $R^{3d}$, when present, is independently selected from hydrogen, —F, —Cl, —CN, —NH$_2$, —OH, —NO$_2$, —NHCH$_3$, —N(CH$_3$)$_2$, and —CH$_2$NH$_2$.

In a further aspect, each of $R^{3c}$ and $R^{3d}$, when present, is independently selected from hydrogen and C1-C4 alkyl. In a still further aspect, each of $R^{3c}$ and $R^{3d}$, when present, is independently selected from hydrogen, methyl, ethyl, n-propyl, and isopropyl. In yet a further aspect, each of $R^{3c}$ and $R^{3d}$, when present, is independently selected from hydrogen, methyl, and ethyl. In an even further aspect, each of $R^{3c}$ and $R^{3d}$, when present, is independently selected from hydrogen and ethyl. In a still further aspect, each of $R^{3c}$ and $R^{3d}$, when present, is independently selected from hydrogen and methyl.

In a further aspect, each of $R^{3c}$ and $R^{3d}$, when present, is independently selected from hydrogen and halogen. In a still further aspect, each of $R^{3c}$ and $R^{3d}$, when present, is independently selected from hydrogen, —F, —Cl, and —Br. In yet a further aspect, each of $R^{3c}$ and $R^{3d}$, when present, is independently selected from hydrogen, —F, and —Cl. In an even further aspect, each of $R^{3c}$ and $R^{3d}$, when present, is independently selected from hydrogen and —Cl. In a still further aspect, each of $R^{3c}$ and $R^{3d}$, when present, is independently selected from hydrogen and —F.

In a further aspect, each of $R^{3c}$ and $R^{3d}$, when present, is hydrogen.

f. $R^4$ Groups

In one aspect, $R^4$, when present, is independently selected from halogen, —CN, —OH, C1-C4 alkyl, C1-C4 alkoxy, —B(OR$^{11}$)$_2$, and —B(R$^{12}$)$_3$. In a further aspect, $R^4$, when present, is independently selected from —F, —Cl, —Br, —CN, —OH, methyl, ethyl, n-propyl, isopropyl, —OCH$_3$, —OCH$_2$CH$_3$, —OCH$_2$CH$_2$CH$_3$, —OCH(CH$_3$)CH$_3$, —B(OR$^{11}$)$_2$, and —B(R$^{12}$)$_3$. In a still further aspect, $R^4$, when present, is independently selected from —F, —Cl, —CN, —OH, methyl, ethyl, —OCH$_3$, —OCH$_2$CH$_3$, —B(OR$^{11}$)$_2$, and —B(R$^{12}$)$_3$. In yet a further aspect, $R^4$, when present, is independently selected from —F, —CN, —OH, methyl, —OCH$_3$, —B(OR$^{11}$)$_2$, and —B(R$^{12}$)$_3$.

In one aspect, $R^4$, when present, is independently selected from halogen, —CN, —OH, C1-C4 alkyl, C1-C4 alkoxy, and —B(OR$^{11}$)$_2$. In a further aspect, $R^4$, when present, is independently selected from —F, —Cl, —Br, —CN, —OH, methyl, ethyl, n-propyl, isopropyl, —OCH$_3$, —OCH$_2$CH$_3$, —OCH$_2$CH$_2$CH$_3$, —OCH(CH$_3$)CH$_3$, and —B(OR$^{11}$)$_2$. In a still further aspect, $R^4$, when present, is independently selected from —F, —Cl, —CN, —OH, methyl, ethyl, —OCH$_3$, —OCH$_2$CH$_3$, and —B(OR$^{11}$)$_2$. In yet a further aspect, $R^4$, when present, is independently selected from —F, —CN, —OH, methyl, —OCH$_3$, and —B(OR$^{11}$)$_2$.

In various aspects, $R^4$, when present, is independently selected from halogen, —CN, —OH, and —B(OR$^{11}$)$_2$. In a further aspect, $R^4$, when present, is independently selected from —F, —Cl, —Br, —CN, —OH, and —B(OR$^{11}$)$_2$. In a still further aspect, $R^4$, when present, is independently selected from —F, —Cl, —CN, —OH, and —B(OR$^{11}$)$_2$. In yet a further aspect, $R^4$, when present, is independently selected from —F, —CN, —OH, and —B(OR$^{11}$)$_2$.

In various aspects, $R^4$, when present, is independently selected from —CN, —OH, and —B(OR$^{11}$)$_2$. In a further aspect, $R^4$, when present, is independently selected from —CN and —OH. In a still further aspect, $R^4$, when present, is —CN. In yet a further aspect, $R^4$, when present, is —OH.

In various aspects, $R^4$, when present, is independently selected from halogen and —B(OR$^{11}$)$_2$. In a further aspect, $R^4$, when present, is independently selected from —F, —Cl, —Br, and —B(OR$^{11}$)$_2$. In a still further aspect, $R^4$, when present, is independently selected from —F, —Cl, and —B(OR$^{11}$)$_2$. In yet a further aspect, $R^4$, when present, is independently selected from —F and —B(OR$^{11}$)$_2$.

In various aspects, $R^4$, when present, is independently halogen. In a further aspect, $R^4$, when present, is independently selected from —F, —Cl, and —Br. In a still further aspect, $R^4$, when present, is independently selected from —F and —Cl. In yet a further aspect, $R^4$, when present, is —F.

In various aspects, $R^4$, when present, is independently selected from C1-C4 alkyl, C1-C4 alkoxy, and —B(OR$^{11}$)$_2$. In a further aspect, $R^4$, when present, is independently selected from methyl, ethyl, n-propyl, isopropyl, —OCH$_3$, —OCH$_2$CH$_3$, —OCH$_2$CH$_2$CH$_3$, —OCH(CH$_3$)CH$_3$, and —B(OR$^{11}$)$_2$. In a still further aspect, $R^4$, when present, is independently selected from methyl, ethyl, —OCH$_3$, —OCH$_2$CH$_3$, and —B(OR$^{11}$)$_2$. In yet a further aspect, $R^4$, when present, is independently selected from methyl, —OCH$_3$, and —B(OR)$_2$.

In various aspects, $R^4$, when present, is independently selected from C1-C4 alkyl. In a further aspect, $R^4$, when present, is independently selected from methyl, ethyl, n-propyl, and isopropyl. In a still further aspect, $R^4$, when present, is independently selected from methyl and ethyl. In yet a further aspect, $R^4$, when present, is methyl.

In various aspects, $R^4$, when present, is independently selected from C1-C4 alkoxy. In a further aspect, $R^4$, when present, is independently selected from —OCH$_3$, —OCH$_2$CH$_3$, —OCH$_2$CH$_2$CH$_3$, and —OCH(CH$_3$)CH$_3$. In a still further aspect, $R^4$, when present, is independently selected from —OCH$_3$ and —OCH$_2$CH$_3$. In yet a further aspect, $R^4$, when present, is —OCH$_3$.

In various aspects, $R^4$, when present, is independently selected from —$B(OR^{11})_2$ and —$B(R^{12})_3$. In a further aspect, $R^4$, when present, is —$B(OR^{11})_2$. In a still further aspect, $R^4$, when present, is —$B(OH)_2$. In yet a further aspect, $R^4$, when present, is —$B(R^{12})_3$.

In an even further aspect, $R^4$, when present, is —$BF_3$.

In a further aspect, $R^4$, when present, is a structure:

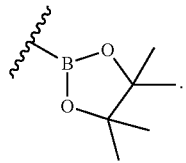 [SMILES: *B1OC(C)(C)C(C)(C)O1]

g. $R^5$, $R^{6a}$, $R^{6b}$, and $R^{6c}$ Groups

In one aspect, each of $R^5$, $R^{6a}$, $R^{6b}$, and $R^{6c}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^5$, $R^{6a}$, $R^{6b}$, and $R^{6c}$, when present, is independently selected from hydrogen, —F, —Cl, —CN, —$NH_2$, —OH, —$NO_2$, methyl, ethyl, n-propyl, isopropyl, ethenyl, n-propenyl, isopropenyl, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, —$CH(CH_3)CH_2CN$, —$CH_2OH$, —$CH_2CH_2OH$, —$CH_2CH_2CH_2OH$, —$CH(CH_3)CH_2OH$, —$OCF_3$, —$OCH_2CF_3$, —$OCH_2CH_2CF_3$, —$OCH(CH_3)CF_3$, —$OCH_3$, —$OCH_2CH_3$, —$OCH_2CH_2CH_3$, —$OCH(CH_3)CH_3$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In a still further aspect, each of $R^5$, $R^{6a}$, $R^{6b}$, and $R^{6c}$, when present, is independently selected from hydrogen, —F, —Cl, —CN, —$NH_2$, —OH, —$NO_2$, methyl, ethyl, ethenyl, —$CH_2F$, —$CH_2Cl$, —$CH_2CH_2F$, —$CH_2CH_2Cl$, —$CH_2CN$, —$CH_2CH_2CN$, —$CH_2OH$, —$CH_2CH_2OH$, —$OCF_3$, —$OCH_2CF_3$, —$OCH_3$, —$OCH_2CH_3$, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In yet a further aspect, each of $R^5$, $R^{6a}$, $R^{6b}$, and $R^{6c}$, when present, is independently selected from hydrogen, —F, —Cl, —CN, —$NH_2$, —OH, —$NO_2$, methyl, —$CH_2F$, —$CH_2Cl$, —$CH_2CN$, —$CH_2OH$, —$OCF_3$, —$OCH_3$, —$NHCH_3$, —$N(CH_3)_2$, and —$CH_2NH_2$.

In various aspects, each of $R^5$, $R^{6a}$, $R^{6b}$, and $R^{6c}$, when present, is independently selected from hydrogen, halogen, —CN, —$NH_2$, —OH, —$NO_2$, C1-C4 alkyl, and C2-C4 alkenyl. In a further aspect, each of $R^5$, $R^{6a}$, $R^{6b}$, and $R^{6c}$, when present, is independently selected from hydrogen, —F, —Cl, —CN, —$NH_2$, —OH, —$NO_2$, methyl, ethyl, n-propyl, isopropyl, ethenyl, n-propenyl, and isopropenyl. In a still further aspect, each of $R^5$, $R^{6a}$, $R^{6b}$, and $R^{6c}$, when present, is independently selected from hydrogen, —F, —Cl, —CN, —$NH_2$, —OH, —$NO_2$, methyl, ethyl, and ethenyl. In yet a further aspect, each of $R^5$, $R^{6a}$, $R^{6b}$, and $R^{6c}$, when present, is independently selected from hydrogen, —F, —Cl, —CN, —$NH_2$, —OH, —$NO_2$, and methyl.

In various aspects, each of $R^5$, $R^{6a}$, $R^{6b}$, and $R^{6c}$, when present, is independently selected from hydrogen, halogen, —CN, —$NH_2$, —OH, —$NO_2$, C1-C4 haloalkyl, and C1-C4 cyanoalkyl. In a further aspect, e each of $R^5$, $R^{6a}$, $R^{6b}$, and $R^{6c}$, when present, is independently selected from hydrogen, —F, —Cl, —CN, —$NH_2$, —OH, —$NO_2$, —$CH_2F$, —$CH_2Cl$, —$CH_2CH_2F$, —$CH_2CH_2Cl$, —$CH_2CH_2CH_2F$, —$CH_2CH_2CH_2Cl$, —$CH(CH_3)CH_2F$, —$CH(CH_3)CH_2Cl$, —$CH_2CN$, —$CH_2CH_2CN$, —$CH_2CH_2CH_2CN$, and —$CH(CH_3)CH_2CN$. In a still further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$CH_2F$, —$CH_2Cl$, —$CH_2CH_2F$, —$CH_2CH_2Cl$, —$CH_2CN$, and —$CH_2CH_2CN$. In yet a further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$CH_2F$, —$CH_2Cl$, and —$CH_2CN$.

In various aspects, each of $R^5$, $R^{6a}$, $R^{6b}$, and $R^{6c}$, when present, is independently selected from hydrogen, halogen, —CN, —$NH_2$, —OH, —$NO_2$, C1-C4 hydroxyalkyl, C1-C4 haloalkoxy, and C1-C4 alkoxy. In a further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$CH_2OH$, —$CH_2CH_2OH$, —$CH_2CH_2CH_2OH$, —$CH(CH_3)CH_2OH$, —$OCF_3$, —$OCH_2CF_3$, —$OCH_2CH_2CF_3$, —$OCH(CH_3)CF_3$, —$OCH_3$, —$OCH_2CH_3$, —$OCH_2CH_2CH_3$, and —$OCH(CH_3)CH_3$. In a still further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$CH_2OH$, —$CH_2CH_2OH$, —$OCF_3$, —$OCH_2CF_3$, —$OCH_3$, and —$OCH_2CH_3$. In yet a further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$CH_2OH$, —$OCF_3$, and —$OCH_3$.

In various aspects, each of $R^5$, $R^{6a}$, $R^{6b}$, and $R^{6c}$, when present, is independently selected from hydrogen, halogen, —CN, —$NH_2$, —OH, —$NO_2$, C1-C4 alkylamino, (C1-C4)(C1-C4) dialkylamino, and C1-C4 aminoalkyl. In a further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$NHCH_3$, —$NHCH_2CH_3$, —$NHCH_2CH_2CH_3$, —$NHCH(CH_3)CH_3$, —$N(CH_3)_2$, —$N(CH_2CH_3)_2$, —$N(CH_2CH_2CH_3)_2$, —$N(CH(CH_3)CH_3)_2$, —$N(CH_3)(CH_2CH_3)$, —$CH_2NH_2$, —$CH_2CH_2NH_2$, —$CH_2CH_2CH_2NH_2$, and —$CH(CH_3)CH_2NH_2$. In a still further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$NHCH_3$, —$NHCH_2CH_3$, —$N(CH_3)_2$, —$N(CH_2CH_3)_2$, —$N(CH_3)(CH_2CH_3)$, —$CH_2NH_2$, and —$CH_2CH_2NH_2$. In yet a further aspect, each of $R^5$, $R^{6a}$, $R^{6b}$, and $R^{6c}$, when present, is independently selected from hydrogen, —F, —Cl, —CN, —$NH_2$, —OH, —$NO_2$, —$NHCH_3$, —$N(CH_3)_2$, and —$CH_2NH_2$.

In a further aspect, each of $R^5$, $R^{6a}$, $R^{6b}$, and $R^{6c}$, when present, is independently selected from hydrogen and C1-C4 alkyl. In a still further aspect, each of $R^5$, $R^{6a}$, $R^{6b}$, and $R^{6c}$, when present, is independently selected from hydrogen, methyl, ethyl, n-propyl, and isopropyl. In yet a further aspect, each of $R^5$, $R^{6a}$, $R^{6b}$, and $R^{6c}$, when present, is independently selected from hydrogen, methyl, and ethyl. In an even further aspect, each of $R^5$, $R^{6a}$, $R^{6b}$, and $R^{6c}$, when present, is independently selected from hydrogen and ethyl. In a still further aspect, each of $R^5$, $R^{6a}$, $R^{6b}$, and $R^{6c}$, when present, is independently selected from hydrogen and methyl.

In a further aspect, each of $R^5$, $R^{6a}$, $R^{6b}$, and $R^{6c}$, when present, is independently selected from hydrogen and halogen. In a still further aspect, each of $R^5$, $R^{6a}$, $R^{6b}$, and $R^{6c}$, when present, is independently selected from hydrogen, —F, —Cl, and —Br. In yet a further aspect, each of $R^5$, $R^{6a}$, $R^{6b}$, and $R^{6c}$, when present, is independently selected from hydrogen, —F, and —Cl. In an even further aspect, each of $R^5$, $R^{6a}$, $R^{6b}$, and $R^{6c}$, when present, is independently selected from hydrogen and —Cl. In a still further aspect, each of $R^5$, $R^{6a}$, $R^{6b}$, and $R^{6c}$, when present, is independently selected from hydrogen and —F.

In a further aspect, each of $R^5$, $R^{6a}$, $R^{6b}$, and $R^{6c}$, when present, is hydrogen.

h. $R^7$ Groups

In one aspect, $R^7$, when present, is halogen. In a further aspect, $R^7$, when present, is selected from —F, —Cl, and —Br. In a still further aspect, $R^7$, when present, is selected from —F, —Cl, and —I. In yet a further aspect, $R^7$, when present, is selected from —F and —Cl. In an even further aspect, $R^7$, when present, is selected from —F and —Br. In a still further aspect, $R^7$, when present, is selected from —Br and —Cl. In yet a further aspect, $R^7$, when present, is selected from —F and —I. In an even further aspect, $R^7$, when present, is selected from —I and —Cl. In a still further aspect, $R^7$, when present, is selected from —I and —Br.

In a further aspect, $R^7$, when present, is —Cl. In a still further aspect, $R^7$, when present, is —Br. In yet a further aspect, $R^7$, when present, is —I. In an even further aspect, $R^7$, when present, is —F.

i. $R^8$ Groups

In one aspect, $R^8$, when present, is selected from —B(OR$^{11}$)$_2$ and —B(R$^{12}$)$_3$. In a further aspect, $R^8$, when present, is —B(OR$^{11}$)$_2$. In a still further aspect, $R^8$, when present, is —B(OH)$_2$. In yet a further aspect, $R^8$, when present, is —B(R$^{12}$)$_3$. In an even further aspect, $R^8$, when present, is —BF$_3$.

j. $R^{10}$ Groups

In one aspect, $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{10}$, when present, is selected from hydrogen, —F, —Cl, —CN, —NH$_2$, —OH, —NO$_2$, methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, $R^{10}$, when present, is selected from hydrogen, —F, —Cl, —CN, —NH$_2$, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In yet a further aspect, $R^{10}$, when present, is selected from hydrogen, —F, —Cl, —CN, —NH$_2$, —OH, —NO$_2$, methyl, —CH$_2$F, —CH$_2$Cl, —CH$_2$CN, —CH$_2$OH, —OCF$_3$, —OCH$_3$, —NHCH$_3$, —N(CH$_3$)$_2$, and —CH$_2$NH$_2$.

In various aspects, $R^{10}$, when present, is selected from hydrogen, halogen, —CN, —NH$_2$, —OH, —NO$_2$, C1-C4 alkyl, and C2-C4 alkenyl. In a further aspect, $R^{10}$, when present, is independently selected from hydrogen, —F, —Cl, —CN, —NH$_2$, —OH, —NO$_2$, methyl, ethyl, n-propyl, isopropyl, ethenyl, n-propenyl, and isopropenyl. In a still further aspect, $R^{10}$, when present, is independently selected from hydrogen, —F, —Cl, —CN, —NH$_2$, —OH, —NO$_2$, methyl, ethyl, and ethenyl. In yet a further aspect, $R^{10}$, when present, is selected from hydrogen, —F, —Cl, —CN, —NH$_2$, —OH, —NO$_2$, and methyl.

In various aspects, $R^{10}$, when present, is selected from hydrogen, halogen, —CN, —NH$_2$, —OH, —NO$_2$, C1-C4 haloalkyl, and C1-C4 cyanoalkyl. In a further aspect, $R^{10}$, when present, is selected from hydrogen, —F, —Cl, —CN, —NH$_2$, —OH, —NO$_2$, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, and —CH(CH$_3$)CH$_2$CN. In a still further aspect, $R^{10}$, when present, is selected from hydrogen, —F, —Cl, —CN, —NH$_2$, —OH, —NO$_2$, —CH$_2$F, —CH$_2$Cl, —CH$_2$CH$_2$F, —CH$_2$CH$_2$Cl, —CH$_2$CN, and —CH$_2$CH$_2$CN. In yet a further aspect, $R^{10}$, when present, is selected from hydrogen, —F, —Cl, —CN, —NH$_2$, —OH, —NO$_2$, —CH$_2$F, —CH$_2$Cl, and —CH$_2$CN.

In various aspects, $R^{10}$, when present, is selected from hydrogen, halogen, —CN, —NH$_2$, —OH, —NO$_2$, C1-C4 hydroxyalkyl, C1-C4 haloalkoxy, and C1-C4 alkoxy. In a further aspect, $R^{10}$, when present, is selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, and —OCH(CH$_3$)CH$_3$. In a still further aspect, $R^{10}$, when present, is selected from hydrogen, —F, —Cl, —CN, —NH$_2$, —OH, —NO$_2$, —CH$_2$OH, —CH$_2$CH$_2$OH, —OCF$_3$, —OCH$_2$CF$_3$, —OCH$_3$, and —OCH$_2$CH$_3$. In yet a further aspect, $R^{10}$, when present, is selected from hydrogen, —F, —Cl, —CN, —NH$_2$, —OH, —NO$_2$, —CH$_2$OH, —OCF$_3$, and —OCH$_3$.

In various aspects, $R^{10}$, when present, is selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, $R^{10}$, when present, is selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, $R^{10}$, when present, is selected from hydrogen, —F, —Cl, —CN, —NH$_2$, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In yet a further aspect, $R^{10}$, when present, is selected from hydrogen, —F, —Cl, —CN, —NH$_2$, —OH, —NO$_2$, —NHCH$_3$, —N(CH$_3$)$_2$, and —CH$_2$NH$_2$.

In a further aspect, $R^{10}$, when present, is selected from hydrogen and C1-C4 alkyl. In a still further aspect, $R^{10}$, when present, is selected from hydrogen, methyl, ethyl, n-propyl, and isopropyl. In yet a further aspect, $R^{10}$, when present, is selected from hydrogen, methyl, and ethyl. In an even further aspect, $R^{10}$, when present, is selected from hydrogen and ethyl. In a still further aspect, $R^{10}$, when present, is selected from hydrogen and methyl.

In a further aspect, $R^{10}$, when present, is selected from hydrogen and halogen. In a still further aspect, $R^{10}$, when present, is selected from hydrogen, —F, —Cl, and —Br. In yet a further aspect, $R^{10}$, when present, is selected from hydrogen, —F, and —Cl. In an even further aspect, $R^{10}$, when present, is selected from hydrogen and —Cl. In a still further aspect, $R^{10}$, when present, is selected from hydrogen and —F.

In a further aspect, $R^{10}$, when present, is hydrogen.

k. $R^{11}$ Groups

In one aspect, each occurrence of $R^{11}$, when present, is independently selected from hydrogen and C1-C8 alkyl, or each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups.

In a further aspect, each occurrence of $R^{11}$, when present, is independently selected from hydrogen and C1-C8 alkyl. In a still further aspect, each occurrence of $R^D$, when present, is independently selected from hydrogen and C1-C4 alkyl. In yet a further aspect, each occurrence of $R^{11}$, when present, is independently selected from hydrogen, methyl, ethyl, n-propyl, and isopropyl. In an even further aspect, each occurrence of $R^{11}$, when present, is independently selected from hydrogen, methyl, and ethyl. In a still further aspect, each occurrence of $R^{11}$, when present, is independently selected from hydrogen and ethyl. In yet a further aspect, each occurrence of $R^{11}$, when present, is independently selected from hydrogen and methyl.

In a further aspect, each occurrence of $R^{11}$, when present, is C1-C8 alkyl. In a still further aspect, each occurrence of $R^{11}$, when present, is C1-C4 alkyl. In yet a further aspect, each occurrence of $R^{11}$, when present, is selected from methyl, ethyl, n-propyl, and isopropyl. In an even further aspect, each occurrence of $R^{11}$, when present, is selected from methyl and ethyl. In a still further aspect, each occurrence of $R^{11}$, when present, is ethyl. In yet a further aspect, each occurrence of $R^{11}$, when present, is methyl.

In a further aspect, each occurrence of $R^{11}$, when present, is hydrogen.

In a further aspect, each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups. In a still further aspect, $R^{11}$, when present, is covalently bonded together, and, together with the intermediate atoms, comprise a C6 bicyclic heterocycle or a C2-C3 heterocycloalkyl, and is substituted with 0, 1, 2, or 3 C1-C4 alkyl groups. In yet a further aspect, $R^{11}$, when present, is covalently bonded together, and, together with the intermediate atoms, comprise a C6 bicyclic heterocycle or a C2-C3 heterocycloalkyl, and is substituted with 0, 1, or 2 C1-C4 alkyl groups. In an even further aspect, $R^{11}$, when present, is covalently bonded together, and, together with the intermediate atoms, comprise a C6 bicyclic heterocycle or a C2-C3 heterocycloalkyl, and is substituted with 0 or 1 C1-C4 alkyl groups. In a still further aspect, $R^{11}$, when present, is covalently bonded together, and, together with the intermediate atoms, comprise a C6 bicyclic heterocycle or a C2-C3 heterocycloalkyl, and is monosubstituted with a C1-C4 alkyl group. In yet a further aspect, $R^{11}$, when present, is covalently bonded together, and, together with the intermediate atoms, comprise a C6 bicyclic heterocycle or a C2-C3 heterocycloalkyl, and is unsubstituted.

In a further aspect, each occurrence of $R^{11}$, when present, is covalently bonded together, and, together with the intermediate atoms, comprise a C6 bicyclic heterocycle substituted with 0, 1, 2, 3, or 4 C1-C4 alkyl groups. In a still further aspect, $R^{11}$, when present, is covalently bonded together, and, together with the intermediate atoms, comprise a C6 bicyclic heterocycle substituted with 0, 1, 2, or 3 C1-C4 alkyl groups. In yet a further aspect, $R^{11}$, when present, is covalently bonded together, and, together with the intermediate atoms, comprise a C6 bicyclic heterocycle substituted with 0, 1, or 2 C1-C4 alkyl groups. In an even further aspect, $R^{11}$, when present, is covalently bonded together, and, together with the intermediate atoms, comprise a C6 bicyclic heterocycle substituted with 0 or 1 C1-C4 alkyl groups. In a still further aspect, $R^{11}$, when present, is covalently bonded together, and, together with the intermediate atoms, comprise a C6 bicyclic heterocycle monosubstituted with a C1-C4 alkyl group. In yet a further aspect, $R^{11}$, when present, is covalently bonded together, and, together with the intermediate atoms, comprise an unsubstituted C6 bicyclic heterocycle.

In a further aspect, $R^{11}$, when present, is covalently bonded together, and, together with the intermediate atoms, comprise a C6 bicyclic heterocycle substituted with 4 C1-C4 alkyl groups. In a still further aspect, $R^{11}$, when present, is covalently bonded together, and, together with the intermediate atoms, comprise a C6 bicyclic heterocycle substituted with 4 groups selected from methyl, ethyl, n-propyl, and isopropyl. In yet a further aspect, $R^{11}$, when present, is covalently bonded together, and, together with the intermediate atoms, comprise a C6 bicyclic heterocycle substituted with 4 groups selected from methyl and ethyl. In an even further aspect, $R^{11}$, when present, is covalently bonded together, and, together with the intermediate atoms, comprise a C6 bicyclic heterocycle substituted with 4 methyl groups.

In a further aspect, each occurrence of $R^{11}$, when present, is covalently bonded together, and, together with the intermediate atoms, comprise a C2-C3 heterocycloalkyl substituted with 0, 1, 2, 3, or 4 C1-C4 alkyl groups. In a still further aspect, $R^{11}$, when present, is covalently bonded together, and, together with the intermediate atoms, comprise a C2-C3 heterocycloalkyl substituted with 0, 1, 2, or 3 C1-C4 alkyl groups. In yet a further aspect, $R^{11}$, when present, is covalently bonded together, and, together with the intermediate atoms, comprise a C2-C3 heterocycloalkyl substituted with 0, 1, or 2 C1-C4 alkyl groups. In an even further aspect, $R^{11}$, when present, is covalently bonded together, and, together with the intermediate atoms, comprise a C2-C3 heterocycloalkyl substituted with 0 or 1 C1-C4 alkyl groups. In a still further aspect, $R^{11}$, when present, is covalently bonded together, and, together with the intermediate atoms, comprise a C2-C3 heterocycloalkyl monosubstituted with a C1-C4 alkyl group. In yet a further aspect, $R^{11}$, when present, is covalently bonded together, and, together with the intermediate atoms, comprise an unsubstituted C2-C3 heterocycloalkyl.

In a further aspect, $R^{11}$, when present, is covalently bonded together, and, together with the intermediate atoms, comprise a C2-C3 heterocycloalkyl substituted with 4 C1-C4 alkyl groups. In a still further aspect, $R^{11}$, when present, is covalently bonded together, and, together with the intermediate atoms, comprise a C2-C3 heterocycloalkyl substituted with 4 groups selected from methyl, ethyl, n-propyl, and isopropyl. In yet a further aspect, $R^{11}$, when present, is covalently bonded together, and, together with the intermediate atoms, comprise a C2-C3 heterocycloalkyl substituted with 4 groups selected from methyl and ethyl. In an even further aspect, $R^{11}$, when present, is covalently bonded together, and, together with the intermediate atoms, comprise a C2-C3 heterocycloalkyl substituted with 4 methyl groups.

1. R[12] Groups

In one aspect, each occurrence of R[12], when present, is independently halogen. In a further aspect, each occurrence of R[12], when present, is independently selected from —F, —Cl, and —I. In a still further aspect, each occurrence of R[12], when present, is independently selected from —F and —Cl. In yet a further aspect, each occurrence of R[12], when present, is —Cl. In an even further aspect, each occurrence of R[12], when present, is —F.

2. Example Compounds

In one aspect, a compound can be present as one or more of the following structures:

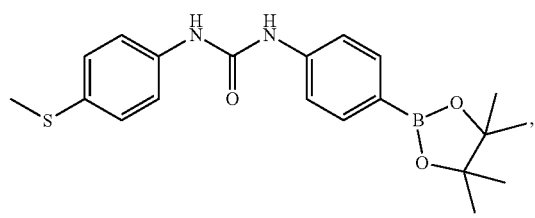

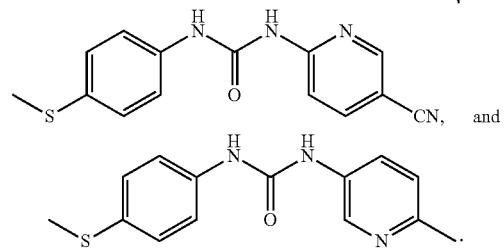

or a pharmaceutically acceptable salt thereof.

In one aspect, a compound can be present as one or more of the following structures:

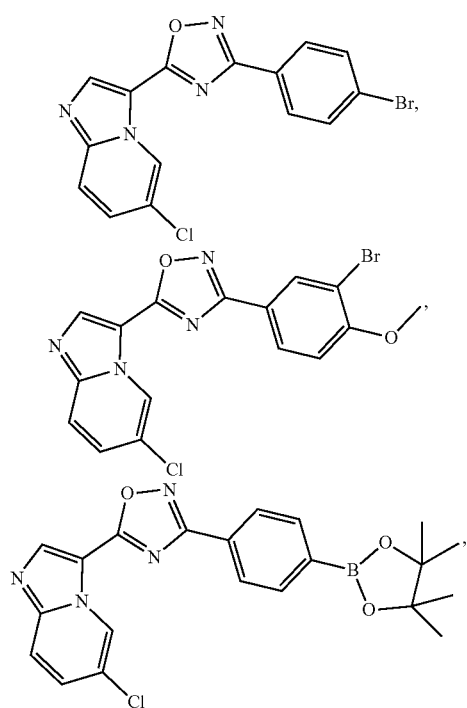

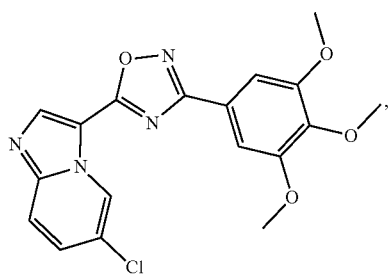

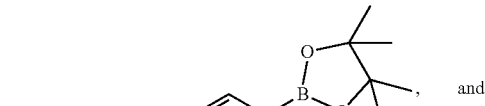

and

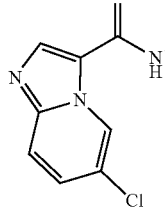

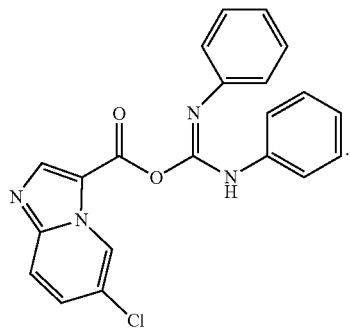

or a pharmaceutically acceptable salt thereof.

In one aspect, a compound can be present as one or more of the following structures.

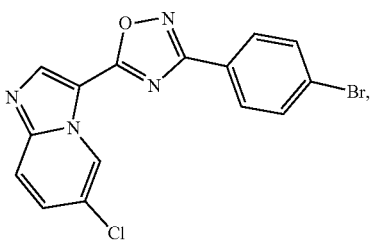

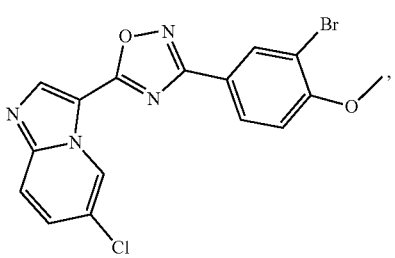

81

-continued

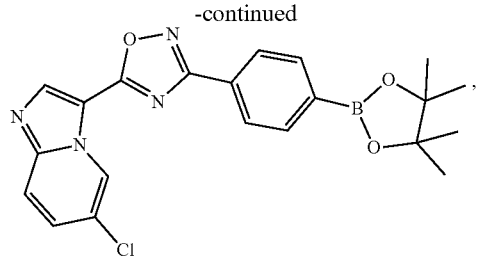

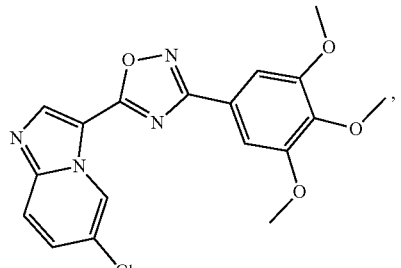

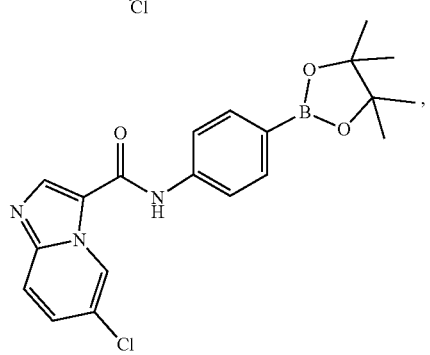

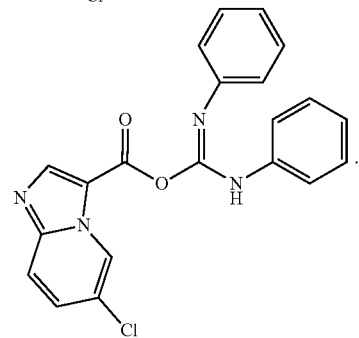

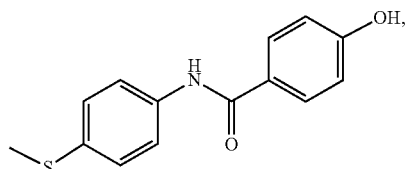

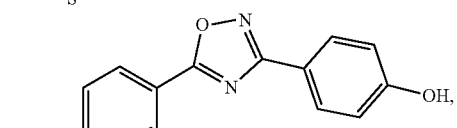

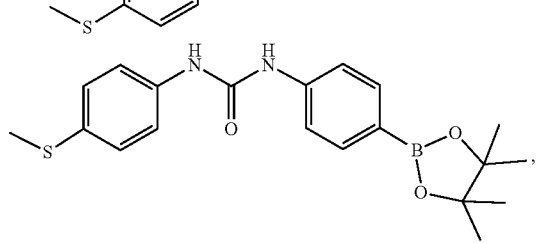

82

-continued

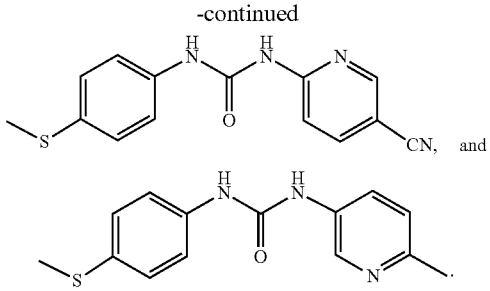

or a pharmaceutically acceptable salt thereof.

C. PHARMACEUTICAL COMPOSITIONS

In one aspect, disclosed are pharmaceutical compositions comprising an effective amount of a disclosed compound and a pharmaceutically acceptable carrier.

Thus, in one aspect, disclosed are pharmaceutical compositions comprising an effective amount of a compound having a structure represented by a formula selected from:

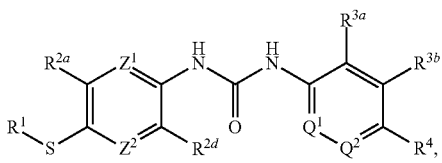

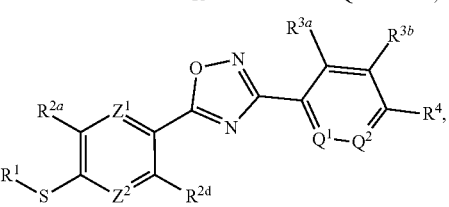

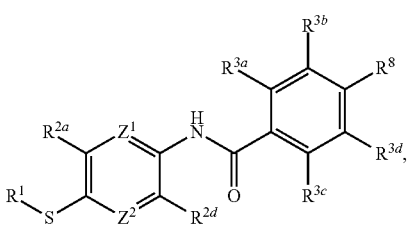

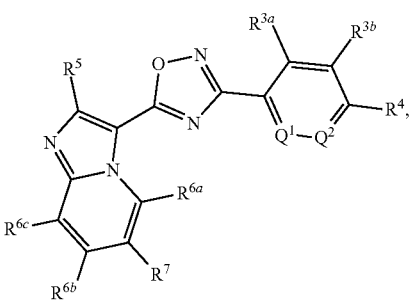

-continued

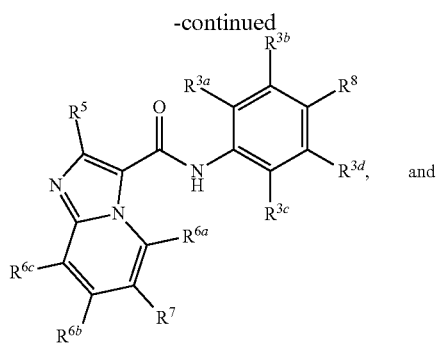

and

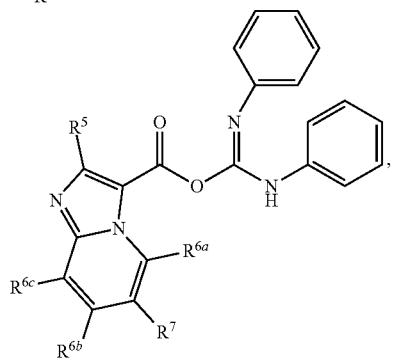

wherein each of $Q^1$ and $Q^2$, when present, is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$, when present, is independently selected from halogen, —CN, —OH, C1-C4 alkyl, C1-C4 alkoxy, —B(OR$^{11}$)$_2$, and —B(R$^{12}$)$_3$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —B(OR$^{11}$)$_2$ and —B(R$^{12}$)$_3$, provided that when the compound has a structure represented by a formula:

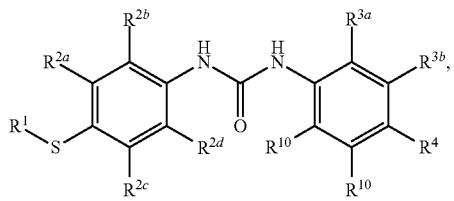

then $R^4$ is —B(OR$^{11}$)$_2$, provided that when the compound has a structure represented by a formula:

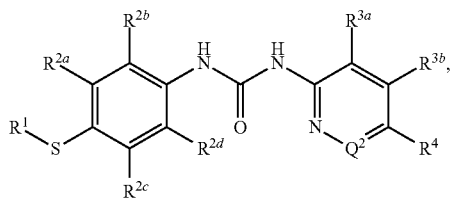

then $R^4$ is not halogen, and provided that when the compound has a structure represented by a formula:

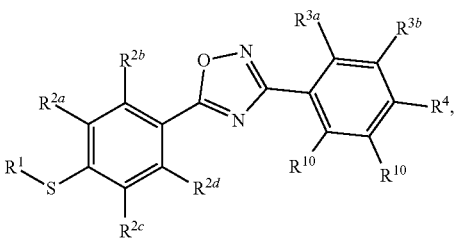

then $R^4$ is not —OH, or a pharmaceutically acceptable salt thereof, and a pharmaceutically acceptable carrier.

Also disclosed are pharmaceutical compositions comprising an effective amount of a compound having a structure represented by a formula selected from:

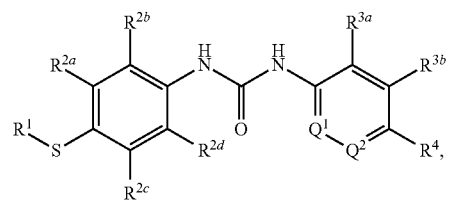

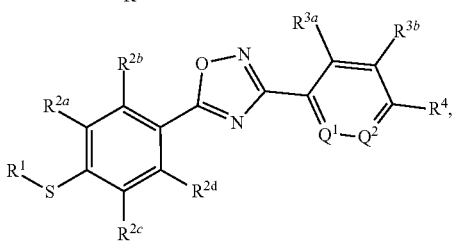

-continued

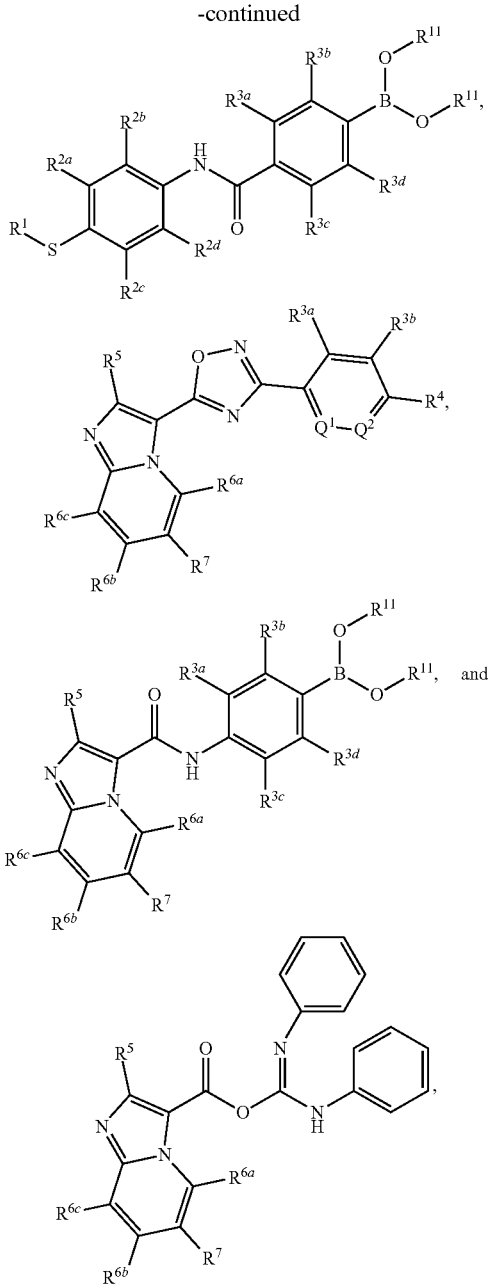

wherein each of $Q^1$ and $Q^2$, when present, is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$, when present, is independently selected from halogen, —CN, —OH, C1-C4 alkyl, C1-C4 alkoxy, and —B(OR$^{11}$)$_2$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^7$, when present, is halogen, provided that when the compound has a structure represented by a formula:

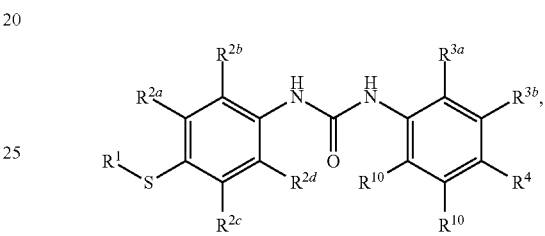

then $R^4$ is —B(OR$^{11}$)$_2$, provided that when the compound has a structure represented by a formula:

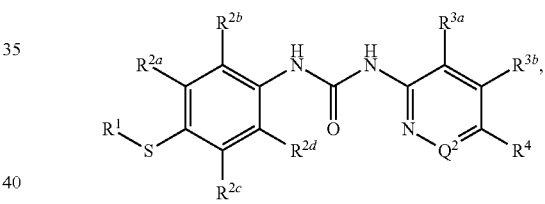

then $R^4$ is not halogen, and provided that when the compound has a structure represented by a formula:

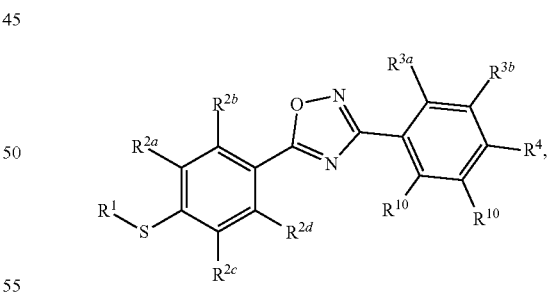

then $R^4$ is not —OH, or a pharmaceutically acceptable salt thereof, and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with KLF15 signaling dysfunction such as, for example, kidney disease (e.g., chronic kidney disease), heart disease, obesity, and neurodegenerative disorders (e.g., ALS, Alzheimer's disease, Parkinson's disease, spinal muscular atrophy, traumatic brain injury, vascular dementia, Huntington's disease, mental retardation, and ADHD).

In various aspects, the composition is a solid dosage form. In a further aspect, the composition is an oral solid dosage form. In a still further aspect, the solid dosage form is a tablet. In yet a further aspect, the solid dosage form is a capsule.

It is understood that the disclosed compositions can be prepared from the disclosed compounds. It is also understood that the disclosed compositions can be employed in the disclosed methods of using.

D. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-III, as described and exemplified below. The following examples are provided so that the invention might be more fully understood, are illustrative only, and should not be construed as limiting.

1. Route I

In one aspect, substituted small molecule KLF15 agonists can be prepared as shown below.

SCHEME 1A.

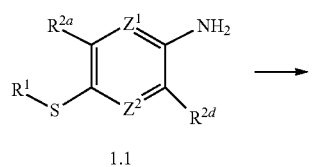

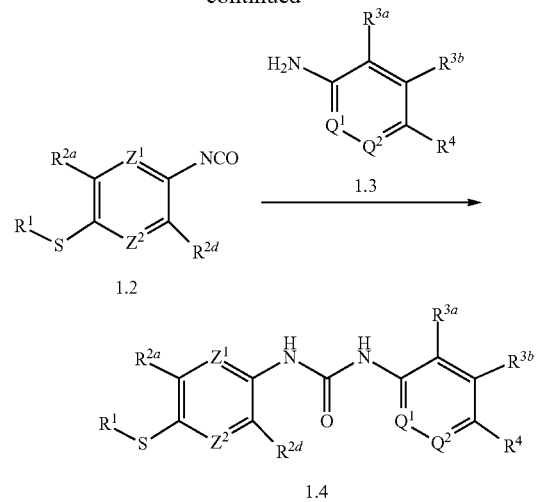

Compounds are represented in generic form, with substituents as noted in compound descriptions elsewhere herein. A more specific example is set forth below.

SCHEME 1B.

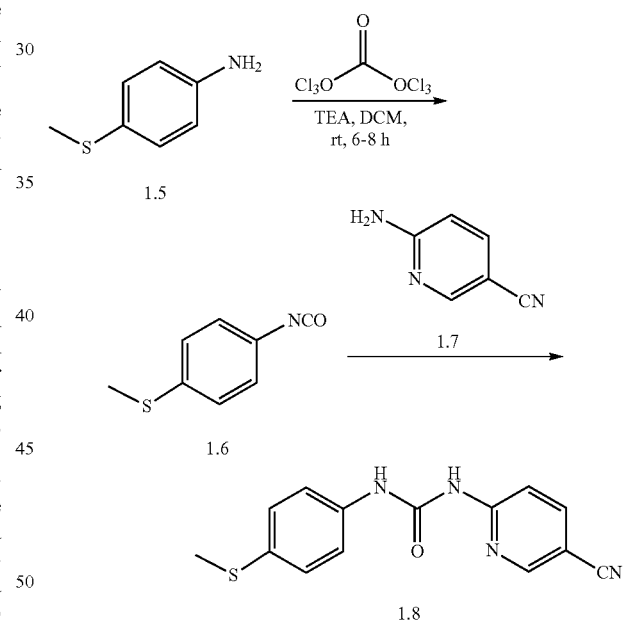

In one aspect, compounds of type 1.8 and similar compounds can be prepared according to reaction Scheme 1B above. Thus, compounds of type 1.6 can be prepared by reacting an appropriate aryl amine, e.g., 1.5 as shown above, with an appropriate electrophilic compound, e.g., $2\lambda^3$-trichloran-2-yl trichloro-$\lambda^4$-oxidanecarboxylate as shown above. Appropriate amines and appropriate electrophilic compounds are commercially available or prepared by methods known to one skilled in the art. The reaction is carried out in the presence of an appropriate base, e.g., triethylamine, in an appropriate solvent, e.g., dichloromethane, for an appropriate period of time, e.g., 6 to 8 hours. Compounds of type 1.8 can be prepared by coupling an appropriate isothiocyanate, e.g., 1.6 as shown above, and an appropriate amine, e.g., 1.7 as shown above. The coupling reaction is carried out in the presence of an appropriate solvent, e.g., dichloromethane, for an appropriate period of time, e.g., 20 hours. As can be appreciated by one skilled in the art, the above reaction provides an example of a generalized approach wherein compounds similar in structure to the specific reactants above (compounds similar to compounds of type 1.1, 1.2, and 1.3) can be substituted in the reaction to provide substituted small molecule KLF15 agonists similar to Formula 1.4.

2. Route II

In one aspect, substituted small molecule KLF15 agonists can be prepared as shown below.

SCHEME 2A.

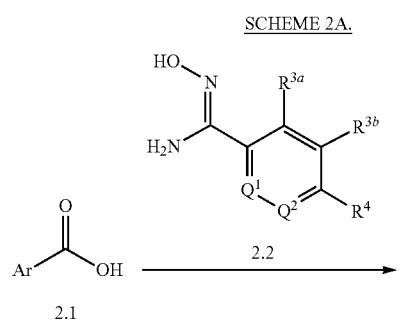

2.1      2.2

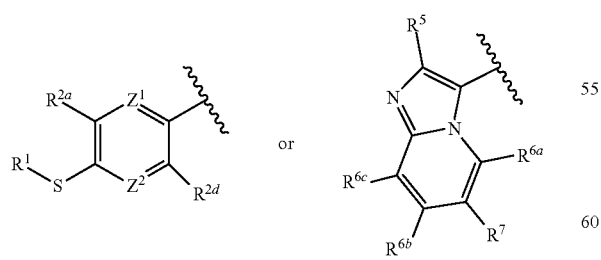

2.3

Compounds are represented in generic form, where Ar is and with other substituents as noted in compound descriptions elsewhere herein. A more specific example is set forth below.

SCHEME 2B.

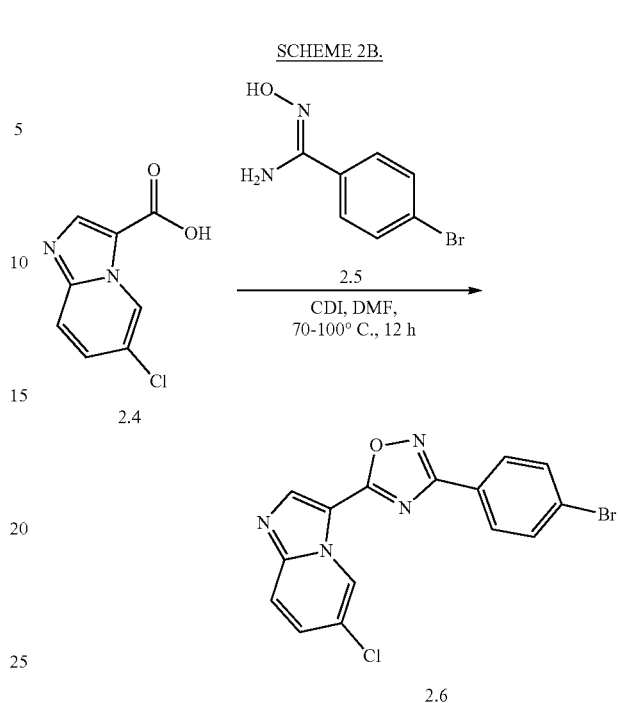

In one aspect, compounds of type 2.6 and similar compounds can be prepared according to reaction Scheme 2B above. Thus, compounds of type 2.6 can be prepared by coupling an appropriate carboxylic acid, e.g., 2.4 as shown above, with an appropriate N-hydroxyimine, e.g., 2.5 as shown above. Appropriate carboxylic acids and appropriate N-hydroxyimines are commercially available or prepared by methods known to one skilled in the art. The coupling reaction is carried out in the presence of an appropriate coupling agent, e.g., 1'-carbonyldiimidazole (CDI), in an appropriate solvent, e.g., dimethylformamide, at an appropriate temperature, e.g., 70 to 100° C., for an appropriate period of time, e.g., 12 hours. As can be appreciated by one skilled in the art, the above reaction provides an example of a generalized approach wherein compounds similar in structure to the specific reactants above (compounds similar to compounds of type 2.1 and 2.2) can be substituted in the reaction to provide substituted small molecule KLF15 agonists similar to Formula 2.3.

3. Route III

In one aspect, substituted small molecule KLF15 agonists can be prepared as shown below.

SCHEME 3A.

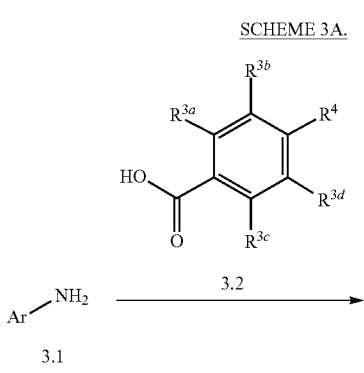

3.1

-continued

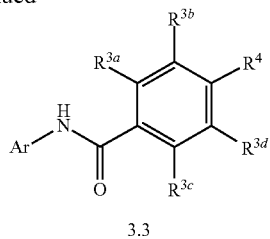

3.3

Compounds are represented in generic form, where Ar is

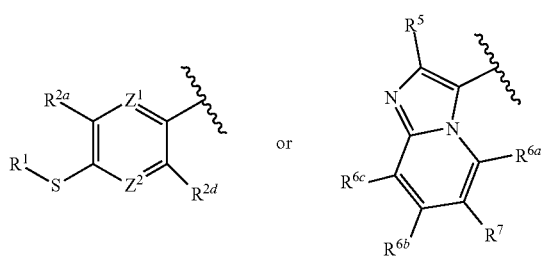

and with other substituents as noted in compound descriptions elsewhere herein. A more specific example is set forth below.

SCHEME 3B.

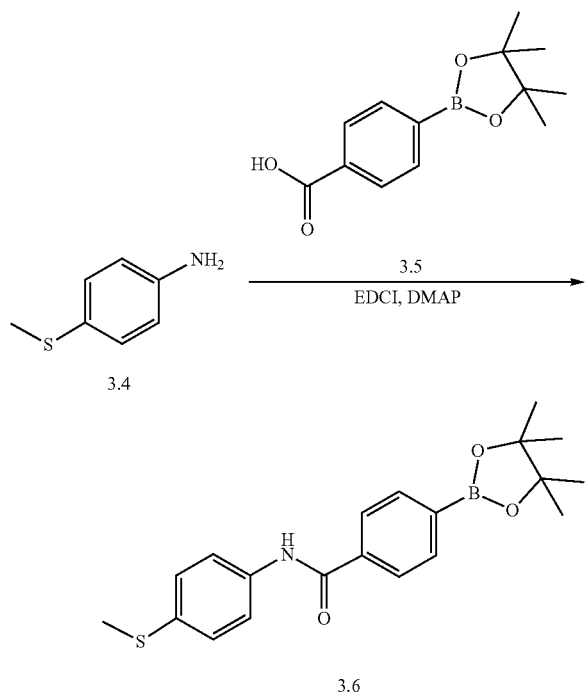

In one aspect, compounds of type 3.6 and similar compounds can be prepared according to reaction Scheme 3B above. Thus, compounds of type 3.6 can be prepared by coupling an appropriate amine, e.g., 3.4 as shown above, with an appropriate carboxylic acid, e.g., 3.5 as shown above. Appropriate amines and appropriate carboxylic acids are commercially available or prepared by methods known to one skilled in the art. The coupling reaction is carried out in the presence of an appropriate coupling agent, e.g., 1-ethyl-3-(3-dimethylaminopropyl)carbodiimide (EDCI), and an appropriate activating agent, e.g., 4-dimethylaminopyridine (DMAP). As can be appreciated by one skilled in the art, the above reaction provides an example of a generalized approach wherein compounds similar in structure to the specific reactants above (compounds similar to compounds of type 3.1 and 3.2) can be substituted in the reaction to provide substituted small molecule KLF15 agonists similar to Formula 3.3.

E. METHODS OF USING THE COMPOUNDS

The compounds and pharmaceutical compositions of the invention are useful in treating or controlling disorders associated with Krüppel-Like Factor 15 (KLF15) signaling dysfunction such as, for example, kidney disease (e.g., chronic kidney disease), heart disease, obesity, and neurodegenerative disorders (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)). To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a disorder associated with Krüppel-Like Factor 15 (KLF15) signaling dysfunction such as, for example, kidney disease (e.g., chronic kidney disease), heart disease, obesity, and neurodegenerative disorders (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)).

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disorder associated with Krüppel-Like Factor 15 (KLF15) signaling dysfunction such as, for example, kidney disease (e.g., chronic kidney disease), heart disease, obesity, and neurodegenerative disorders (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)).

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with Krüppel-Like Factor 15 (KLF15) signaling dysfunction such as, for example, kidney disease (e.g., chronic kidney disease), heart disease, obesity, and neurodegenerative disorders (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)). Thus, provided is a method comprising administering a therapeutically effective amount of a disclosed compound to a subject. In a further aspect, the method can be a method for treating a disorder associated with KLF15 signaling dysfunction.

a. Treating a Disorder Associated with KLF15 Signaling Dysfunction

In one aspect, disclosed are methods of treating a disorder associated with KLF15 signaling dysfunction in a subject in need thereof, the method comprising the step of administering to the subject a therapeutically effective amount of at least one disclosed compound, or a pharmaceutically acceptable salt thereof.

In one aspect, disclosed are methods for treating a disorder associated with Krüppel-Like Factor 15 (KLF15) signaling dysfunction in a subject in need thereof, the method comprising administering to the subject an effective amount of a compound having a structure represented by a formula selected from:

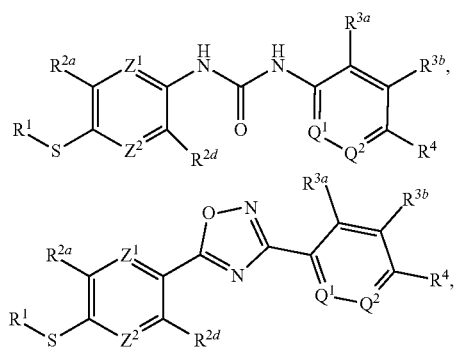

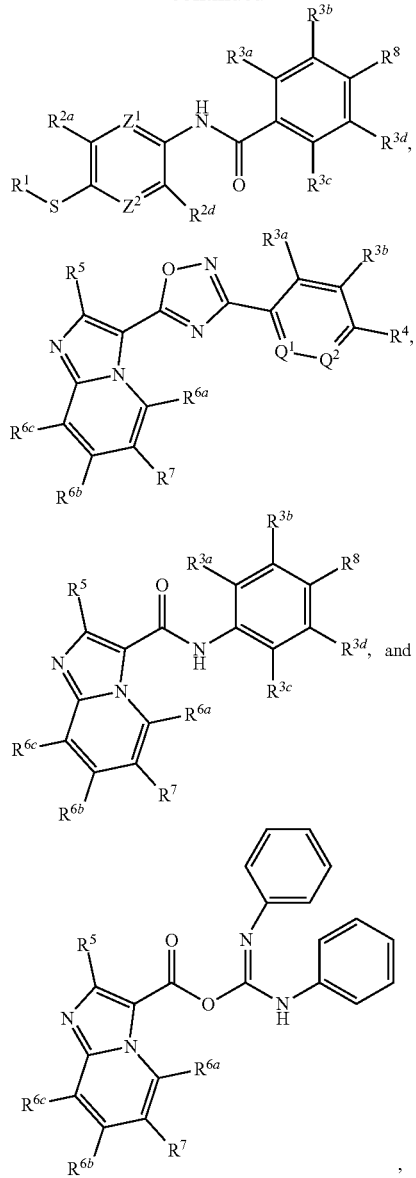

wherein each of $Q^1$ and $Q^2$ is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is independently selected from halogen, —CN, —OH, C1-C4 alkyl, C1-C4 alkoxy, —B(OR¹¹)₂, and —B(R¹²)₃; wherein each occurrence of R¹¹, when present, is independently selected from hydrogen and C1-C8 alkyl, or wherein each occurrence of R¹¹, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of R¹², when present, is independently halogen; wherein each of R⁵, R⁶ᵃ, R⁶ᵇ, and R⁶ᶜ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁷, when present, is halogen; and wherein R⁸, when present, is selected from —B(OR¹¹)₂ and —B(R¹²)₃, provided that when the compound has a structure represented by a formula:

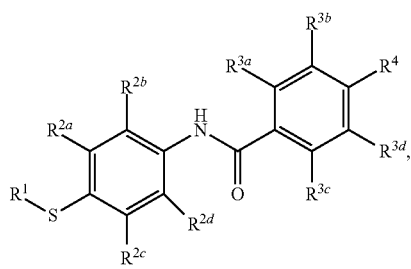

then R⁴ is —OH, C1-C4 alkyl, C1-C4 alkoxy, or —B(OR¹¹)₂; or a pharmaceutically acceptable salt thereof, thereby treating the disorder associated with KLF15 signaling dysfunction in the subject.

In one aspect, disclosed are methods for treating a disorder associated with Krüppel-Like Factor 15 (KLF15) signaling dysfunction in a subject in need thereof, the method comprising administering to the subject an effective amount of a compound having a structure represented by a formula selected from:

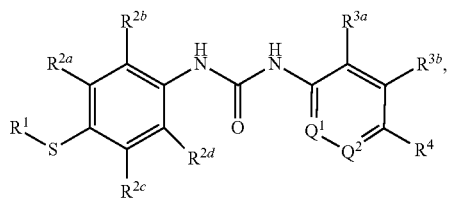

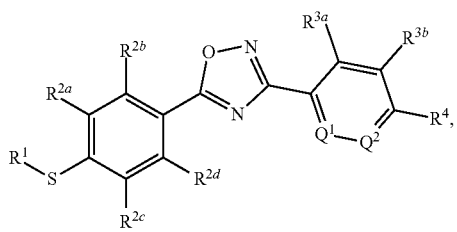

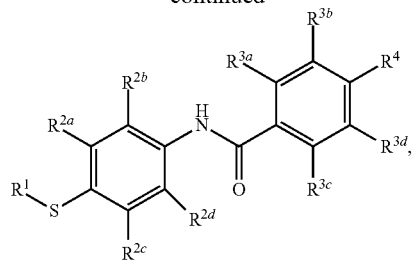

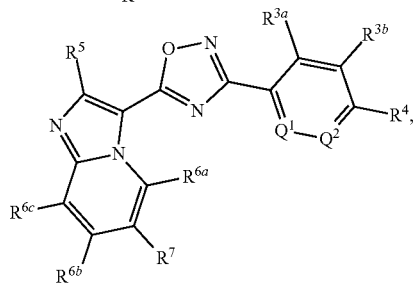

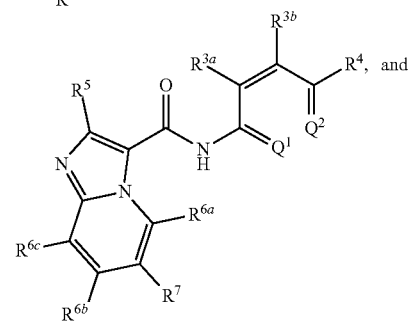

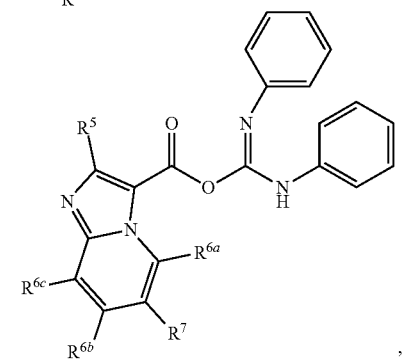

wherein each of Q¹ and Q² is independently selected from N and CR¹⁰; wherein R¹⁰, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹, when present, is C1-C4 alkyl; wherein each of R²ᵃ, R²ᵇ, R²ᶜ, R²ᵈ, R³ᵃ, and R³ᵇ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R³ᶜ and R³ᵈ, when present, is independently selected from hydrogen, halogen, —CN, —NH₂, —OH, —NO₂, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is independently selected from halogen, —CN, —OH, C1-C4 alkyl, C1-C4 alkoxy, and —B(OR$^{11}$)$_2$; wherein each occurrence of R$^{11}$, when present, is independently selected from hydrogen and C1-C8 alkyl, or wherein each occurrence of R$^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of R$^5$, R$^{6a}$, R$^{6b}$, and R$^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^7$, when present, is halogen, provided that when the compound has a structure represented by a formula:

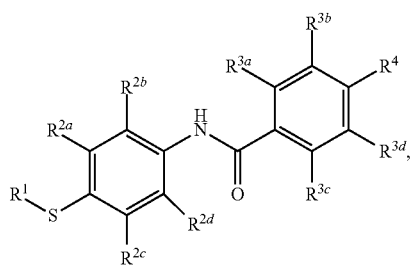

then R$^4$ is —OH, C1-C4 alkyl, C1-C4 alkoxy, or —B (OR$^{11}$)$_2$; or a pharmaceutically acceptable salt thereof, thereby treating the disorder associated with KLF15 signaling dysfunction in the subject.

In one aspect, disclosed are methods for treating a kidney disease in a subject in need thereof, the method comprising administering to the subject an effective amount of a compound selected from:

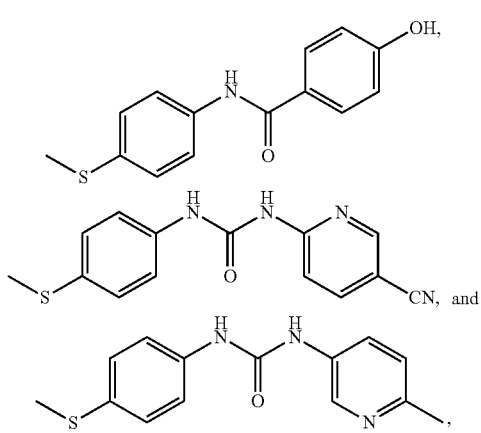

or a pharmaceutically acceptable salt thereof, thereby treating the kidney disease in the subject.

Examples of disorders associated with KLF15 signaling dysfunction include, but are not limited to, kidney disease, heart disease, obesity, or a neurodegenerative disorder. In a further aspect, the disorder is kidney disease. In a still further aspect, the kidney disease is chronic kidney disease. In yet a further aspect, the disorder is a neurodegenerative disorder. In an even further aspect, the neurodegenerative disorder is selected from amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD). In a still further aspect, the neurodegenerative disorder is Alzheimer's disease.

In a further aspect, the compound is selected from:

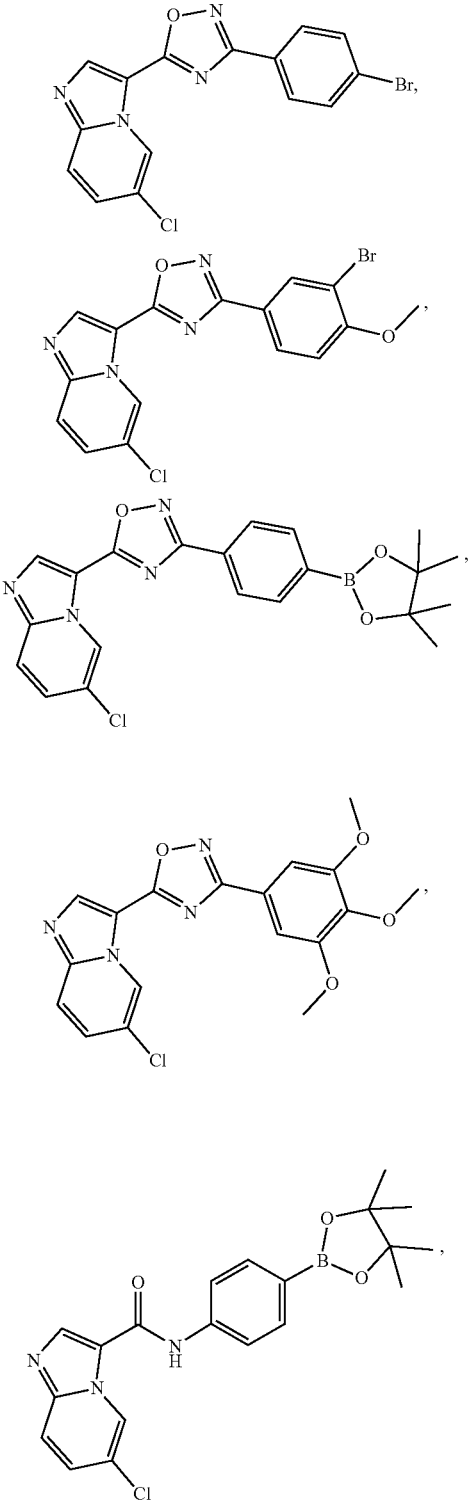

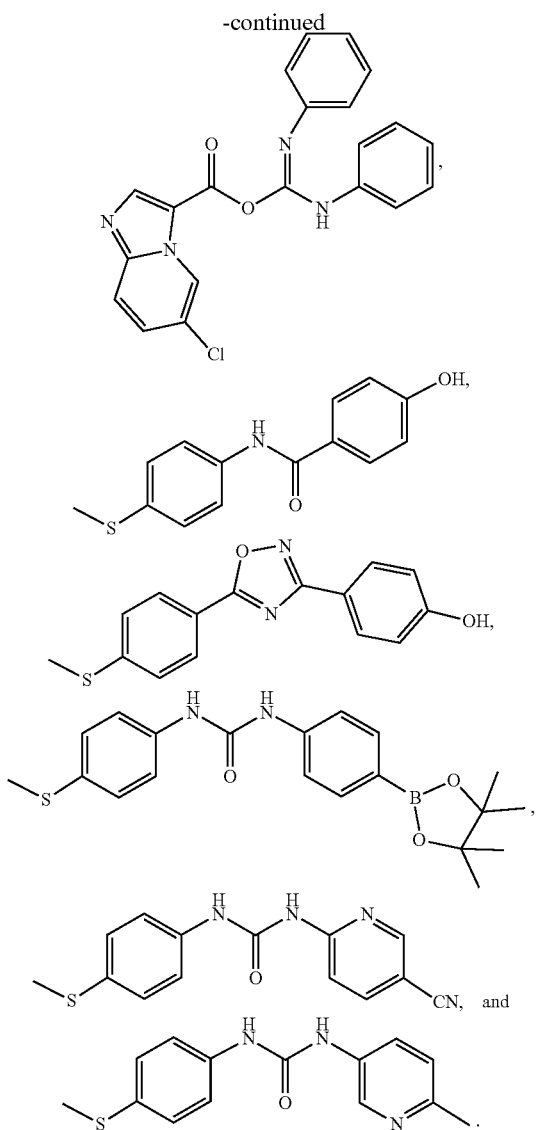

In a further aspect, the compound is:

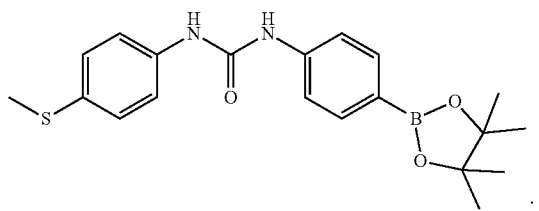

In a further aspect, the subject has been diagnosed with a need for treatment of the disorder prior to the administering step.

In a further aspect, the subject is at risk for developing the disorder prior to the administering step.

In a further aspect, the subject is a mammal. In a still further aspect, the mammal is a human.

In a further aspect, the method further comprises the step of identifying a subject in need of treatment of the disorder.

In a further aspect, the effective amount is a therapeutically effective amount. In a still further aspect, the effective amount is a prophylactically effective amount.

In a further aspect, the method further comprises administering to the subject an effective amount of a glucocorticoid. Examples of glucocorticoids include, but are not limited to, beclomethasone, betamethasone, budesonide, cortisone, dexamethasone, hydrocortisone, methylprednisolone, prednisolone, prednisone, and triamcinolone. In a still further aspect, the glucocorticoid is dexamethasone.

In various aspects, the compound and the glucocorticoid are administered simultaneously. In various further aspect, the compound and the glucocorticoid are administered sequentially.

2. Methods of Modifying KLF15 Signaling in a Mammal

In one aspect, disclosed are methods of modifying KLF15 signaling in a mammal, the method comprising the step of administering to the mammal a therapeutically effective amount of at least one disclosed compound, or a pharmaceutically acceptable salt thereof.

Thus, in one aspect, disclosed are methods for modifying KLF15 signaling in a subject, the method comprising administering to the subject an effective amount of a compound having a structure selected from:

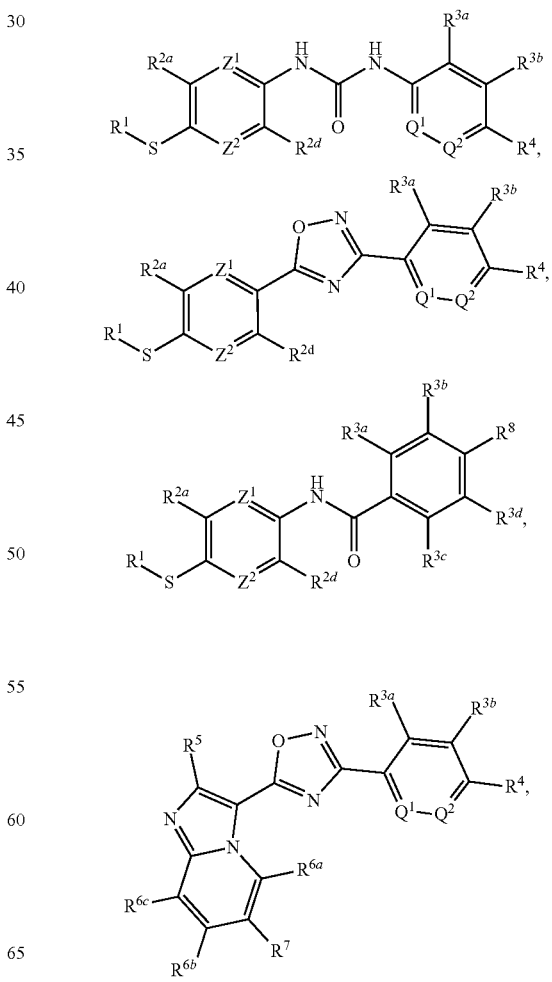

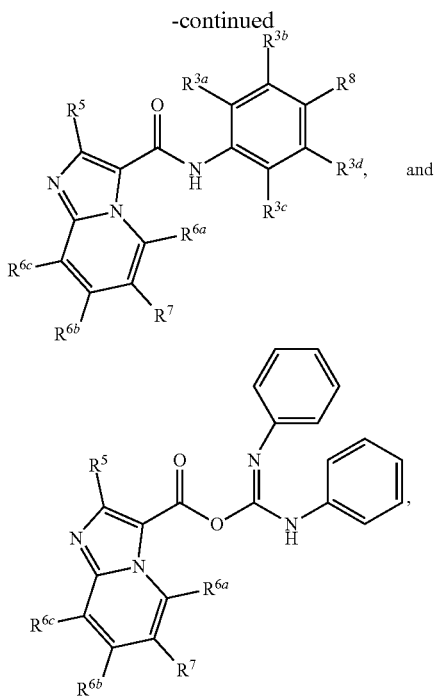

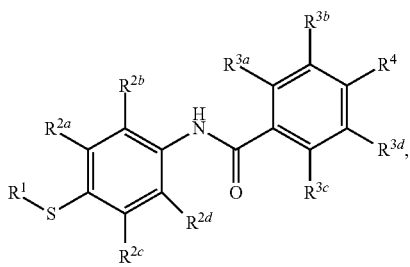

wherein each of $Q^1$ and $Q^2$ is independently selected from N and $CR^{10}$; wherein $R^{10}$, when present, is selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, —$B(OR^{11})_2$, and —$B(R^{12})_3$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —$B(OR^{11})_2$ and —$B(R^{12})_3$, provided that when the compound has a structure represented by a formula:

then $R^4$ is —OH, C1-C4 alkyl, C1-C4 alkoxy, or —$B(OR^{11})_2$; or a pharmaceutically acceptable salt thereof, thereby modifying KLF15 signaling in the subject.

Also disclosed are methods for modifying KLF15 signaling in a subject, the method comprising administering to the subject an effective amount of a compound having a structure selected from:

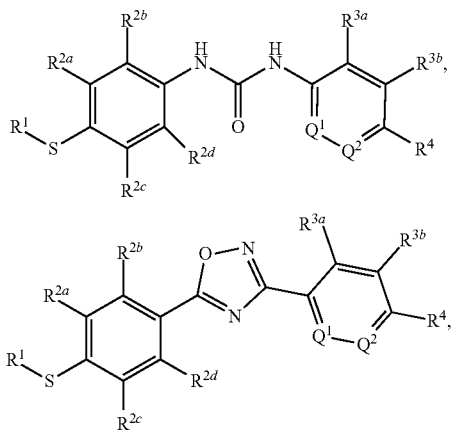

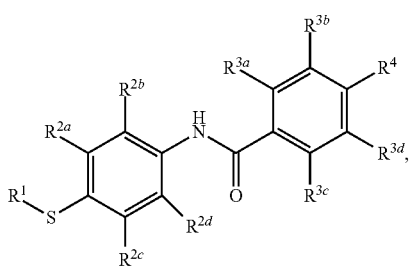

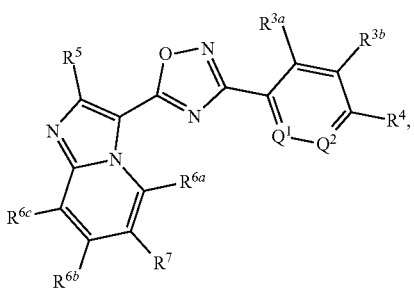

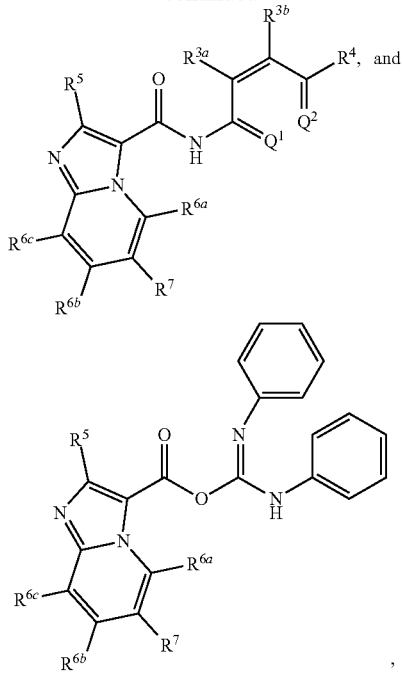

wherein each of $Q^1$ and $Q^2$ is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, and —B(OR$^{11}$)$_2$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^7$, when present, is halogen, provided that when the compound has a structure represented by a formula:

then $R^4$ is —OH, C1-C4 alkyl, C1-C4 alkoxy, or —B(OR$^{11}$)$_2$; or a pharmaceutically acceptable salt thereof, thereby modifying KLF15 signaling in the subject.

In a further aspect, modifying is activating. In a still further aspect, modifying is increasing.

In a further aspect, the compound exhibits activation of KLF15 signaling. In a still further aspect, the compound exhibits an increase in KLF15 signaling.

In a further aspect, the compound exhibits activation of KLF15 signaling with an EC$_{50}$ of less than about 30 μM. In a still further aspect, the compound exhibits activation of KLF15 signaling with an EC$_{50}$ of less than about 25 μM. In yet a further aspect, the compound exhibits activation of KLF15 signaling with an EC$_{50}$ of less than about 20 μM. In an even further aspect, the compound exhibits activation of KLF15 signaling with an EC$_{50}$ of less than about 15 μM. In a still further aspect, the compound exhibits activation of KLF15 signaling with an EC$_{50}$ of less than about 10 μM. In yet a further aspect, the compound exhibits activation of KLF15 signaling with an EC$_{50}$ of less than about 5 μM. In an even further aspect, the compound exhibits activation of KLF15 signaling with an EC$_{50}$ of less than about 1 μM. In a still further aspect, the compound exhibits activation of KLF15 signaling with an EC$_{50}$ of less than about 0.5 μM.

In a further aspect, the subject is a mammal. In a still further aspect, the subject is a human.

In a further aspect, the subject has been diagnosed with a disorder associated with KLF15 signaling prior to the administering step. In a still further aspect, the subject has been diagnosed with a need for modifying KLF15 signaling prior to the administering step. In yet a further aspect, the method further comprises the step of identifying a subject in need of treatment of a disorder associated with KLF15 signaling.

In a further aspect, the method further comprises administering to the subject an effective amount of a glucocorticoid. Examples of glucocorticoids include, but are not limited to, beclomethasone, betamethasone, budesonide, cortisone, dexamethasone, hydrocortisone, methylprednisolone, prednisolone, prednisone, and triamcinolone. In a still further aspect, the glucocorticoid is dexamethasone.

In various aspects, the compound and the glucocorticoid are administered simultaneously. In various further aspect, the compound and the glucocorticoid are administered sequentially.

3. Methods of Modifying KLF15 Signaling in at Least One Cell

In one aspect, disclosed are methods for modifying KLF15 signaling in at least one cell, the method comprising the step of contacting the at least one cell with an effective amount of at least one disclosed compound, or a pharmaceutically acceptable salt thereof.

Thus, in one aspect, disclosed are methods for modifying KLF15 in a cell, the method comprising contacting the cell with an effective amount of a compound having a structure selected from:

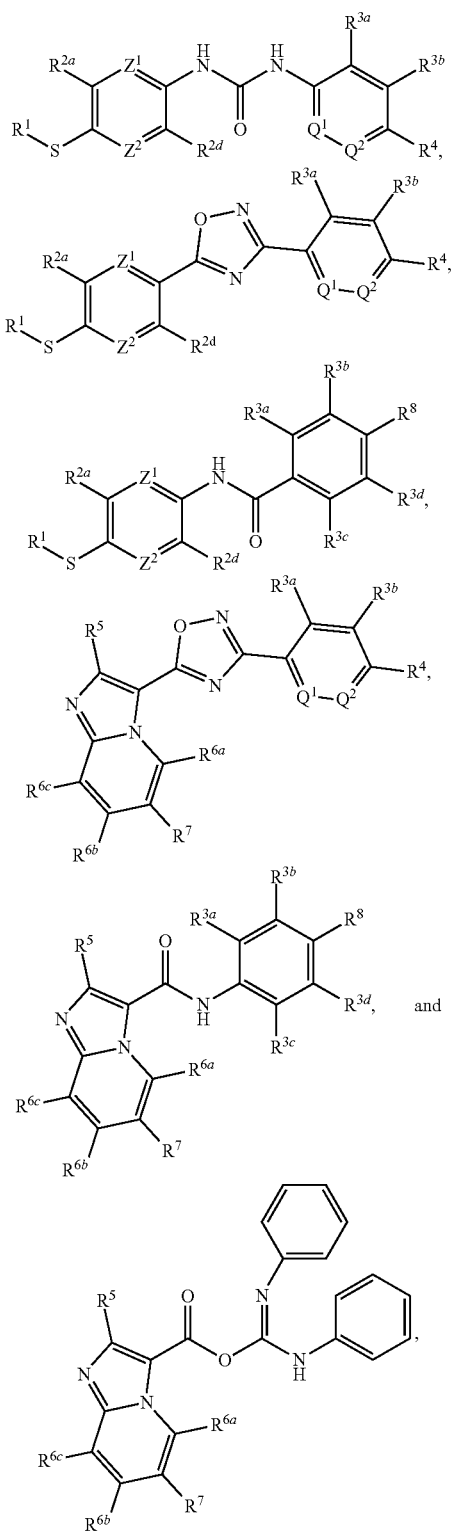

from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, —B(OR$^{11}$)$_2$, and —B(R$^{12}$)$_3$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —B(OR$^{11}$)$_2$ and —B(R$^{12}$)$_3$, provided that when the compound has a structure represented by a formula:

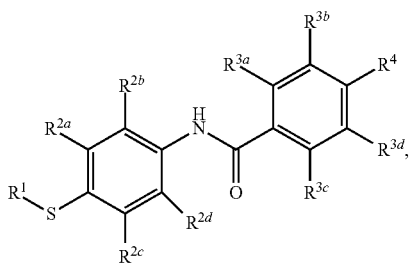

then $R^4$ is —OH, C1-C4 alkyl, C1-C4 alkoxy, or —B(OR$^{11}$)$_2$; or a pharmaceutically acceptable salt thereof, thereby modifying KLF15 signaling in the cell.

Also disclosed are methods for modifying KLF15 in a cell, the method comprising contacting the cell with an effective amount of a compound having a structure represented by a formula selected from:

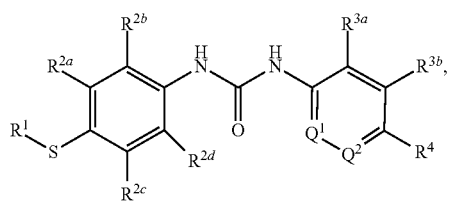

wherein each of $Q^1$ and $Q^2$ is independently selected from N and CR$^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected

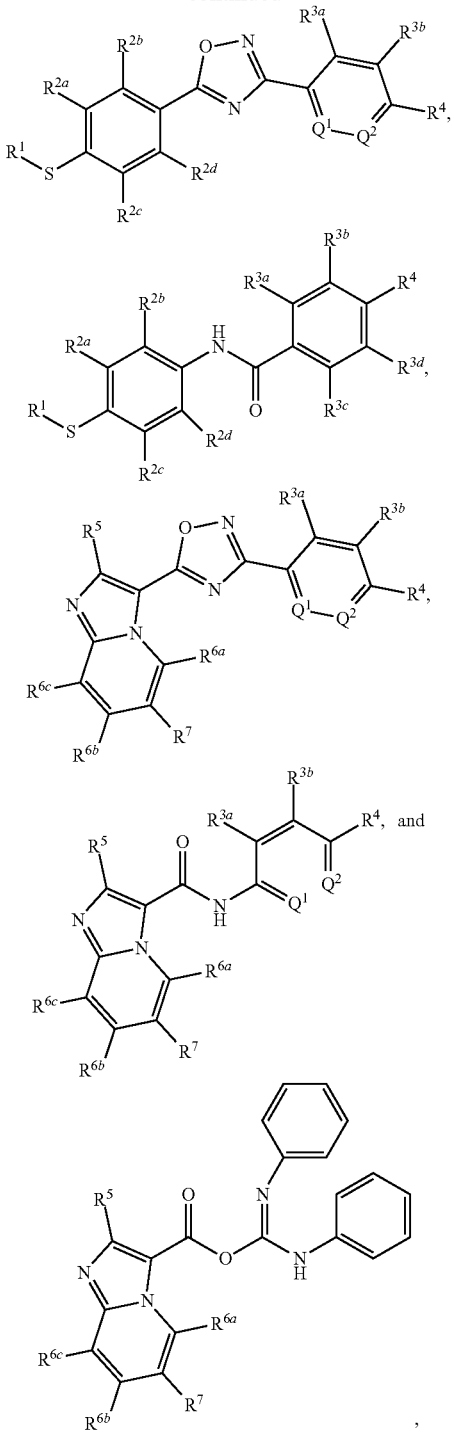

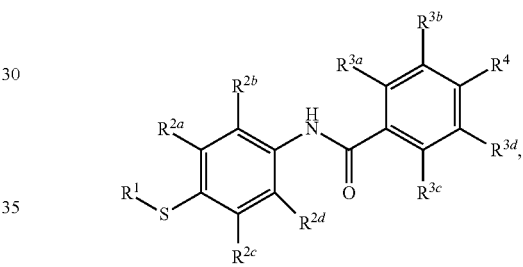

wherein each of Q¹ and Q² is independently selected from N and CR¹⁰; wherein R¹⁰, when present, is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹, when present, is C1-C4 alkyl; wherein each of R²ᵃ, R²ᵇ, R²ᶜ, R²ᵈ, R³ᵃ, and R³ᵇ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R³ᶜ and R³ᵈ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is independently selected from halogen, —CN, —OH, C1-C4 alkyl, C1-C4 alkoxy, and —B(OR¹¹)₂; wherein each occurrence of R¹¹, when present, is independently selected from hydrogen and C1-C8 alkyl, or wherein each occurrence of R¹¹, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of R⁵, R⁶ᵃ, R⁶ᵇ, and R⁶ᶜ, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R⁷, when present, is halogen, provided that when the compound has a structure represented by a formula:

then R⁴ is —OH, C1-C4 alkyl, C1-C4 alkoxy, or —B(OR¹¹)₂; or a pharmaceutically acceptable salt thereof, thereby modifying KLF15 signaling in the cell.

In a further aspect, modifying is activating. In a still further aspect, modifying is increasing.

In a further aspect, the cell is mammalian. In a still further aspect, the cell is human. In yet a further aspect, the cell has been isolated from a human prior to the contacting step.

In a further aspect, contacting is via administration to a subject. In a still further aspect, the subject has been diagnosed with a need for modification of KLF15 signaling prior to the administering step. In yet a further aspect, the subject has been diagnosed with a need for treatment of a disorder associated with KLF15 signaling dysfunction.

In a further aspect, the method further comprises contacting the cell with an effective amount of a glucocorticoid. Examples of glucocorticoids include, but are not limited to, beclomethasone, betamethasone, budesonide, cortisone, dexamethasone, hydrocortisone, methylprednisolone, prednisolone, prednisone, and triamcinolone. In a still further aspect, the glucocorticoid is dexamethasone.

4. Use of Compounds

In one aspect, the invention relates to the use of a disclosed compound or a product of a disclosed method. In a further aspect, a use relates to the manufacture of a medicament for the treatment of a disorder associated with KLF15 signaling dysfunction, as further described herein, in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of disorder associated with KLF15 signaling in a subject. Also disclosed is the use of a compound for activation of KLF15 signaling. In one aspect, the use is characterized in that the subject is a human. In one aspect, the use is characterized in that the disorder is kidney disease (e.g., chronic kidney disease), heart disease, obesity, or a neurodegenerative disorder (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)).

In a further aspect, the use relates to the manufacture of a medicament for the treatment of a disorder associated with KLF15 signaling in a subject.

In a further aspect, the use relates to activation of KLF15 signaling in a subject. In a further aspect, the use relates to modulating KLF15 signaling activity in a subject. In a still further aspect, the use relates to modulating KLF15 signaling activity in a cell. In yet a further aspect, the subject is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associate with KLF15 signaling dysfunction in a mammal. In a further aspect, the disorder is selected from kidney disease (e.g., chronic kidney disease), heart disease, obesity, or a neurodegenerative disorder (e.g., amyotrophic lateral sclerosis (ALS), Alzheimer's disease, Parkinson's disease, spinal muscular atrophy, traumatic brain injury, vascular dementia, Huntington's disease, mental retardation, attention deficit and hyperactivity disorder (ADHD)).

5. Manufacture of a Medicament

In one aspect, the invention relates to a method for the manufacture of a medicament for treating a disorder associated with KLF15 signaling dysfunction in a subject in need thereof, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of a viral infection. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, disclosed are kits comprising at least one disclosed compound and one or more of: (a) an agent associated with the treatment of a disorder associated with KLF15 signaling dysfunction; (b) instructions for administering the compound in connection with treating a disorder associated with KLF15 signaling dysfunction; and (c) instructions for treating a disorder associated with KLF15 signaling dysfunction.

In one aspect, disclosed are kits comprising a compound having a structure represented by a formula selected from:

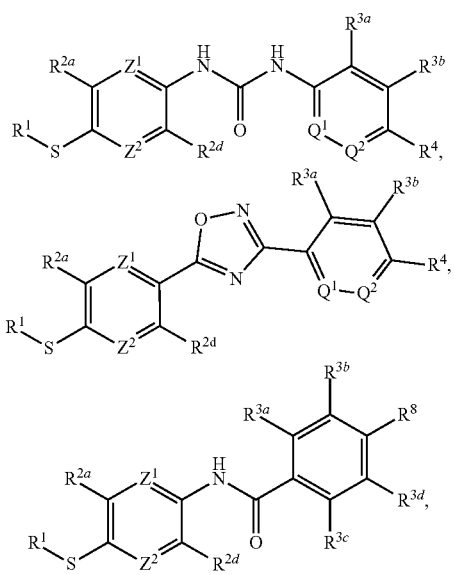

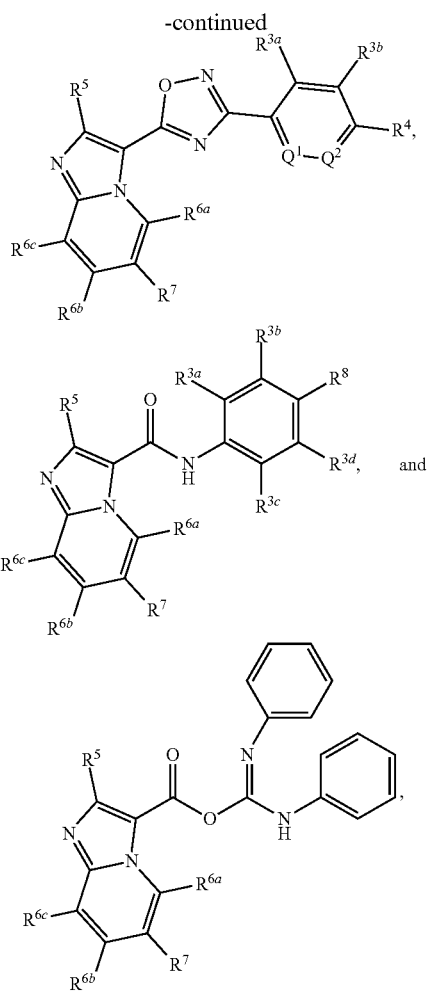

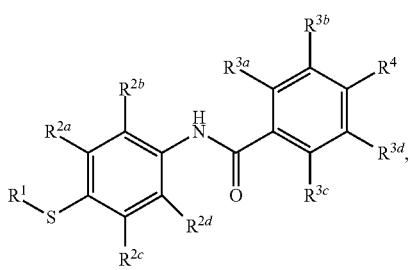

wherein each of $Q^1$ and $Q^2$ is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Z^1$, when present, is selected from N and $CR^{2b}$; wherein $Z^2$, when present, is selected from N and $CR^{2c}$; wherein $R^1$, when present, is C1-C4 alkyl; wherein each of $R^{2a}$, $R^{2b}$, $R^{2c}R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, —B(OR$^{11}$)$_2$, and —B(R$^{12}$)$_3$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each occurrence of $R^{12}$, when present, is independently halogen; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^7$, when present, is halogen; and wherein $R^8$, when present, is selected from —B(OR$^{11}$)$_2$ and —B(R$^{12}$)$_3$, provided that when the compound has a structure represented by a formula:

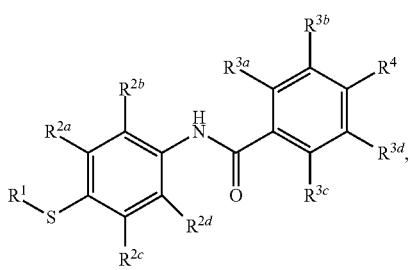

then $R^4$ is —OH, C1-C4 alkyl, C1-C4 alkoxy, or —B(OR$^{11}$)$_2$; or a pharmaceutically acceptable salt thereof, and one or more of: (a) an agent associated with the treatment of a disorder associated with KLF15 signaling dysfunction; (b) instructions for administering the compound in connection with treating a disorder associated with KLF15 signaling dysfunction; and (c) instructions for treating a disorder associated with KLF15 signaling dysfunction.

In one aspect, disclosed are kits comprising a compound having a structure represented by a formula selected from:

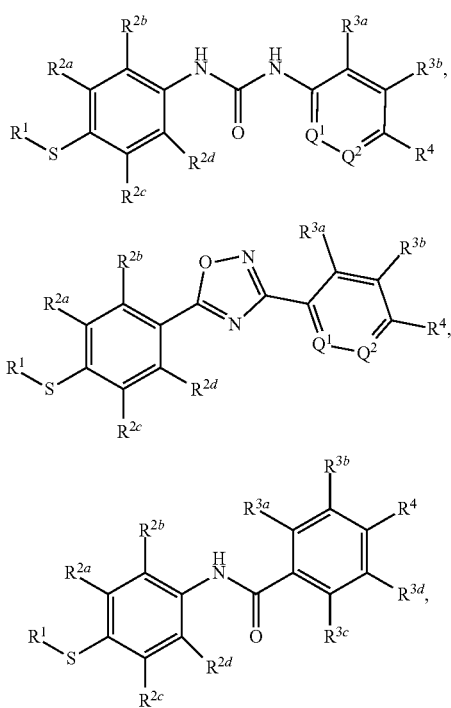

-continued

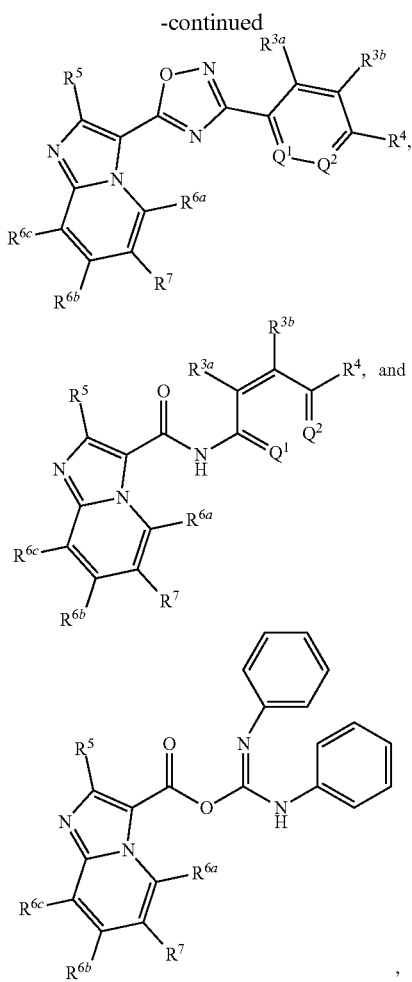

wherein each of $Q^1$ and $Q^2$ is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, and —B(OR$^{11}$)$_2$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^7$, when present, is halogen, provided that when the compound has a structure represented by a formula:

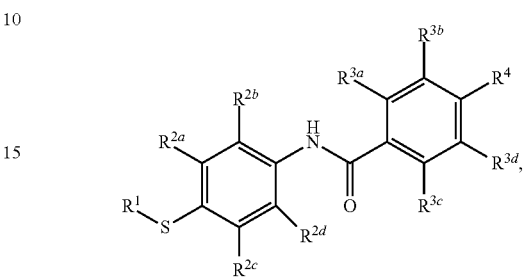

then $R^4$ is —OH, C1-C4 alkyl, C1-C4 alkoxy, or —B(OR$^{11}$)$_2$; or a pharmaceutically acceptable salt thereof, and one or more of: (a) an agent associated with the treatment of a disorder associated with KLF15 signaling dysfunction; (b) instructions for administering the compound in connection with treating a disorder associated with KLF15 signaling dysfunction; and (c) instructions for treating a disorder associated with KLF15 signaling dysfunction.

In one aspect, disclosed are kits comprising a compound having a structure represented by a formula selected from:

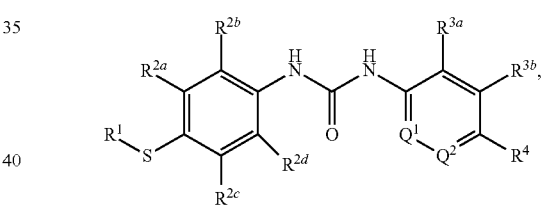

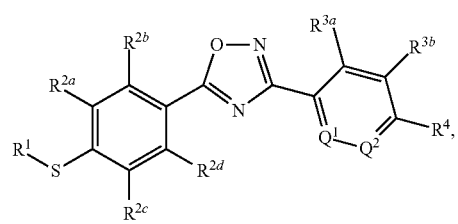

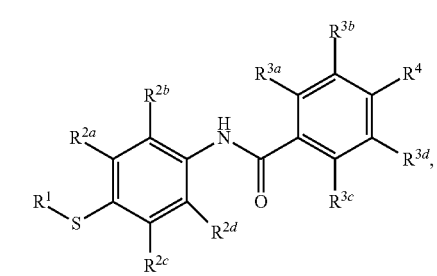

-continued

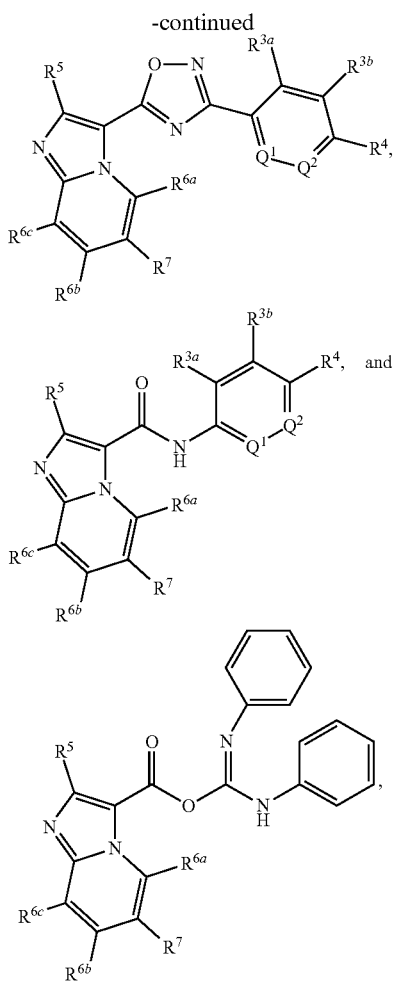

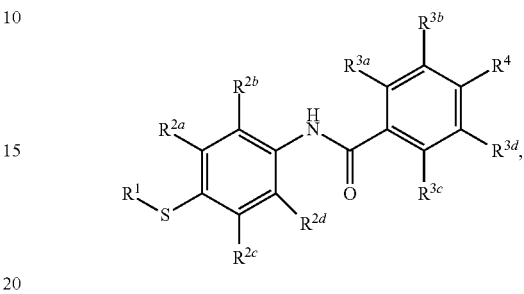

wherein each of $Q^1$ and $Q^2$ is independently selected from N and $CR^{10}$; wherein $R^{10}$, when present, is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^1$, when present, is C1-C4 alkyl; wherein each of $R^{2a}$, $R^{2b}$, $R^{2c}$, $R^{2d}$, $R^{3a}$, and $R^{3b}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{3c}$ and $R^{3d}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is independently selected from halogen, —CN, —OH, C1-C4 alkyl, C1-C4 alkoxy, and —B(OR$^{11}$)$_2$; wherein each occurrence of $R^{11}$, when present, is independently selected from hydrogen and C1-C8 alkyl, or wherein each occurrence of $R^{11}$, when present, is covalently bonded together, and, together with the intermediate atoms, comprise a C6 bicyclic heterocycle or a C2-C3 heterocycloalkyl, and is substituted with 0, 1, 2, 3, or 4 C1-C4 alkyl groups; wherein each of $R^5$, $R^{6a}$, $R^{6b}$, and $R^{6c}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $R^7$, when present, is halogen, provided that when the compound has a structure represented by a formula:

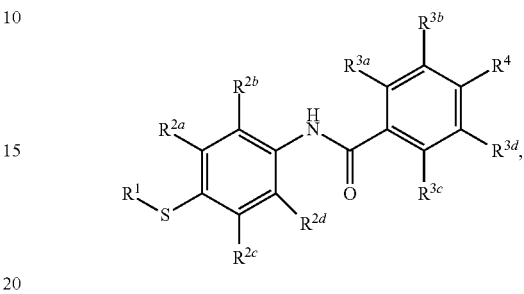

then $R^4$ is —OH, C1-C4 alkyl, C1-C4 alkoxy, or —B(OR$^{11}$)$_2$; or a pharmaceutically acceptable salt thereof, and one or more of: (a) an agent associated with the treatment of a disorder associated with KLF15 signaling dysfunction; (b) a glucocorticoid; (c) instructions for administering the compound in connection with treating a disorder associated with KLF15 signaling dysfunction; and (d) instructions for treating a disorder associated with KLF15 signaling dysfunction.

In a further aspect, the disorder associated with KLF15 signaling is kidney disease, heart disease, obesity, or a neurodegenerative disorder.

In a further aspect, the disorder associated with KLF15 signaling is kidney disease. In a still further aspect, the kidney disease is chronic kidney disease. In yet a further aspect, the agent associated with the treatment of kidney disease is an angiotensin-converting enzyme (ACE) inhibitor or an angiotensin II receptor blockers.

In a further aspect, the disorder associated with KLF15 signaling is heart disease. In a still further aspect, the agent associated with the treatment of heart disease is a blood thinner, a statin, a beta-blocker, or an angiotensin-converting enzyme (ACE) inhibitor.

In a further aspect, the disorder associated with KLF15 signaling is obesity. In a still further aspect, the agent associated with the treatment of obesity is a weight-loss medication.

In a further aspect, the disorder associated with KLF15 signaling is a neurodegenerative disorder. In a still further aspect, the neurodegenerative disorder is selected from amyotrophic lateral sclerosis (ALS), Alzheimer's disease, Parkinson's disease, spinal muscular atrophy, traumatic brain injury, vascular dementia, Huntington's disease, mental retardation, and attention deficit and hyperactivity disorder (ADHD). In yet a further aspect, the neurodegenerative disorder is Alzheimer's disease. In an even further aspect, the agent associated with the treatment of the neurodegenerative disorder is selected from a cholinesterase inhibitor, an antidepressant, memantine, rilutek, radicava, levodopa, carbidopa, a dopamine agonist, a MAO-B inhibitor, a catechol-O-methyltransferase inhibitor, an anticholinergic, spinraza, tetrabenazine, an antipsychotic agent, levetiracetam, clonazepam, an antipsychotic agent, a mood-stabilizing agent, and amantadine.

In a further aspect, the compound and the agent are administered sequentially. In a still further aspect, the compound and the agent are administered simultaneously.

In a further aspect, the compound and the agent are co-formulated. In a further aspect, the compound and the agent are co-packaged.

In a further aspect, the kit comprises the glucocorticoid. Examples of glucocorticoids include, but are not limited to, beclomethasone, betamethasone, budesonide, cortisone, dexamethasone, hydrocortisone, methylprednisolone, prednisolone, prednisone, and triamcinolone. In a still further aspect, the glucocorticoid is dexamethasone.

In various aspects, the compound and the glucocorticoid are co-packaged. In various further aspects, the compound and the glucocorticoid are co-formulated.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. REFERENCES

1. Wannamethee S G, Shaper A G, Perry I J. Serum creatinine concentration and risk of cardiovascular disease: a possible marker for increased risk of stroke. Stroke. 1997; 28(3):557-63.
2. Grundy S M, Benjamin I J, Burke G L, Chait A, Eckel R H, Howard B V, Mitch W, Smith S C, Jr., Sowers J R. Diabetes and cardiovascular disease: a statement for healthcare professionals from the American Heart Association. Circulation. 1999; 100(10):1134-46.
3. VA/DoD Clinical Practice Guideline: Management of Chronic Kidney Disease in Primary Care. 2014.
4. Meyrier A. Mechanisms of disease: focal segmental glomerulosclerosis. Nature clinical practice Nephrology. 2005; 1(1):44-54.
5. Barisoni L. Podocyte biology in segmental sclerosis and progressive glomerular injury. Adv Chronic Kidney Dis. 2012; 19(2):76-83.
6. Torban E, Braun F, Wanner N, Takano T, Goodyer P R, Lennon R, Ronco P, Cybulsky A V, Huber T B. From podocyte biology to novel cures for glomerular disease. Kidney Int. 2019; 96(4):850-61.
7. Pearson R, Fleetwood J, Eaton S, Crossley M, Bao S. Kruppel-like transcription factors: a functional family. Int J Biochem Cell Biol. 2008; 40(10):1996-2001.
8. Mallipattu S K, Liu R, Zheng F, Narla G, Ma'ayan A, Dikman S, Jain M K, Saleem M, D'Agati V, Klotman P, Chuang P Y, He J C. Kruppel-Like factor 15 (KLF15) is a key regulator of podocyte differentiation. J Biol Chem. 2012.
9. Mallipattu S K, Guo Y, Revelo M P, Roa-Pena L, Miller T, Ling J, Shankland S J, Bialkowska A B, Ly V, Estrada C, Jain M K, Lu Y, Ma'ayan A, Mehrotra A, Yacoub R, Nord E P, Woroniecki R P, Yang V W, He J C. Kruppel-Like Factor 15 Mediates Glucocorticoid-Induced Restoration of Podocyte Differentiation Markers. J Am Soc Nephrol. 2017; 28(1):166-84.
10. Guo Y, Pace J, Li Z, Ma'ayan A, Wang Z, Revelo M P, Chen E, Gu X, Attalah A, Yang Y, Estrada C, Yang V W, He J C, Mallipattu S K. Podocyte-Specific Induction of Kruppel-Like Factor 15 Restores Differentiation Markers and Attenuates Kidney Injury in Proteinuric Kidney Disease. J Am Soc Nephrol. 2018; 29(10):2529-45.
11. Gu X, Mallipattu S K, Guo Y, Revelo M P, Pace J, Miller T, Gao X, Jain M K, Bialkowska A B, Yang V W, He J C, Mei C. The loss of Kruppel-like factor 15 in Foxd1+ stromal cells exacerbates kidney fibrosis. Kidney Int. 2017.
12. Rane M J, Zhao Y, Cai L. Kruppel-like factors (KLFs) in renal physiology and disease. EBioMedicine. 2019; 40:743-50.
13. Wang L, Lin W, Chen J. Kruppel-like Factor 15: A Potential Therapeutic Target For Kidney Disease. Int J Biol Sci. 2019; 15(9):1955-61.
14. van Husen M, Kemper M J. New therapies in steroid-sensitive and steroid-resistant idiopathic nephrotic syndrome. Pediatr Nephrol. 2011; 26(6):881-92.
15. Ponticelli C, Locatelli F. Glucocorticoids in the Treatment of Glomerular Diseases: Pitfalls and Pearls. Clin J Am Soc Nephrol. 2018; 13(5):815-22.
16. Lee H W, Khan S Q, Faridi M H, Wei C, Tardi N J, Altintas M M, Elshabrawy H A, Mangos S, Quick K L, Sever S, Reiser J, Gupta V. A Podocyte-Based Automated Screening Assay Identifies Protective Small Molecules. J Am Soc Nephrol. 2015; 26(11):2741-52.
17. Zhang J H, Chung T D, Oldenburg K R. A Simple Statistical Parameter for Use in Evaluation and Validation of High Throughput Screening Assays. J Biomol Screen. 1999; 4(2):67-73.
18. Daina A, Michielin O, Zoete V. SwissADME: a free web tool to evaluate pharmacokinetics, drug-likeness and medicinal chemistry friendliness of small molecules. Sci Rep. 2017; 7:42717.
19. Reiser J, von Gersdorff G, Loos M, Oh J, Asanuma K, Giardino L, Rastaldi M P, Calvaresi N, Watanabe H, Schwarz K, Faul C, Kretzler M, Davidson A, Sugimoto H, Kalluri R, Sharpe A H, Kreidberg J A, Mundel P. Induction of B7-1 in podocytes is associated with nephrotic syndrome. J Clin Invest. 2004; 113(10):1390-7.
20. Das B C, Thapa P, Karki R, Schinke C, Das S, Kambhampati S, Banerjee S K, Van Veldhuizen P, Verma A, Weiss L M, Evans T. Boron chemicals in diagnosis and therapeutics. Future Med Chem. 2013; 5(6):653-76.
21. Zhong Y, Wu Y, Liu R, Li Z, Chen Y, Evans T, Chuang P, Das B, He J C. Novel retinoic acid receptor alpha agonists for treatment of kidney disease. PLoS One. 2011; 6(11):e27945.
22. Das B C, McCartin K, Liu T C, Peterson R T, Evans T. A forward chemical screen in zebrafish identifies a retinoic acid derivative with receptor specificity. PLoS One. 2010; 5(4):e10004.
23. Ahn J M, Boyle N A, MacDonald M T, Janda K D. Peptidomimetics and peptide backbone modifications. Mini Rev Med Chem. 2002; 2(5):463-73.
24. Lovering F, Bikker J, Humblet C. Escape from flatland: increasing saturation as an approach to improving clinical success. J Med Chem. 2009; 52(21):6752-6.
25. Das B C, Mahalingam S M, Evans T. Design and synthesis of novel pinacolylboronate containing combretastatin 'antimitotic agent' analogues. Tetrahedron Lett. 2009; 50(25):3031-4.
26. Das B C, Smith M E, Kalpana G V. Design, synthesis of novel peptidomimetic derivatives of 4-HPR for rhabdoid tumors. Bioorg Med Chem Lett. 2008; 18(14):4177-80.
27. Das B C, Madhukumar A V, Anguiano J, Mani S. Design, synthesis and biological evaluation of 2H-benzo[b][1,4] oxazine derivatives as hypoxia targeted compounds for cancer therapeutics. Bioorg Med Chem Lett. 2009; 19(15):4204-6.
28. Schinke C, Goel S, Bhagat T D, Zhou L, Mo Y, Gallagher R, Kabalka G W, Platanias L C, Verma A, Das B. Design and synthesis of novel derivatives of all-trans retinoic acid demonstrate the combined importance of acid moiety and conjugated double bonds in its binding to PML-RAR-alpha oncogene in acute promyelocytic leukemia. Leuk Lymphoma. 2010; 51(6):1108-14.
29. Muller P Y, Milton M N. The determination and interpretation of the therapeutic index in drug development. Nat Rev Drug Discov. 2012; 11(10):751-61.
30. Mallipattu S K, Home S J, D'Agati V, Narla G, Liu R, Frohman M A, Dickman K, Chen E Y, Ma'ayan A, Bialkowska A B, Ghaleb A M, Nandan M O, Jain M K, Daehn I, Chuang P Y, Yang V W, He J C. Kruppel-like factor 6 regulates mitochondrial function in the kidney. J Clin Invest. 2015; 125(3):1347-61.
31. Clark N R, Hu K S, Feldmann A S, Kou Y, Chen E Y, Duan Q, Ma'ayan A. The characteristic direction: a geometrical approach to identify differentially expressed genes. BMC Bioinformatics. 2014; 15:79.
32. Kuleshov M V, Jones M R, Rouillard A D, Fernandez N F, Duan Q, Wang Z, Koplev S, Jenkins S L, Jagodnik K M, Lachmann A, McDermott M G, Monteiro C D, Gundersen G W, Ma'ayan A. Enrichr: a comprehensive gene set enrichment analysis web server 2016 update. Nucleic Acids Res. 2016; 44(W1):W90-7.
33. Chen E Y, Tan C M, Kou Y, Duan Q, Wang Z, Meirelles G V, Clark N R, Ma'ayan A. Enrichr: interactive and collaborative HTML5 gene list enrichment analysis tool. BMC Bioinformatics. 2013; 14:128.
34. Onakpoya I J, Heneghan C J, Aronson J K. Post-marketing withdrawal of 462 medicinal products because of adverse drug reactions: a systematic review of the world literature. BMC Med. 2016; 14:10.
35. Neuhoff S, Artursson P, Zamora I, Ungell A L. Impact of extracellular protein binding on passive and active drug transport across Caco-2 cells. Pharm Res. 2006; 23(2):350-9.
36. McCarren P, Springer C, Whitehead L. An investigation into pharmaceutically relevant mutagenicity data and the influence on Ames predictive potential. J Cheminform. 2011; 3:51.
37. Walsky R L, Boldt S E. In vitro cytochrome P450 inhibition and induction. Curr Drug Metab. 2008; 9(9): 928-39.
38. Naik R, Valentine H, Dannals R F, Wong D F, Horti A G. Synthesis and Evaluation of a New (18)F-Labeled Radiotracer for Studying the GABAB Receptor in the Mouse Brain. ACS Chem Neurosci. 2018; 9(6):1453-61.
39. Bonomi R E, Laws M, Popov V, Kamal S, Potukutchi S, Shavrin A, Lu X, Turkman N, Liu R S, Mangner T, Gelovani J G. A Novel Substrate Radiotracer for Molecular Imaging of SIRT2 Expression and Activity with Positron Emission Tomography. Mol Imaging Biol. 2018; 20(4):594-604.
40. Solingapuram Sai K K, Das B C, Sattiraju A, Almaguel F G, Craft S, Mintz A. Radiolabeling and initial biological evaluation of [(18)F]KBM-1 for imaging RAR-alpha receptors in neuroblastoma. Bioorg Med Chem Lett. 2017; 27(6):1425-7.
41. Bonomi R, Mukhopadhyay U, Shavrin A, Yeh H H, Majhi A, Dewage S W, Najjar A, Lu X, Cisneros G A, Tong W P, Alauddin M M, Liu R S, Mangner T J, Turkman N, Gelovani J G. Novel Histone Deacetylase Class IIa Selective Substrate Radiotracers for PET Imaging of Epigenetic Regulation in the Brain. PLoS One. 2015; 10(8):e0133512.
42. Pico A R, Kelder T, Van Iersel M P, Hanspers K, Conklin B R, Evelo C. WikiPathways: pathway editing for the people. PLoS Biol. 2008; 6(7):e184.
43. Kanehisa M, Goto S. KEGG: kyoto encyclopedia of genes and genomes. Nucleic Acids Res. 2000; 28(1):27-30.
44. Ghali J R, O'Sullivan K M, Eggenhuizen P J, Holdsworth S R, Kitching A R. Interleukin-17RA Promotes Humoral Responses and Glomerular Injury in Experimental Rapidly Progressive Glomerulonephritis. Nephron. 2017; 135(3):207-23.
45. Ramani K, Pawaria S, Maers K, Huppler A R, Gaffen S L, Biswas P S.
An essential role of interleukin-17 receptor signaling in the development of autoimmune glomerulonephritis. J Leukoc Biol. 2014; 96(3):463-72.
46. Ahmed M, Gaffen S L. IL-17 inhibits adipogenesis in part via C/EBPalpha, PPARgamma and Kruppel-like factors. Cytokine. 2013; 61(3):898-905.
47. Yang S, Wang Y, Mei K, Zhang S, Sun X, Ren F, Liu S, Yang Z, Wang X, Qin Z, Chang Z. Tumor necrosis factor receptor 2 (TNFR2).interleukin-17 receptor D (IL-17RD) heteromerization reveals a novel mechanism for NF-kappaB activation. J Biol Chem. 2015; 290(2):861-71.
48. Zhang B, Liu C, Qian W, Han Y, Li X, Deng J. Structure of the unique SEFIR domain from human interleukin 17 receptor A reveals a composite ligand-binding site containing a conserved alpha-helix for Act1 binding and IL-17 signaling. Acta Crystallogr D Biol Crystallogr. 2014; 70(Pt 5):1476-83.
49. Noack C, Haupt L P, Zimmermann W H, Streckfuss-Bomeke K, Zelarayan L C. Generation of a KLF15 homozygous knockout human embryonic stem cell line using paired CRISPR/Cas9n, and human cardiomyocytes derivation. Stem Cell Res. 2017; 23:127-31.
50. Kapp T G, Rechenmacher F, Neubauer S, Maltsev O V, Cavalcanti-Adam E A, Zarka R, Reuning U, Notni J, Wester H J, Mas-Moruno C, Spatz J, Geiger B, Kessler H.

A Comprehensive Evaluation of the Activity and Selectivity Profile of Ligands for RGD-binding Integrins. Sci Rep. 2017; 7:39805.
51. Mould A P, Craig S E, Byron S K, Humphries M J, Jowitt T A. Disruption of integrin-fibronectin complexes by allosteric but not ligand-mimetic inhibitors. Biochem J. 2014; 464(3):301-13.
52. Koh K H, Cao Y, Mangos S, Tardi N J, Dande R R, Lee H W, Samelko B, Altintas M M, Schmitz V P, Lee H, Mukherjee K, Peev V, Cimbaluk D J, Reiser J, Hahm E. Nonimmune cell-derived ICOS ligand functions as a renoprotective alphavbeta3 integrin-selective antagonist. J Clin Invest. 2019; 129(4):1713-26.
53. Hagmann H, Brinkkoetter P T. Experimental Models to Study Podocyte Biology: Stock-Taking the Toolbox of Glomerular Research. Front Pediatr. 2018; 6:193.
54. Czerniecki S M, Cruz N M, Harder J L, Menon R, Annis J, Otto E A, Gulieva R E, Islas L V, Kim Y K, Tran L M, Martins T J, Pippin J W, Fu H, Kretzler M, Shankland S J, Himmelfarb J, Moon R T, Paragas N, Freedman B S. High-Throughput Screening Enhances Kidney Organoid Differentiation from Human Pluripotent Stem Cells and Enables Automated Multidimensional Phenotyping. Cell Stem Cell. 2018; 22(6):929-40 e4.
55. Lachmann A, Torre D, Keenan A B, Jagodnik K M, Lee H J, Wang L, Silverstein M C, Ma'ayan A. Massive mining of publicly available RNA-seq data from human and mouse. Nature communications. 2018; 9(1):1366.
56. Zappia L, Phipson B, Oshlack A. Exploring the single-cell RNA-seq analysis landscape with the scRNA-tools database. PLOS Computational Biology. 2018; 14(6): e1006245.
57. Mao Q, Wang L, Goodison S, Sun Y. Dimensionality Reduction Via Graph Structure Learning. Proceedings of the 21th ACM SIGKDD International Conference on Knowledge Discovery and Data Mining; Sydney, NSW, Australia. 2783309: ACM; 2015. p. 765-74.
58. Kuleshov M V, Jones M R, Rouillard A D, Fernandez N F, Duan Q, Wang Z, Koplev S, Jenkins S L, Jagodnik K M, Lachmann A, McDermott M G, Monteiro C D, Gundersen G W, Ma'ayan A. Enrichr: a comprehensive gene set enrichment analysis web server 2016 update. Nucleic Acids Research. 2016.
59. Chen E, Tan C, Kou Y, Duan Q, Wang Z, Meirelles G, Clark N, Ma'ayan A. Enrichr: interactive and collaborative HTML5 gene list enrichment analysis tool. BMC Bioinformatics. 2013; 14(1):128.
60. Kanehisa M, Goto S. KEGG: kyoto encyclopedia of genes and genomes. Nucleic acids research. 2000; 28(1): 27-30.
61. Ashburner M, Ball C A, Blake J A, Botstein D, Butler H, Cherry J M, Davis A P, Dolinski K, Dwight S S, Eppig J T. Gene Ontology: tool for the unification of biology. Nature genetics. 2000; 25(1):25-9.
62. Reiser J, Mundel P. Danger signaling by glomerular podocytes defines a novel function of inducible B7-1 in the pathogenesis of nephrotic syndrome. Journal of the American Society of Nephrology: JASN. 2004; 15(9): 2246-8.
63. Ohse T, Vaughan M R, Kopp J B, Krofft R D, Marshall C B, Chang A M, Hudkins K L, Alpers C E, Pippin J W, Shankland S J. De novo expression of podocyte proteins in parietal epithelial cells during experimental glomerular disease. Am J Physiol Renal Physiol. 2010; 298(3):F702-11.
64. Zhang J, Pippin J W, Liu Z H, Shankland S J. Podocyte repopulation by renal progenitor cells following glucocorticoids treatment in experimental FSGS. Am J Physiol Renal Physiol. 2013; 304(11):F1375-89.
65. Barisoni L, Bruggeman L A, Mundel P, D'Agati V D, Klotman P E. HIV-1 induces renal epithelial dedifferentiation in a transgenic model of HIV-associated nephropathy. Kidney Int. 2000; 58(1):173-81.
66. Estrada C C, Paladugu P, Guo Y, Pace J, Revelo M P, Salant D J, Shankland S J, D'Agati V D, Mehrotra A, Cardona S, Bialkowska A B, Yang V W, He J C, Mallipattu S K. Kruppel-like factor 4 is a negative regulator of STAT3-induced glomerular epithelial cell proliferation. JCI Insight. 2018; 3(12).
67. Scarfe L, Schock-Kusch D, Ressel L, Murray P, Wilm B, de Caestecker M. Transdermal Measurement of Glomerular Filtration Rate in Mice. J Vis Exp. 2018(140).
68. Waldman M, Crew R J, Valeri A, Busch J, Stokes B, Markowitz G, D'Agati V, Appel G. Adult minimal-change disease: clinical characteristics, treatment, and outcomes. Clin J Am Soc Nephrol. 2007; 2(3):445-53.

G. EXAMPLES

Here, several key conceptually and technically innovative strategies for optimization of lead KLF15 agonists are disclosed: (1) To date, utilization of small molecules to induce the expression of a pro-differentiation transcription factor in kidney disease is conceptually innovative. (2) Although combinatorial therapy to reduce the cumulative GC dose is not new, incorporating this strategy during early pre-IND studies by combining the use of KLF15 agonists and GCs is innovative in maximizing the effectiveness of therapy and optimizing lead KLF15 agonists. (3) The use of human podocyte-based high-throughput screening (HTS) to identify novel small molecules KLF15 agonists is innovative and has not been previously described in glomerular disease. (4) An innovative lead-optimization strategy involving iterative medicinal chemistry in combination with Limited Rational Design (LRD) approach is used to identify and optimize novel KLF15 analogues that will be selective in the low nanomolar (<100 nM) for primary glomerulopathies in a cost-effective and less time-consuming manner. (5) An innovative strategy to augment in vivo PK profiling studies using KLF15 analogues labelled with radiotracer and conduct PET imaging is proposed. (6) Novel assays to assess IL-17RA activity-homogenous ELISA-like solid phase binding and surface plasmon resonance assays are utilized to optimize selectivity of KLF15 agonists. (7) Human kidney organoids are utilized with single-cell RNA-seq to enhance the rigor of the preclinical models for optimization of lead KLF15 agonists. (8) A preliminary SAR was conducted of K-7 and used to identify novel KLF15 analogues.

Without wishing to be bound by theory, the following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Significance of Klf15 Loss of Function and Gain of Function Studies

It was previously reported that the loss of Klf15 in mice increased the susceptibility to podocyte injury and albuminuria in lipopolysaccharide (LPS)-treated mice as well as adriamycin (ADR)-treated mice (8). Furthermore, it was observed that KLF15 expression is reduced in human kidney biopsies in podocytopathies such as FSGS and HIVAN (8). Based on these data, it was postulated that induction of hKLF15 in podocyte injury will restore podocyte health and improve kidney injury. As such, gain of function studies were conducted by generating a podocyte-specific tetracycline-inducible hKLF15 transgenic mouse and showed that induction of hKLF15 attenuated albuminuria, FSGS lesions, interstitial fibrosis, and improved kidney function and overall mortality in HIV-1 transgenic (Tg26) mice (FIG. 1A-D) (10). In addition, these findings were validated in a preclinical proteinuric model with anti-glomerular antibody model (10). Subsequent RNA-seq studies from this model demonstrated that KLF15 restores podocyte health through transcriptional regulation of key podocyte-specific genes, involved in the maintenance of actin cytoskeleton (10).

Figure 2A:
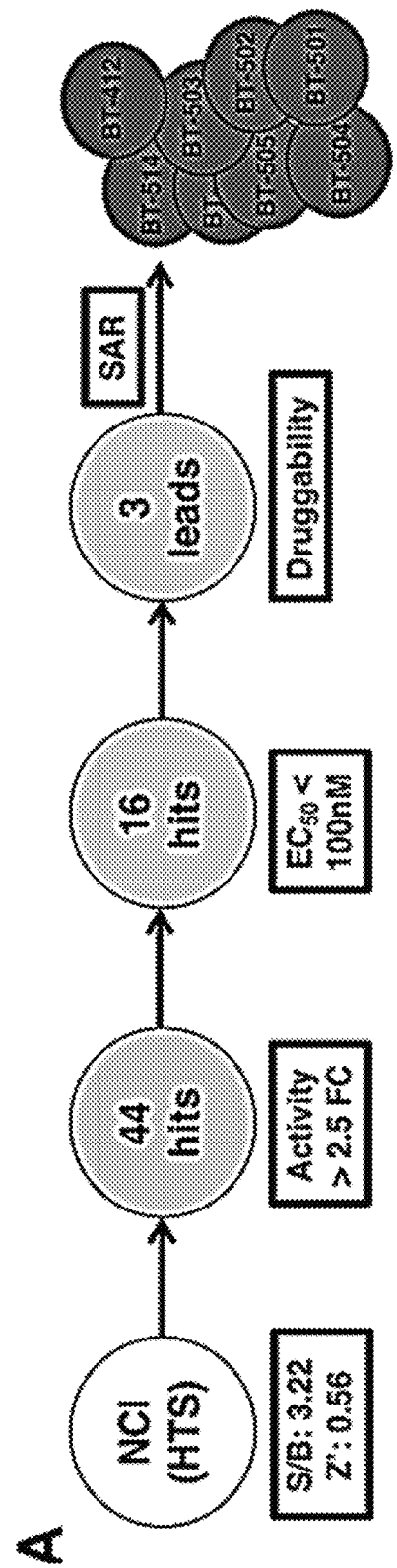
FIG. 2A-F show representative data illustrating the workflow from HTS to lead to novel derivatives (FIG. 2A), HTS screening assay with Z' score and S/B ratio (FIG. 2B), NSC #, Pubchem #, and $EC_{50}$ for 16 hits ("druggable" compounds) (FIG. 2C), structure (FIG. 2D) and dose-response curve ($EC_{50}$) (FIG. 2E), and Renilla (cell viability) for K-7, K-9, K-15, and DEX (FIG. 2F).
Figures 2B, 2C:
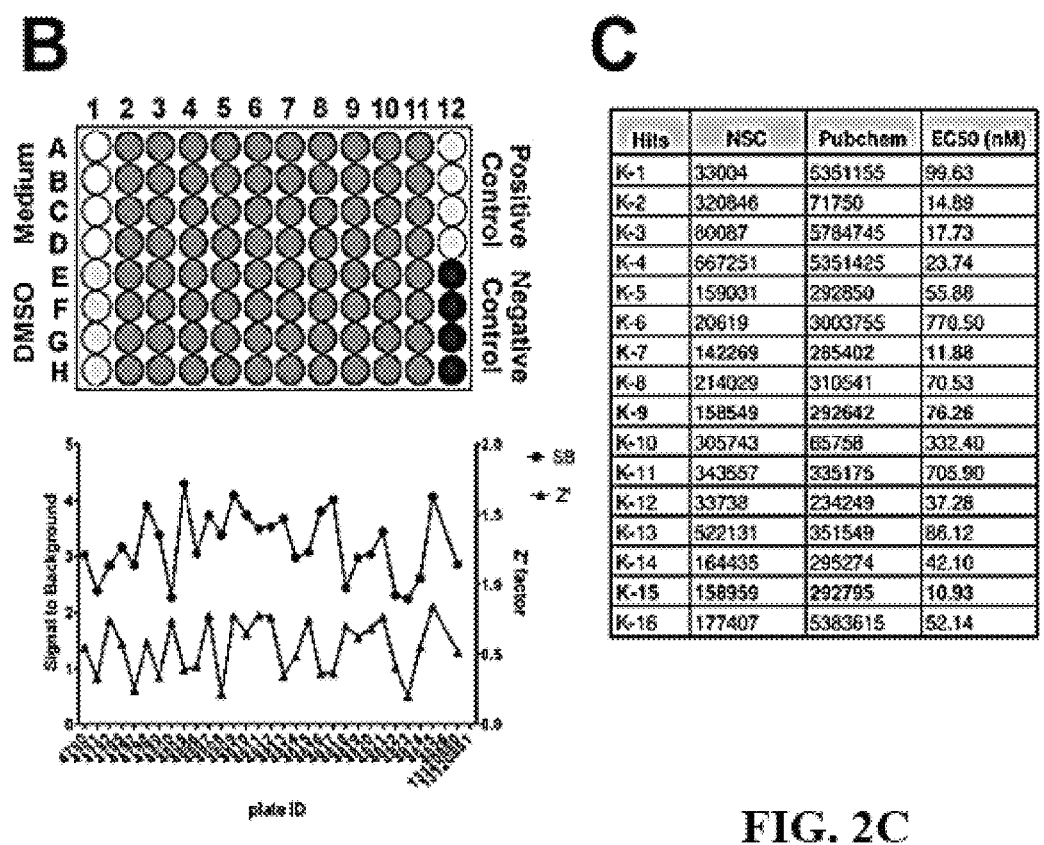
Figure 2D:
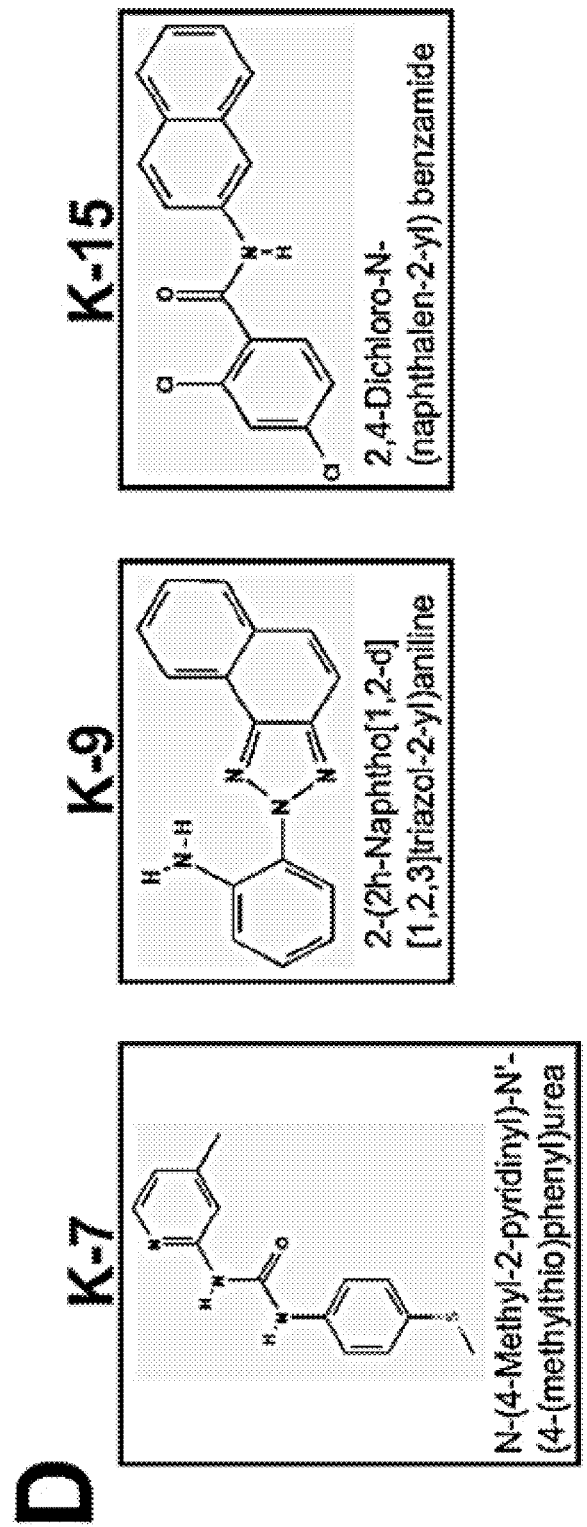
Figures 2E, 2F:
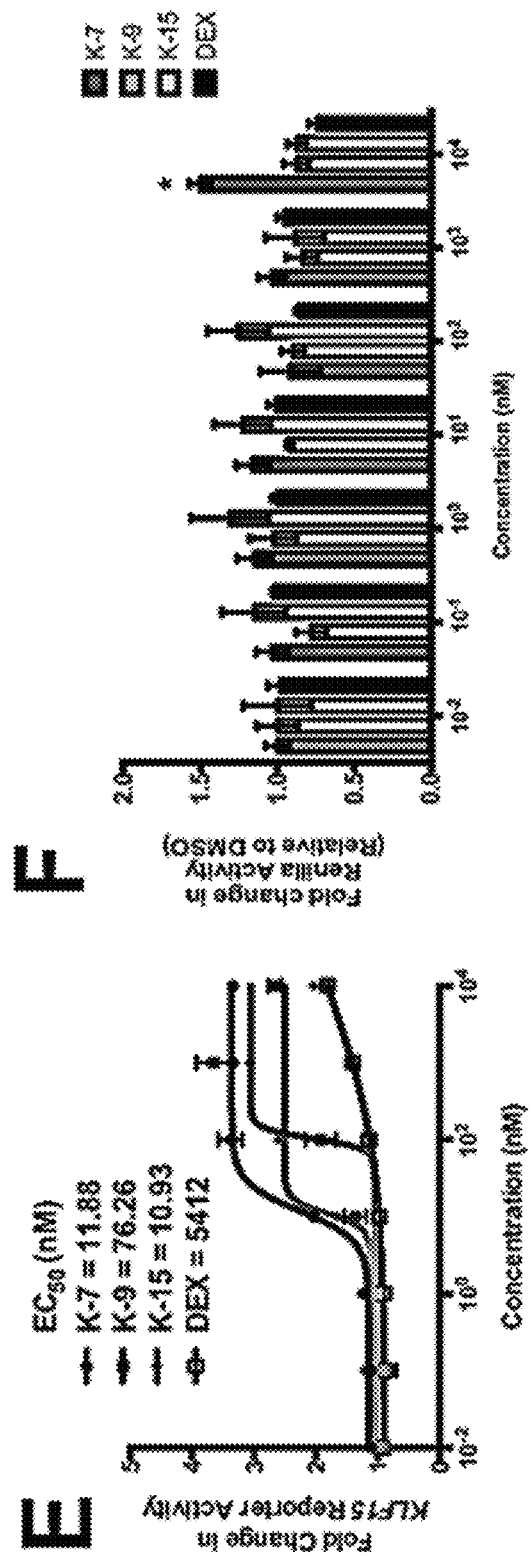

2. Design of Klf15 Reporter Human Podocyte Assay for HTS of Novel Small Molecule Klf15 Agonists A stable reporter assay directed at KLF15 promoter region (4.3 kb region) was generated in human podocytes, a fragment of human KLF15 promoter upstream of the start codon, by amplifying and subcloning it into the firefly luciferase reporter plasmid (co-transfection with renilla to serve as internal controls). KLF15 promoter activity is measured as a ratio of luciferase to renilla activity. Using this reporter cell line, a cell-based HTS assay was developed using recently reported cell-seeding methodology specific to cultured podocytes (16). Using this reporter assay, the National Cancer Institute Drug Screening Sets (2,645 compounds), Library of Pharmacologically Active Compounds from Sigma Inc. (1,280 compounds), and the Benzimidazole library (2,000 compounds) at the Institute of Chemical Biology and Drug Discovery (Stony Brook University) were screened at a final concentration of 1 µM in 1% DMSO for 24 hours (FIG. 2A). It was determined that this HTS screening exhibited high reproducibility with low variability as determined by a high signal to background (S/B) ~3.22 and a low Z-score (Z') ~0.56 (Z' is defined as the deviation of signal from the mean and used to test the variability in HTS (16, 17)). From this initial HTS, 44 hits with greater than 2.5-fold change in KLF15 reporter activity were identified (FIG. 2B). Dose-response curves were subsequently conducted for all 44 hits and 16 small molecules with $EC_{50}$<100 nM were identified (FIG. 2C). Based on the composition of low-nanomolar $EC_{50}$, stable cell viability, and the Lipinski's rule of five (evaluate druggability and the likelihood of the compound being orally active), K-7, K-9, and K-15 ($EC_{50}$~11.9 nM, 76.25 nM, and 10.93 nM, respectively) were advanced as KLF15 agonists (FIG. 2D and FIG. 2F). In comparison, dexamethasone (DEX, positive control) had an $EC_{50}$ of 5412 nM (FIG. 2E).

3. Preliminary PK Profiling and Therapeutic Efficacy of KLF15 Agonists

Figures 3A, 3B, 3C:
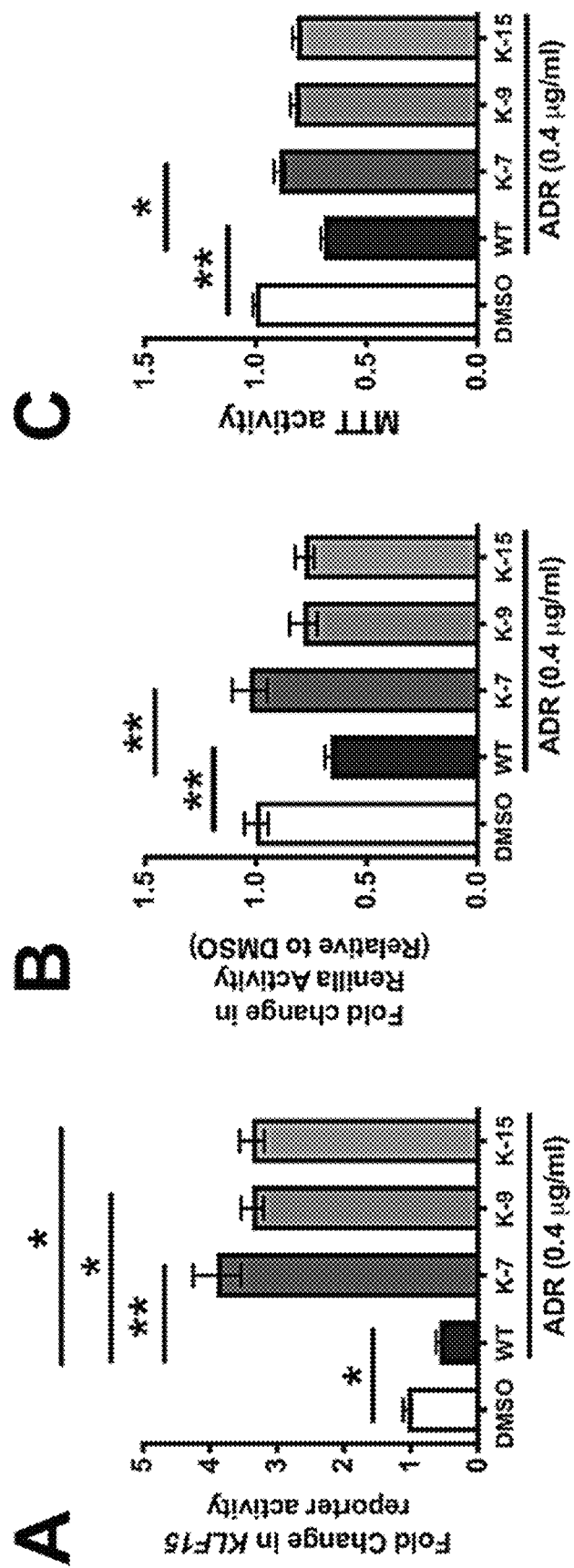
FIG. 3A-C show representative data illustrating the fold change in KLF15 reporter activity (FIG. 3A), Renilla activity (cell viability) (FIG. 3B), and MTT activity (cell viability) (FIG. 3C) in K-7, K-9, and K-15.

To initially determine the therapeutic efficacy of KLF15 agonists (K-7, K-9, and K-15), cultured human podocytes were treated (under nonpermissive conditions, 37° C.) with ADR. It was observed that all 3 leads restored KLF15 activity as compared to treatment with DMSO (negative control) (FIG. 3A). It was also observed that cell viability (measured by renilla activity and MTT assay) was only significantly improved with K-7 as compared to the K-9, K-15, DEX, and DMSO treatment (FIG. 3B and FIG. 3C). Based on these data, K-7 was used for pharmacokinetic (PK) profiling and for further testing in additional in vitro and in vivo models of podocyte injury.

Figure 4A:
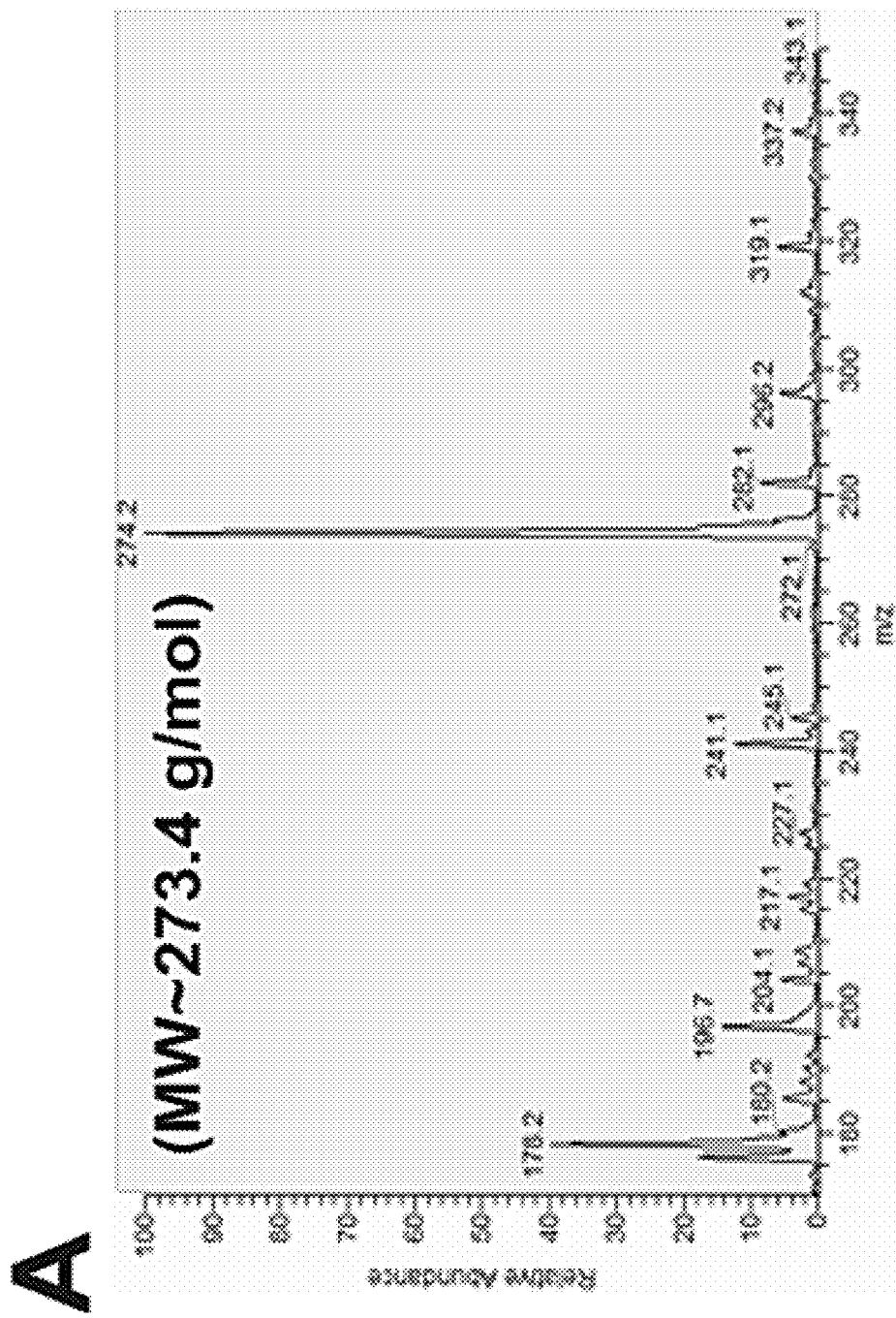
FIG. 4A and FIG. 4B show representative data illustrating an LC-MS trace to assess purity of K-7 (FIG. 4A) and the results of a Collision Induced Dissociation Study to determine potential biologically active metabolites (FIG. 4B).
Figure 4B:
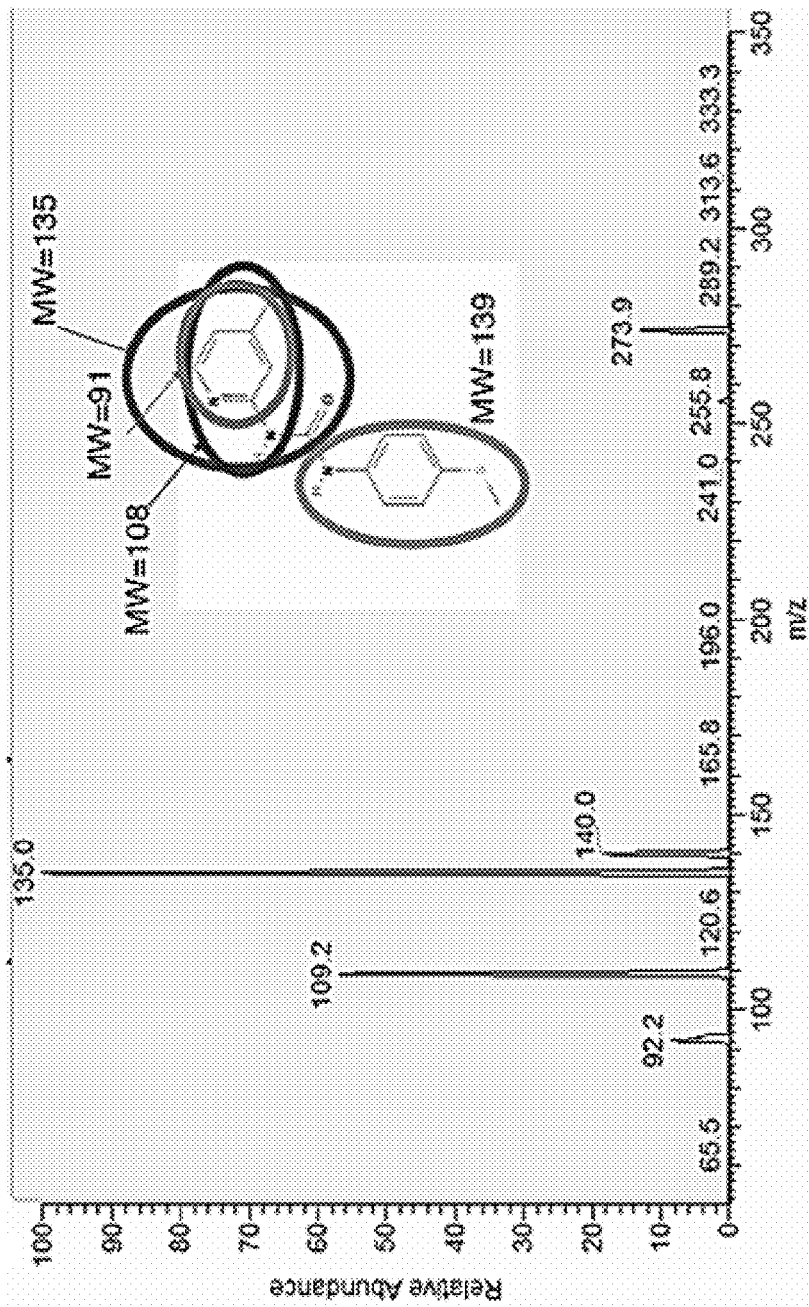
Figure 5A:
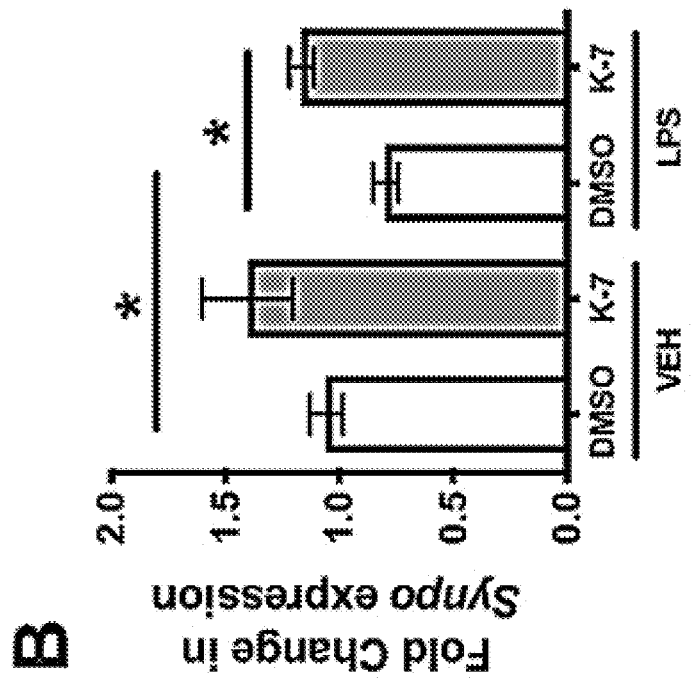
FIG. 5A-D show representative data illustrating KLF15 mRNA expression (FIG. 5A), Synaptopodin mRNA expression (FIG. 5B), KLF15, phalloidin quantification (Type A actin-stress fibers) in K-7/DMSO in LPS treated human podocytes (FIG. 5C), and Albuminuria in K-7 or DMSO in LPS-treated (10 mg/kg q24 hr) mice (FIG. 5D).
Figure 5B:
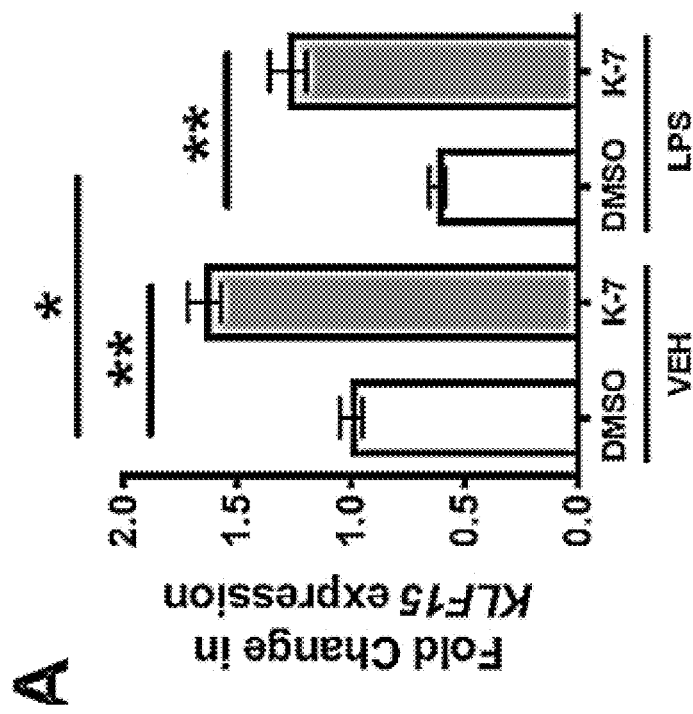
Figures 5C, 5D:
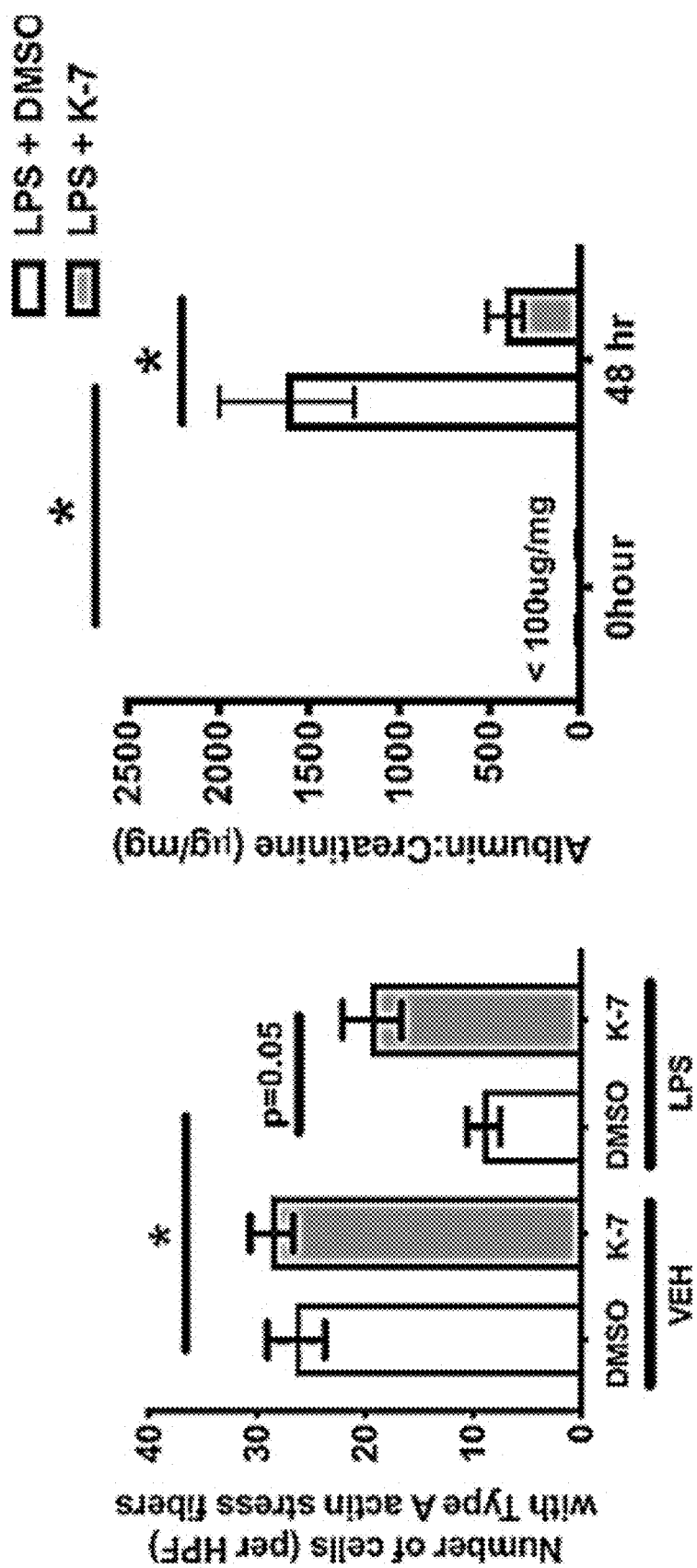

The purity of KLF15 agonist K-7 was initially measured by LC-MS/MS to determine the MW ~273 g/mol and a collision induced dissociation study was conducted to determine the potential biologically active metabolites (FIG. 4A and FIG. 4B). Furthermore, the open-source Swiss Institute of Bioinformatics was utilized to predict the pharmacokinetics, "leadlikeness," and medicinal chemistry of K-7 (Table 1). Based on this, K-7 demonstrates water solubility (Log S ~−3.32), moderate lipophilicity (Log Pow/~2.64), high GI absorption, impermeability to blood-brain barrier, highly druggable (based on Lipinski, Ghose, Veber, Egan tests (18)), with a high prediction to be a lead compound (Table 1). It was subsequently determined that K-7 restored KLF15 and synaptopodin expression as well as actin stress fiber formation as compared to DMSO-treated podocytes under LPS conditions (FIG. 5A-C). Since LPS has been utilized as a short-term proteinuric murine model by several laboratories (8, 9, 16, 19), mice were treated with K-7 (5 mg/kg, every 12 hours) as compared to DMSO and a significant improvement in albuminuria was observed with K-7 (as compared to DMSO) in LPS-proteinuric murine model (FIG. 5D).

TABLE 1

| Physiochemical Properties | |
| --- | --- |
| MW | 273.35 g/mol |
| # heavy atoms | 19 |
| # aromatic heavy atoms | 12 |
| # rotational bonds | 5 |
| # H-bond acceptors | 2 |
| # H-bond donors | 2 |
| Lipophilicity (XLOGP3) (−0.7 to +5.0) | 2.62 |
| Polarity (TSPA) (20 to 130 A°) | 79.32 A° |
| Solubility (log S) (not higher than 6) | −3.32 |
| Pharmacokinetics | |
| GI absorption | High |
| BBB permeability | No |
| Druglikeness | |
| Lipinski | Yes (0 Violation) |
| Ghose | Yes |
| Veber | Yes |
| Egan | Yes |
| Muegge | Yes |
| Bioavailability score | 0.55 |
| Leadlikeness | Yes |

Figure 6:
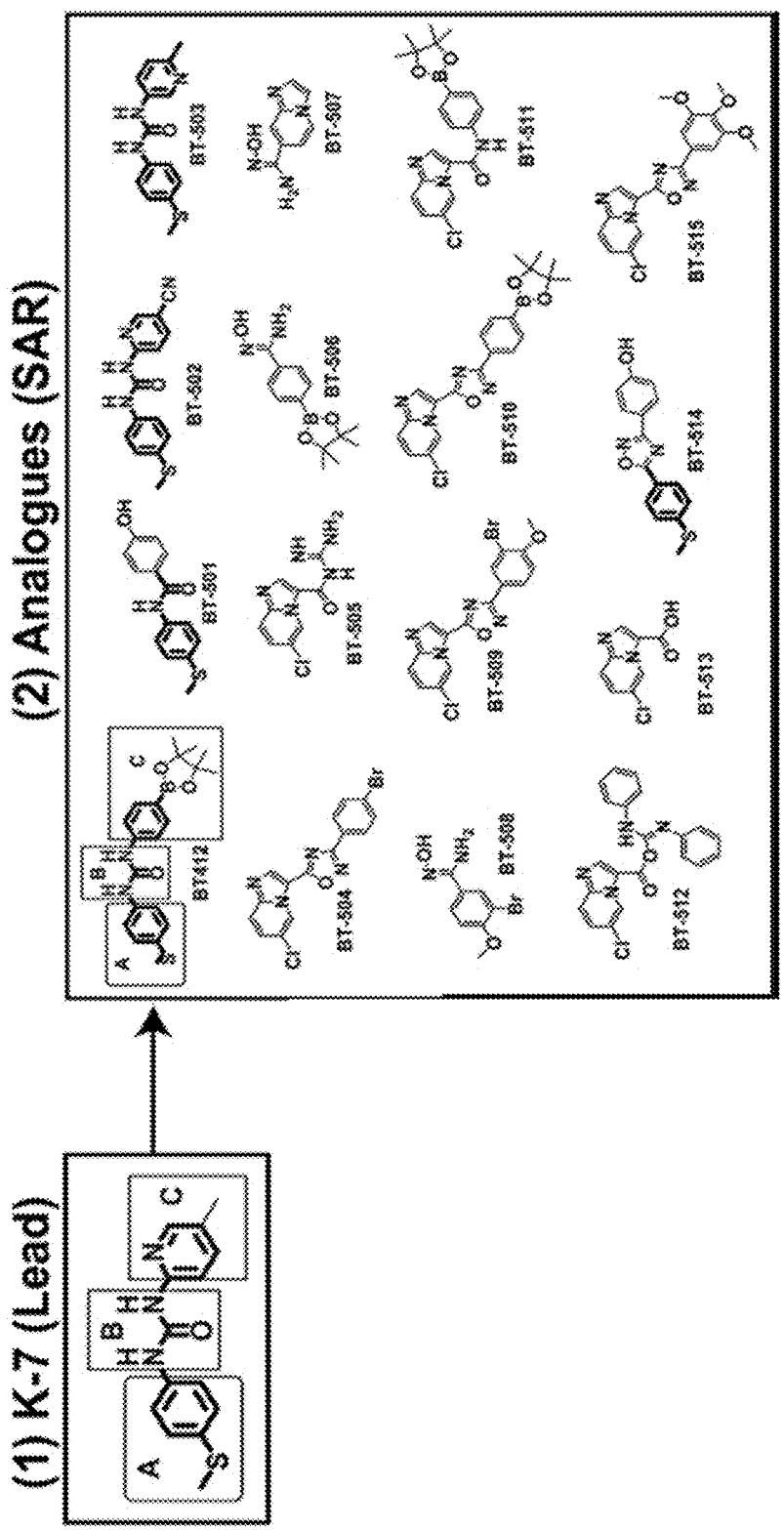
FIG. 6 shows representative data illustrating (1) the structure of lead K-7 and (2) analogues from the preliminary SAR. The structure is marked by (A) thiomethyl group, (B) urea derivative, and (C) pyridine derivative.

4. Preliminary Structure Activity Relationship (SAR) Study and Synthesis of K-7 Structural Analogues Based on the preceding low $EC_{50}$ and the "leadlikeness," K-7 was selected for a preliminary SAR study to synthesize novel K-7 structural analogues. 16 analogues were generated, with the goal of identifying less toxic, more specific KLF15 agonists (FIG. 6). In brief, the target-to-hit compound K-7 contains 3 structural moieties (Part A contains a 4-substituted thiomethyl group off of a phenyl ring system, Part B contains a substituted urea derivative, and Part C contains a substituted pyridine derivative). Initially, BT412, BT502, and BT503 were synthesized by substituting the pyridine ring in Part C (general schema is shown in FIG.

Figure 7A:
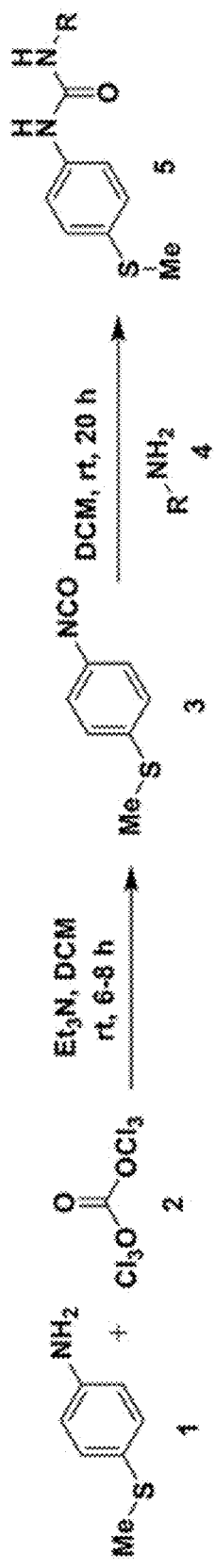
FIG. 7A and FIG. 7B show a representative synthesis of BT502 and BT503 by substituting the pyridine ring in Part C (FIG. 7A) and by replacing the methyl group with a boron ester for BT412 (FIG. 7B).
Figure 7B:
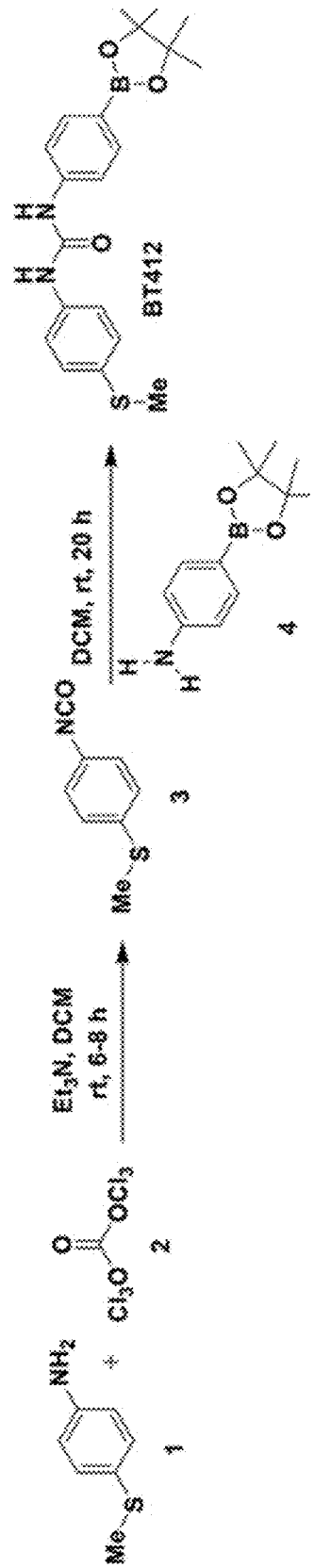

7A). In BT412, the role of boron chemistry in drug development was exploited (20) to introduce a boronic ester group in place of the methyl group, and the pyridine ring was replaced with a phenyl ring (FIG. 7B). The rationale to pursue this strategic modification is the recent success of boron-containing compounds in clinical use (e.g., Bortezomib, Tavaborole, Eucrisa, and Vaborbactam). Furthermore, the pharmacokinetic properties and stability of boron-containing compounds have been demonstrated in zebrafish, worms, and mice (20-22).

Figure 8A:
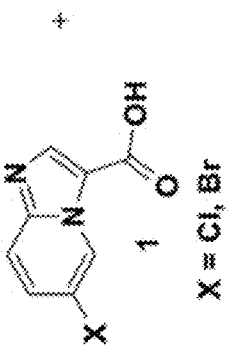
FIG. 8A and FIG. 8B show a representative synthesis of analogues BT510 and BT514 by replacing Part B (urea) with isostere amides and an oxadiazole.
Figure 8A:
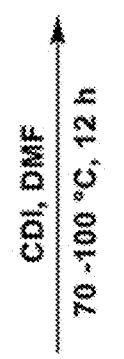
Figure 8A:
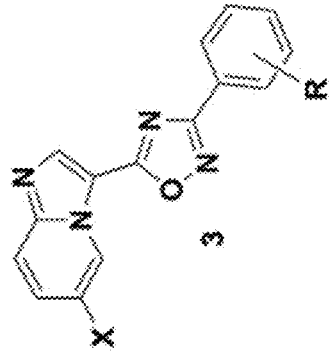
Figure 8B:
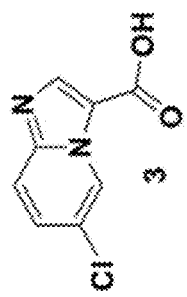
Figure 8B:
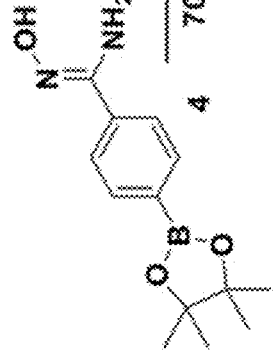
Figure 8B:
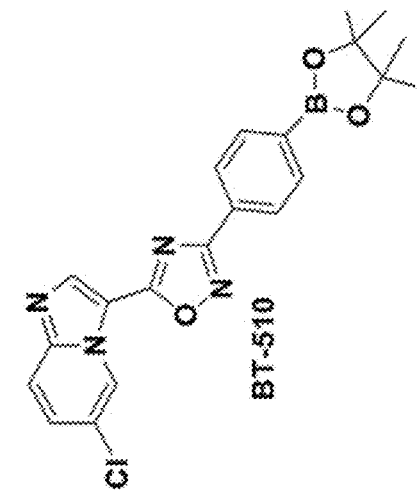

Analogues BT510 and BT514 were synthesized by replacing the urea derivatives (in ring Part B) with urea isosteres amides (BT501) and oxadiazole (BT514) (FIG. 8A and FIG. 8B). Since urea derivatives are prone to hydrolysis by urease inside the body, which leads to toxicity and off-target effects, the urea functional group was substituted with amides and oxadiazoles to mitigate this effect (23). Subsequently, new analogs were synthesized by substituting the Part A ring with imidazopyridine derivatives to generate analogues BT504, BT509-512, and BT515. Finally, a defragmented approach was conducted to synthesize analogue BT505-508. These compounds were designed to increase the cell membrane permeability and KLF15 specificity.

Figure 9:
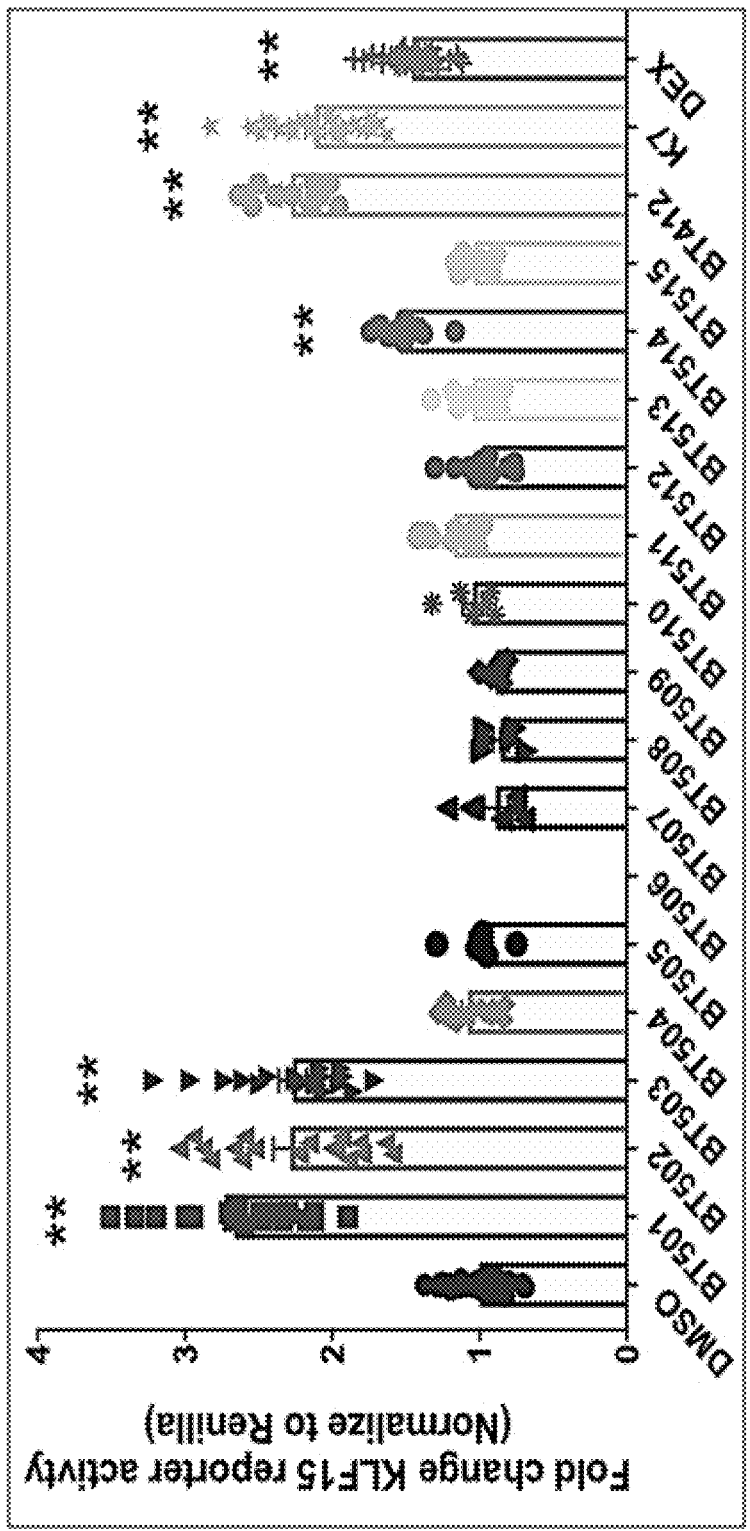
FIG. 9 shows representative data illustrating the fold change in KLF15 reporter activity (1 μM, 24 hr for each of the 16 analogues, K-7, DEX, and DMSO (control). Luciferase/Renilla activity. Toxicity only seen in BT506.
Figure 10A:
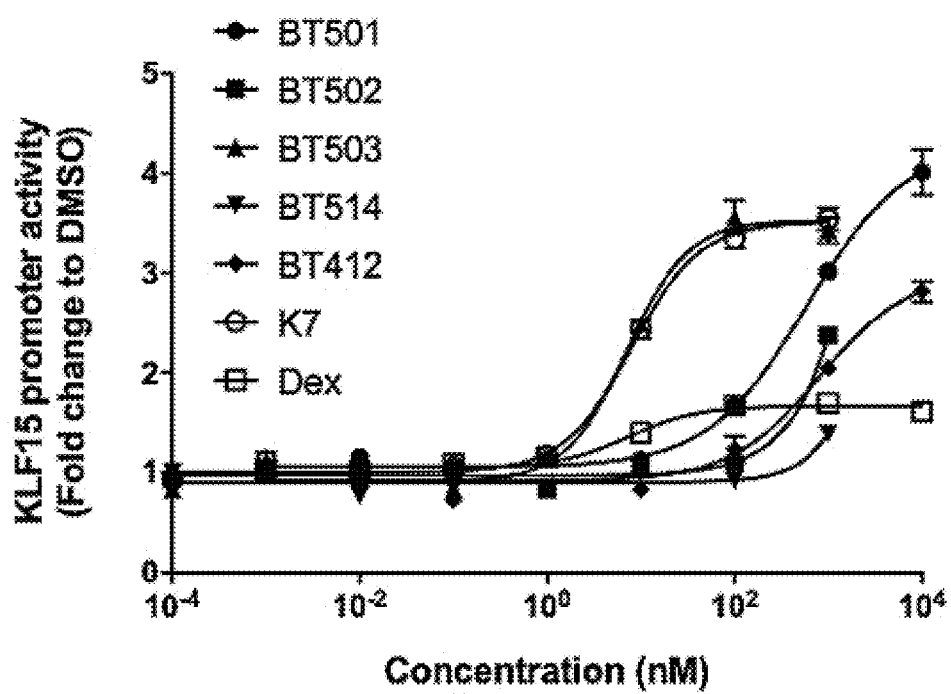
FIG. 10A-D show representative data illustrating the dose-response curve and $EC_{50}$ (FIG. 10A), KLF15 reporter activity (FIG. 10B), and Renilla activity (cell viability) (FIG. 10C) in LPS-treated HP, and the therapeutic efficacy in abrogating albuminuria (biomarker of kidney disease) in LPS-treated mice (FIG. 10D). Groups: BT501, 502, 503, 514, 412, K-7, DEX, and DMSO (control).
Figure 10C:
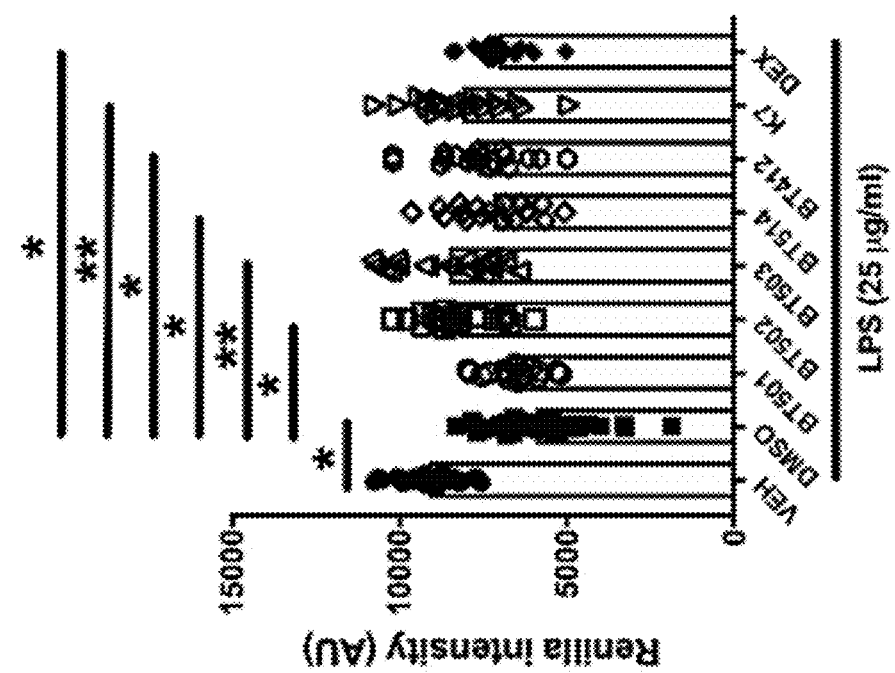
Figure 10B:
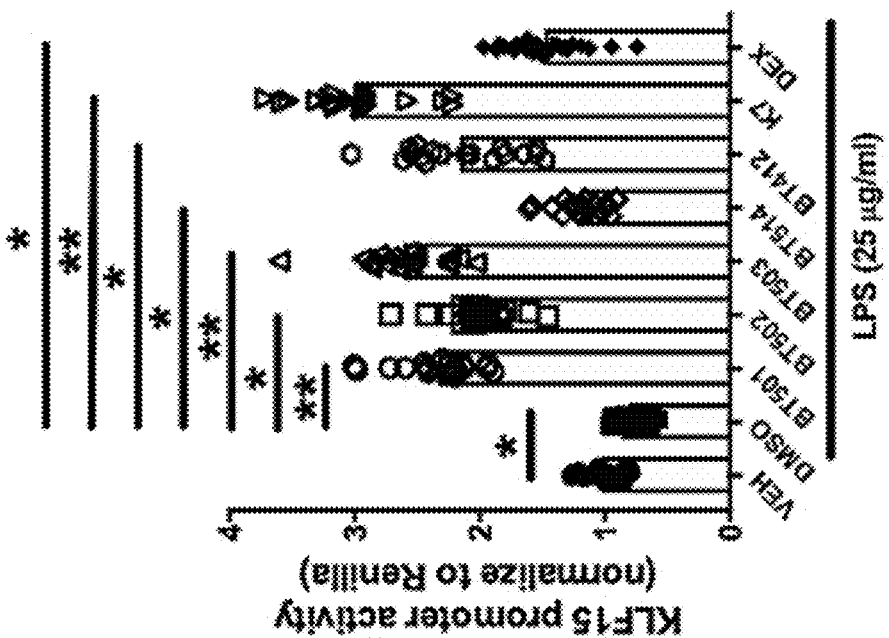

After the synthesis of these novel analogues, a primary screening assay was conducted. It was determined that BT501, BT502, BT503, BT514, and BT412 significantly induced KLF15 reporter activity (with no observed toxicity to human podocytes) (FIG. 9). Based on these data, these analogues were advanced for further testing in a primary screening assay (dose-escalation studies and cell viability) and in a secondary biological assay (podocyte stress model). Dose escalation studies determined that BT503 has an $EC_{50}$~7.1 nM, the lowest as compared to the other analogues and most closely resembling the original lead small molecule (K-7) (FIG. 10A). It was also observed that K-7, BT501, BT502, BT503, and BT412 showed higher maximal KLF15 reporter activity at similar concentrations to DEX (FIG. 10A). Finally, K-7, BT502, BT503, BT514, and BT412 improved KLF15 reporter activity and podocyte survival after LPS treatment (FIG. 10B and FIG. 10C).

Figure 10D:
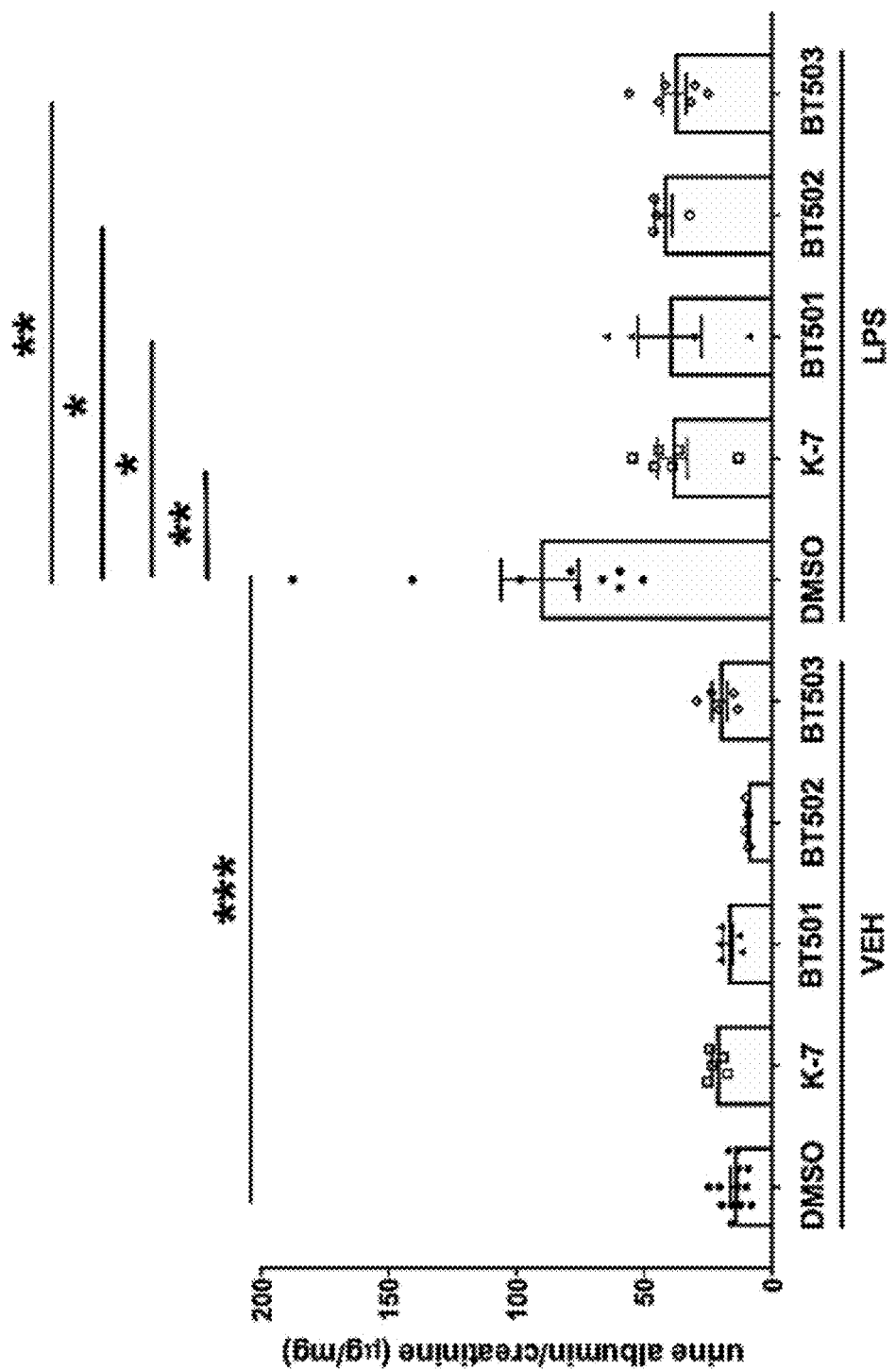

Referring to FIG. 10D, C57BL/6 mice were treated with lipopolysaccharide (LPS) at dose of 10 µg/g in two divided doses 24 hours apart intraperitoneally to induce podocyte injury and albuminuria. Concurrently, mice were either treated with DMSO (control), K-7, BT501, BT502, or BT503 via subcutaneous minipump (cumulative dose of 3.5 µg/day for 48 hours) to assess the therapeutic efficacy of these lead KLF15 agonists in abrogating albuminuria (marker of kidney injury). We observed that K-7, BT501, BT502, or BT503 significantly reduced albuminuria as compared to DMSO-treated mice in this LPS-induced albuminuria murine model.

5. Equilibrium Stability

The equilibrium solubility of three lead compounds (BT501, BT502, BT503) was measured in pH 2.0, 4.0, and 7.4 aqueous buffers. See Table 2 below. The pH 2.0 buffer was prepared by combining 50 mL of 0.2 M KCl with 150 mL of $H_2O$, and then adjusting to pH 2.0 with 10 N HCl. The pH 4.0 buffer was prepared by combining 50 mL of 0.2 M $(KHC_6H_4(COO)_2)$ with 150 mL of $H_2O$, and then adjusting to pH 7.4 with 10 N HCl. The pH 7.4 buffer was prepared by combining 50 mL of 0.2 M $KH_2PO_4$ with 150 mL of $H_2O$, and then adjusting to pH 7.4 with 10 N NaOH. At least 0.3 mg of powder for each lead compound was combined with 1 mL of each buffer to make a ≥0.3 mg/mL mixture. These samples were shaken on a Thermomixer® overnight at room temperature. The samples were then centrifuged for 10 minutes at 14,000 rpm. The supernatant was sampled and diluted in duplicate 10-, 100-, 1,000-, and 10,000-fold into a mixture of 1:1 buffer:acetonitrile (ACN) prior to analysis. All samples were assayed by LC-MS/MS using electrospray ionization against standards prepared in a mixture of 1:1 assay buffer:ACN. Standard concentrations ranged from 1.0 µM to 0.3 nM.

TABLE 2

| Lead Compound | pH | Solubility (µM) | | |
|---|---|---|---|---|
| | | R1 | R2 | AVG |
| BT501 | 2 | 99.7 | 95.7 | 97.7 |
| | 4 | 157 | 148 | 153 |
| | 7.4 | 279 | 258 | 269 |
| BT502 | 2 | 21.8 | 22.6 | 22.2 |
| | 4 | 10.4 | 10.3 | 10.4 |
| | 7.4 | 28.4 | 27.7 | 28.1 |
| BT503 | 2 | 332 | 353 | 343 |
| | 4 | 17.4 | 17.2 | 17.3 |
| | 7.4 | 31.6 | 37.4 | 34.5 |

6. Stability in Phosphate Buffer

Studies were carried out in pH 7.4 phosphate buffer. The buffer was prepared by combining 50 mL of 0.2 M $KH_2PO_4$ with 150 mL of $H_2O$, and then adjusting to pH 7.4 with 10 N NaOH. The buffer was adjusted to pH 7.4 prior to initiating the experiments. A DMSO stock was first prepared for the lead compounds (BT501, BT502, BT503). Aliquots of the DMSO solutions were dosed into 0.5 mL of matrix, which had been pre-warmed to 37° C., at a final lead compound concentration of 1 µM. Individual tubes were dosed for each timepoint. The vials were kept in a benchtop Thermomixer for the duration of the experiment. At each time point (0, 30, 60, and 120 minutes), an equal volume of acetonitrile was added to the appropriate tubes. Samples were stored at 4° C. until the end of the experiment. After the final time point was sampled, the plate was mixed and then centrifuged at 3,000 rpm for 10 minutes. Aliquots of the supernatant were removed, diluted 1:1 into distilled water, and analyzed by LC-MS/MS. The peak area response ratio to internal standard (PARR) was compared to the PARR at time 0 to determine the percent of lead compound remaining at each time point. Half-lives were calculated using GraphPad software, fitting to a single-phase exponential decay equation. See Table 3 below.

TABLE 3

| Lead Compound | Percent Remaining | | | | Half-Life (min) |
|---|---|---|---|---|---|
| | 0 min | 30 min | 60 min | 120 min | |
| BT501 | 100 | 88.4 | 92.1 | 87.7 | >120 |
| BT502 | 100 | 99.7 | 87 | 88.7 | >120 |
| BT503 | 100 | 90.6 | 87.6 | 80.5 | >120 |

7. Stability in Human Liver Microsomes

Mixed-gender human liver microsomes (Lot #1010420) were purchased from XenoTech. The reaction mixture, minus NADPH, was prepared as described below. The lead compounds (BT501, BT502, BT503) were added into the reaction mixture at a final concentration of 1 µM. The control compound, testosterone, was run simultaneously with the lead compounds in a separate reaction. The reaction mixture (without cofactor) was equilibrated in a shaking water bath at 37° C. for 3 minutes. The reaction was initiated by the addition of the cofactor, and the mixture was incubated in a shaking water bath at 37° C. Aliquots (100 μL) were withdrawn at 0, 10, 20, 30, and 60 minutes. Each lead compound and testosterone samples were immediately combined with 400 μL of ice-cold 50/50 acetonitrile (ACN)/H$_2$O containing 0.1% formic acid and internal standard to terminate the reaction. The samples were then mixed and centrifuged to precipitate proteins. All samples were assayed by LC-MS/MS using electrospray ionization. The peak area response ratio (PARR) to internal standard was compared to the PARR at time 0 to determine the percent remaining at each time point. Half-lives and clearance were calculated using GraphPad software, fitting to a single-phase exponential decay equation. See Table 4 below.

9. Evaluation of the Effect of K-7 on Glomerular Injury In Vivo

Figure 22B:
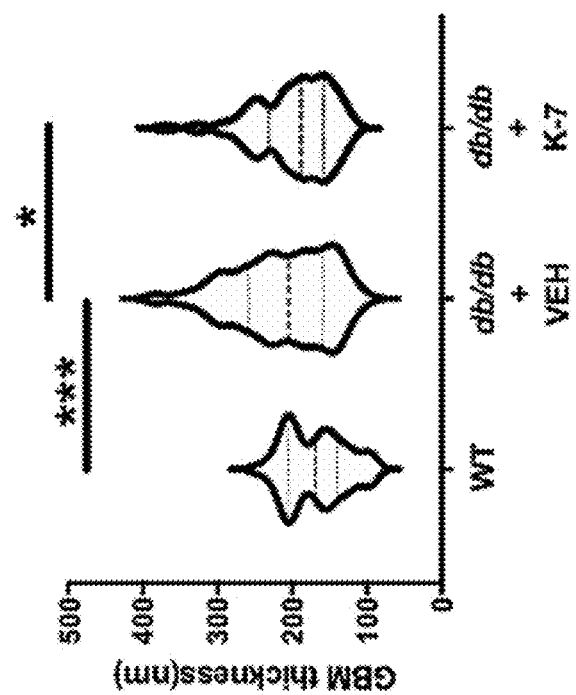
FIG. 22A and FIG. 22B show representative data illustrating that treatment with K-7 improved glomerular injury in a murine model of progressive diabetic kidney disease.
Figure 22A:
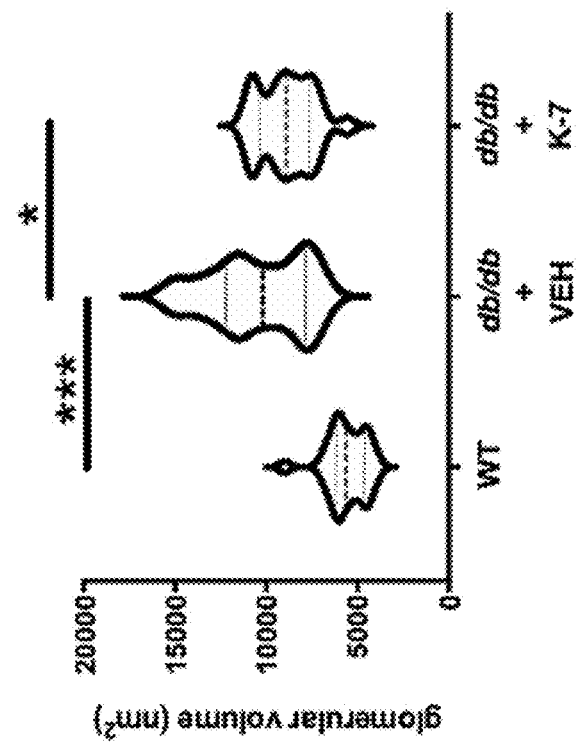

Db/db mice on the FVB/N background were utilized as a murine model of progressive diabetic kidney disease (DKD), where there is significant podocyte injury and glomerulosclerosis. It was observed that K-7 (subcutaneous minipump, cumulative dose of 0.85 μg/day for 14 days) attenuated podocyte effacement and glomerular injury (reduced glomerular volume and glomerular basement membrane (GBM) thickness) as demonstrated by periodic acid-schiff (PAS) staining and transmission electron microscopy (TEM) (data not shown). These findings were subsequently quantified using ImageJ to demonstrate that treatment with K-7 improved glomerular injury as determined by reduced glomerular volume and GBM thickness (FIG. 22A and FIG. 22B).

TABLE 4

| Lead Compound | Percent Remaining | | | | | Half-Life (min) | CLint$^a$ (mL/min/mg protein) |
|---|---|---|---|---|---|---|---|
| | 0 min | 10 min | 20 min | 30 min | 60 min | | |
| BT501 | 100 | 78.1 | 66.4 | 54.2 | 32.5 | 35.8 | 0.0387 |
| BT502 | 100 | 63.9 | 45.3 | 29.6 | 8.53 | 17 | 0.0813 |
| BT503 | 100 | 60.1 | 35.3 | 18.5 | 3.3 | 13 | 0.107 |

$^a$Intrinsic clearance (Clint) was calculated based on Clint = k/P, where k is the elimination rate constant and P is the protein concentration in the incubation.

8. Caco-2 Permeability

Caco-2 cells (clone C2BBe1) were obtained from American Type Culture Collection (Manassas, Va.). Cell monolayers were grown to confluence on collagen-coated, microporous membranes in 12-well assay plates. Details of the plates and their certification are shown below. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 μM of lead compound in the assay buffer. Cell monolayers were dosed on the apical side (A-to-B) or basolateral side (B-to-A) and incubated at 37° C. with 5% CO$_2$ in a humidified incubator. Samples were taken from the donor and receiver chambers at 120 minutes. Each determination was performed in duplicate. The flux of lucifer yellow was also measured post-experimentally for each monolayer to ensure no damage was inflicted to the cell monolayers during the flux period. All samples were assayed by LC-MS/MS using electrospray ionization. The apparent permeability (Papp) and percent recovery were calculated and provided. See Table 5 below.

10. Combined Treatments of KLF15 and Dexamethasone

Figures 23A, 23B:
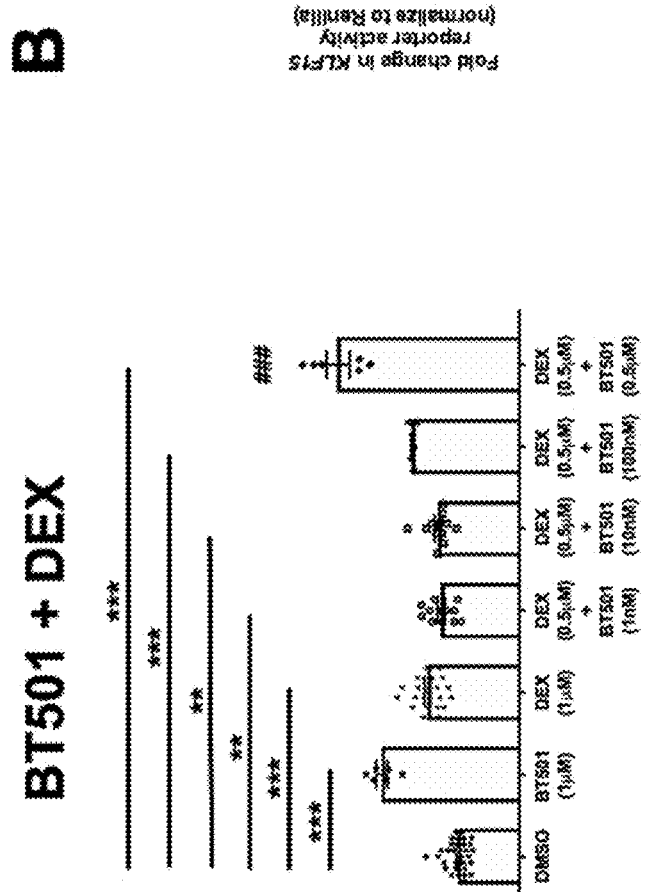
FIG. 23A-C show representative data illustrating that combination treatments involving KLF15 lead agonists (BT501, BT502, BT503) and a glucocorticoid offer synergistic results.
Figure 23C:
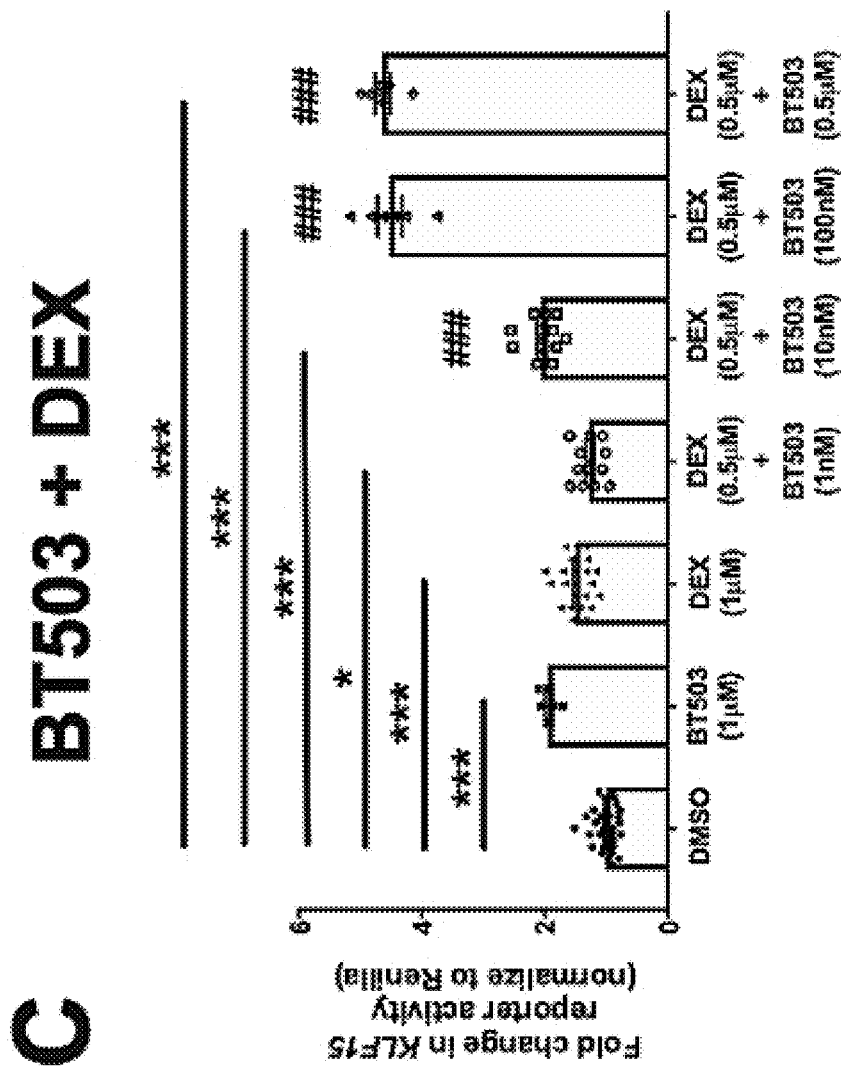

To assess whether KLF15 lead agonists (BT501, BT502, BT503) reduce the dose of glucocorticoids required to induce KLF15 promoter activity, human podocytes were treated with each of the lead compounds at increasing doses (1 nM, 10 nM, 100 nM, and 0.5 μM) in combination with low dose dexamethasone (DEX) (0.5 μM). Without wishing to be bound by theory, it was observed that each of the lead compounds and DEX (1 μM) significantly induced KLF15 promoter activity as compared to DMSO-treated human podocytes (FIG. 23A-C). In addition, each of the combination regimens (lead compound+DEX (0.5 μM)) also induced KLF15 promoter activity as compared to DMSO-treated human podocytes (FIG. 23A-C). The combination of lower doses of BT501 (0.5 μM)+DEX (0.5 μM) had a synergistic effect on inducing KLF15 promoter activity as compared to the higher dose DEX (1 μM)-treated human podocytes (FIG. 23A). The combination of lower doses of BT502 (0.5 μM) or BT502 (100 nM) with DEX (0.5 μM) had a synergistic effect on inducing KLF15 promoter activity as compared to the higher dose DEX (1 μM)-treated human podocytes (FIG. 23B). Finally, lower doses of BT503 (0.5 μM), BT503 (100

TABLE 5

| Lead Compound | Direction | Recovery (%) | Papp (10$^{-6}$ cm/s) | | | Efflux Ratio | Absorption Potential Classification | Significant Efflux |
|---|---|---|---|---|---|---|---|---|
| | | | R1 | R2 | AVG | | | |
| BT501 | A-to-B | 66.7 | 32.5 | 38.5 | 35.5 | 0.987 | High | No |
| | B-to-A | 81.7 | 32.5 | 37.6 | 35 | | | |
| BT502 | A-to-B | 63.1 | 14.6 | 15.9 | 15.2 | 0.481 | High | No |
| | B-to-A | 67.1 | 6.35 | 8.33 | 7.34 | | | |
| BT503 | A-to-B | 59.7 | 13.1 | 8.28 | 10.7 | 0.909 | High | No |
| | B-to-A | 69 | 9.06 | 10.3 | 9.7 | | | |

Absorption Potential Classification:
Papp (A-to-B) < 1.0 × 10$^{-6}$ cm/s: Low
Papp (A-to-B) ≥ 1.0 × 10$^{-6}$ cm/s: High
Significant Efflux: ER ≥ 2.0 and Papp (B-to-A) ≥ 1.0 × 10$^{-6}$ cm/s nM), or BT503 (10 nM) in combination with DEX (0.5 µM) had a synergistic effect on inducing KLF15 promoter activity as compared to the higher dose DEX (1 µM)-treated human podocytes (FIG. 23C).

H. ADDITIONAL PROPHETIC EXAMPLES

1. Improve the Pharmacodynamic (PD) and Pharmacokinetic (PK) Properties of KLF15 Agonists.

Figure 11:
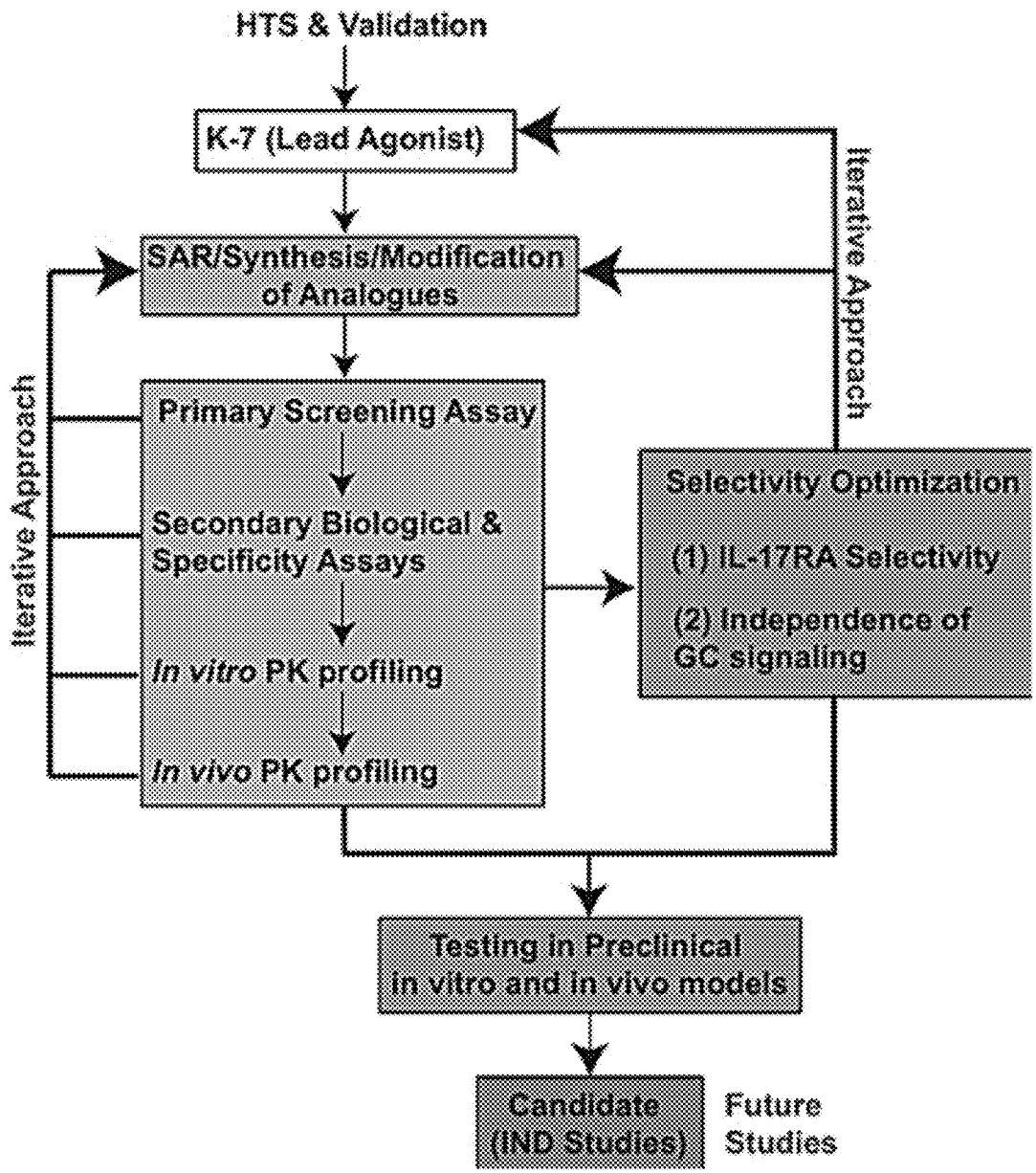
FIG. 11 shows a representative schematic illustrating the proposed lead-optimization workflow to preclinical testing.

The initial data identified a lead KLF15 agonist and structural analogues from a preliminary SAR study that have a therapeutic efficacy in models of podocyte injury (FIG. 2A-F, FIG. 3A-C, FIG. 4A, FIG. 4B, FIG. 5A-D, FIG. 6, FIG. 7A, FIG. 7B, FIG. 8A, FIG. 8B, FIG. 9, and FIG. 10A-C). Based on these data, new K-7 analogues will be synthesized (estimated to be ~100 compounds) to optimize their potency (as defined by $EC_{50}$) and selectivity. The synthesis of novel analogues from the SAR will be dynamic and will be guided by primary screening in cultured human podocytes expressing the KLF15 reporter to determine the $EC_{50}$, which will be followed by secondary biological and specificity assays, with a novel Limited Rationale Design (LRD) approach to modify the structure of lead analogues to limit its cytotoxicity. Next, lead analogues with therapeutic efficacy ($EC_{50}$<100 nM) and a wide therapeutic index (TI>10) will be advanced to conduct an integrated and iterative approach to test scaffold liabilities and optimize druggability with in vitro and in vivo PK profiling assays. FIG. 11 provides an overview of the lead optimization workflow.

a. Determine the SAR of Lead Klf15 Agonists to Generate and Test Modified Compounds Designed to Increase their Efficacy and Specificity.

Rationale, approach, and strategy. As demonstrated from the preliminary data (FIG. 1A-D, FIG. 2A-F, FIG. 3A-C, FIG. 4A-B, FIG. 5A-D, FIG. 6, FIG. 7A-B, FIG. 8A-B, FIG. 9, and FIG. 10A-C), the rationale and feasibility to expand the SAR study of the lead KLF15 agonist (K-7) will be provided to generate novel analogues and to test their efficacy ($EC_{50}$) in inducing KLF15 reporter activity in the primary screening assay and analogues with $EC_{50}$<100 nM will be advanced to secondary biological assays and specificity assays in cultured human podocytes.

As demonstrated in the preliminary data (FIG. 2A-F, FIG. 3A-C, FIG. 4A-B, FIG. 5A-C, FIG. 6, FIG. 7A-B, and FIG. 8A-B), a dynamic and iterative workflow will be proposed where analogues are initially synthesized and purified in a batch of ~15-20 analogues (in milligram quantities) and then their initial efficacy ($EC_{50}$) and cell toxicity (Renilla, MTS assay) will be tested. This real-time information will then be used for modifications of the analogues (go/no-go strategy) (FIG. 11). In addition, this SAR strategy will be supplemented by in-silico modeling for identification of new pharmacophore groups. Although computational in-silico modeling can serve as a guide to identify potential active molecules, it is necessary to complement this with basic medicinal chemistry (with SAR) to develop more biologically active analogues (as demonstrated in the preliminary SAR in FIG. 6). These compounds will be designed using the Lipinski rule of 5 test and with considerations of propensity for (1) biological activity (i.e., more $sp^3$ carbon atoms), (2) ease of synthesis, and (3) moderate compound complexity to guide the molecular design choices that maintains efficacy while mitigating toxicity (24).

Figure 12:
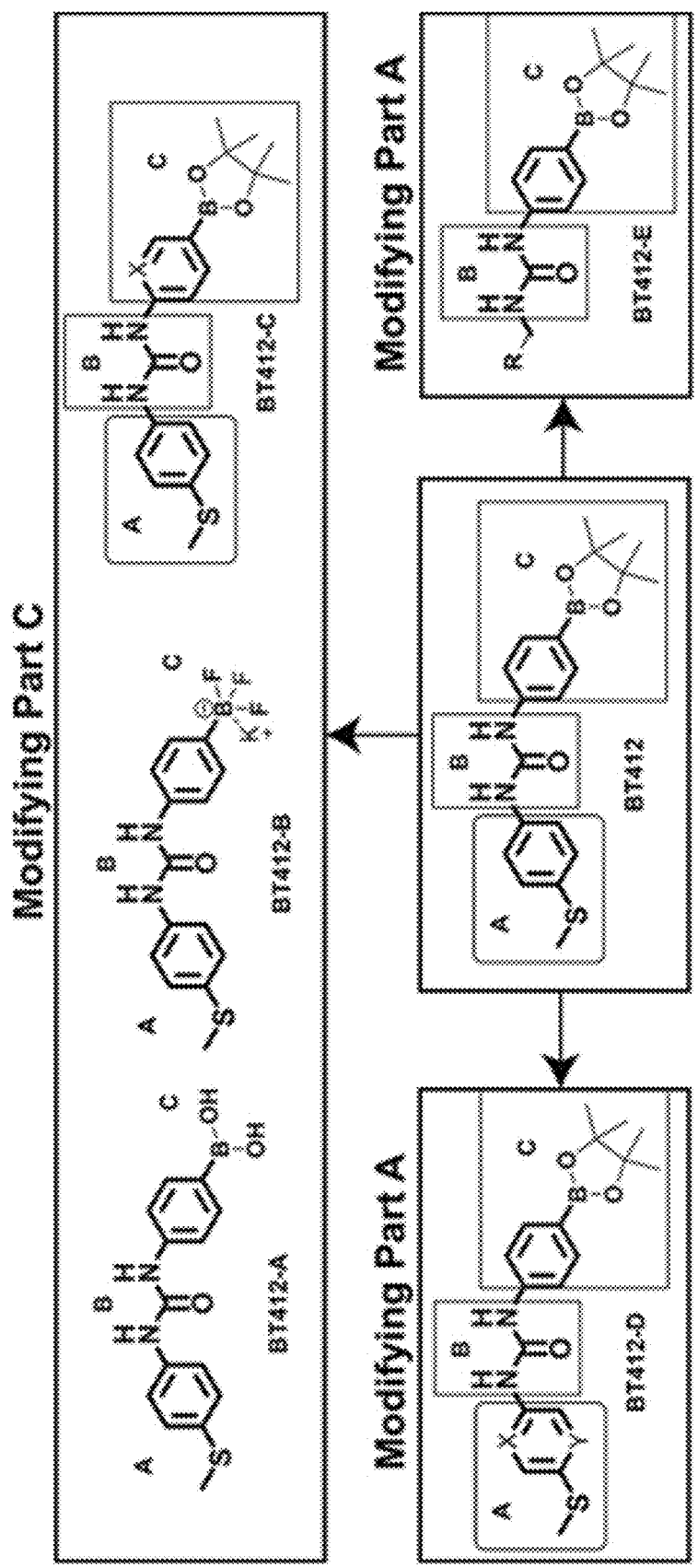
FIG. 12 shows a representative schematic of SAR strategy to modify components A, B, and C of BT412 (analogue from preliminary SAR strategy).

To further demonstrate the feasibility of expanding the SAR, the following hypothesis will be used to generate novel derivatives from BT412 (FIG. 12). BT412 contains a boronic ester moiety (Part C) that will be converted to the boronic acid and the potassium salt of trifluoroborate to increase water solubility and enzyme specificity, leading to synthesis of BT412-A, B, and C series of derivatives. In Part A of BT412, the phenyl substituted thiomethyl group will be converted to heterocyclics (where X and Y are O, N, S) (BT412-D) and the R group in the BT412-E will be converted to aliphatic, aromatics, heterocyclic, imidazopyrine, and other compounds to increase cell permeability. Part B of BT412 will be converted to biological isosteres of urea derivatives. Since the lead agonist (K-7) as well as the initial analogues such as BT412 contain urea derivatives, it is proposed to increase potency while reducing off-target effects by introducing more rigid peptidomimetic compounds as previously reported (23, 25). This will lead to synthesis of additional BT412-F to BT412-M analogs, where, X, Y, and Z are C, O, N, and S atoms. Furthermore, all boronic esters could be further derivatized to boronic acid and potassium salts of trifluoroborate to increase water solubility and cell membrane permeability (FIG. 12).

All compounds will be synthesized using known reactions. If known reactions are not sufficient, new reactions will be developed to synthesize intermediates and then the targeted molecules (go/no-go strategy). After synthesis of novel analogues, each intermediate will be purified, the final compounds will be run through column chromatography, and the stereochemical active compounds will be run through chiral columns. After purification, the chemical structures will be identified using analytical tools such as NMR, HPLC, and HRMS. Compounds that exhibit 97-99% purity will be advanced to the primary screening assay. By using this approach, it is proposed to synthesize ~100 novel KLF15 analogues.

Finally, instead of utilizing a common non-specific approach of HTS, a Limited Rationale Design (LRD) approach will be utilized, which means that rather than screening 10,000-100,000 arrayed compounds that can be extremely costly and time consuming, it is proposed to ultimately generate a small library of only about 20+ novel KLF15 analogues that will ultimately pass through the primary and secondary in vitro assays. Laboratories are well versed in this strategy (26-28). In addition to the cost, there are two critical advantages to the LRD approach: (1) The cell biological assays do not require simplification for high throughput compatibility, and (2) putative "hits" are not obtained at random and are therefore less likely to result from off-target effects that will only be revealed during the elaborate follow-up analysis. Furthermore, pharmaceutical industry usually invests more than $4-5 million and spend 3-4 years for target-to-hit and proof-of-concept studies. However, by using this LRD approach, strong structure-based design, and medicinal chemistry expertise, biologically active novel analogues will be feasibly generated. Thus, the goal of this strategy is to utilize a lead optimization approach (with go/no-go strategy) by expanding the preliminary SAR to generate additional KLF15 analogues with subsequent primary screening and secondary biological and specificity assays.

Computational in-silico modeling. Customized computational protein structure modeling programs (e.g., M4T, MMM, and Mutate) will be used, as well as standard programs (e.g., Autodock4, Surflex-Dock, ICM, PESD, SFC, etc.). ICM (Molsoft. LLC-UCSD) will also be used to study the Structure Toxicity Relationship (STR) of the molecules.

Human podocytes. Differentiation and maintenance of human podocytes will be conducted as previously described. Testing will be done under nonpermissive conditions (37° C., 14 days) (8).

Primary Screening assay. As described in the preliminary data, cultured human podocytes expressing the KLF15 promoter will be used (under nonpermissive conditions) to test the $EC_{50}$ based on the luciferase activity. To determine the $EC_{50}$, dose-response curves ($10^{-4}$ to $10^4$ μM, n=8, 96-well plate format) will be conducted with DMSO (negative control) and DEX (positive control) at similar concentration ranges. Data will be expressed as fold change in reporter activity relative to renilla activity.

Cell viability will be measured by 3 approaches (renilla activity, MTS assay, cell count with flow cytometry). Since the human podocyte assay expresses renilla concurrently, this will be utilized to measure cell viability at the specified doses in the primary screening assay. Concurrently MTS assay and cell count with flow cytometry will be utilized to validate cell viability. Combined with the dose-response curves in the primary screening assay and these three measurements of cell viability, max., and min. safe dose, the Therapeutic Index (TI) to induce KLF15 will be determined. TI will be calculated based on the ratio of 50% of toxic dose ($TD_{50}$) to $EC_{50}$. The optimal TI>10 that limits toxicity and off-target effects is based on previously reported data (29).

Secondary biological assays. In the analogues that passed the criteria from primary screening assay, KLF15 mRNA (quantitative RT-PCR) and protein (Western Blot) expression will be measured. Markers of mature podocytes (Synaptopodin, NPHS1, NPHS2, WT1) and actin stress fiber formation (phalloidin staining) will later be tested in three established cell culture models of podocyte injury (LPS, adriamycin, and puromycin) as previously reported (8, 9, 16).

Specificity assays. To determine that the designed analogues from the lead optimization are specific to KLF15, changes in expression of other members in the KLF family that have been previously to be expressed in podocytes will be tested (30). Concurrently, specificity to KLF15 can be determined using an unbiased approach through RNA-seq and iTRAQ proteomics. Briefly, RNA-seq data will be processed as previously described (10). Read counts will be normalized to count per million (CPM) and differentially expressed genes will be identified using the Characteristic Direction method (31). Enrichment analyses of the differentially expressed genes will also be performed with Enrichr (32, 33).

iTRAQ proteomics. Mass spectroscopy and bioinformatic analysis will be performed. Protein changes will be measured by trypsin digestion, iTRAQ stable isotope incorporation, and in line cation-exchange (SCX) reverse phase (C18) fractionation with LC-MS/MS. iTRAQ labeling (8plex chemistry) is performed under established conditions, peptides desalted, lyophilized, resuspended in 0.1% formic acid and analyzed by SCX-C18-MS/MS. Parent peptide mass, collision-induced fragment mass information and isotopically-encoded peptide abundance values are obtained nanoLC-MS/MS, using both an orbital trap (Thermo QE-HF) and an orthogonal quadruple TOF instrument (AB-Sciex 5600+). Protein abundance and peptide phosphorylation site abundance will be established by protein database searching using the Proteome Discoverer and ProteinPilot (v5.01), followed by statistical analysis using R and JMP12.

b. Utilize an Integrated and Iterative Approach (Absorption, Distribution, Metabolism and Excretion (ADME) and Toxicity Screens) to Test the Scaffold Liabilities and Optimize Druggability of these Candidate KLF15 Agonists In Vitro and Perform In Vivo PK Profiling on these Top Candidates.

Rationale, approach, and strategy. By utilizing a bioinformatic approach, it was demonstrated that K-7 exhibits optimal absorption, distribution, metabolism, and excretion (ADME) and PK properties for a lead molecule (see Table 1). Here, it is proposed to conduct an initial in vitro pharmacokinetic (PK) profiling to assess the drug-like properties of analogues that met the criteria for advancement as detailed above ($EC_{50}$<100 nM, greater than two-fold change in KLF15 reporter activity, and TI>10). To that end, it is proposed to utilize (1) ADME screen to determine solubility, stability, cell permeability, and protein binding, (2) toxicity screen to assess genotoxicity and tissue toxicity (hepatotoxicity and cardiotoxicity, since these are common reasons for removal of drugs from the market (34)) (3) CYP-450 inhibition/induction assay to assess drug-drug interactions, and (4) Eurofins/Cerep PanLabs assay to assess off-target effects and selectivity. Without wishing to be bound by theory, the goal of these studies is to optimize compounds that are likely to succeed, while reducing the risk of advancing compounds that might fail in in vivo PK studies and in vivo pre-clinical studies (go/no-go strategy).

It is proposed to advance analogues for in vivo PK profiling studies that meet the optimum threshold (based on criteria defined by the FDA) in the in vitro ADME (defined as solubility >10 μM, liver microsomal stability $t_{1/2}$>30 minutes, cell permeability $1 \times 10^{-6}$ cm/s, and protein binding <98%), toxicity (AMES—negative, micronucleus—negative, HepG2 cytotoxicity of $IC_{50}$>100 μM, hERG binding $IC_{50}$>10 μM), drug-drug interactions ($IC_{50}$>10 μM), and off-targets studies (<50% off-target inhibition) (Table 6 and FIG. 11). In these studies, male and female mice on two strains (FVB/N and 129SV/J, both mice with known susceptibility to pre-clinical proteinuric murine models) will be treated to escalating doses (5, 10, 50, 100, 500, 1000 pg/ul) of lead analogues via three different routes (oral, IP, and IV). Serum, urine, kidney, and brain (assess blood-brain permeability) tissue from these mice will be collected (at the specified time intervals) and will be analyzed by LC-MS/MS to determine the $t_{1/2}$ of the intact compound, metabolites, and oral bioavailability. Lead analogues that meet the criteria of $t_{1/2}$>60 min and oral bioavailability of >25% will be defined suitable for preclinical testing (go/no-go criteria). Finally, the novel KLF15 agonists (that pass through the preceding initial PK studies) will be labeled with radiotracer and image using PET to determine the regional biodistribution, the ability to accumulate in the kidney, and the optimal dosing parameters. Feasibility of radiolabeling was demonstrated with the lead KLF15 agonist (K-7) as detailed further below. Without wishing to be bound by theory, the goal is to utilize an integrated and iterative approach (with in vitro and in vivo PK profiling) to test the scaffold liabilities and optimize druggability of the top candidate KLF15 agonists.

TABLE 6

|  | Minimum Criteria |
|---|---|
| In vitro PK profiling | |
| In vitro permeability | $1 \times 10^{-4}$ cm/s |
| CYP450 Inhibition | >10 μM |
| Solubility | >10 μM |
| Liver microsomal stability ($t_{1/2}$) | >30 minutes |
| Protein binding | <98% |
| AMES | Negative |

TABLE 6-continued

| | Minimum Criteria |
|---|---|
| hERG activity | >10 μM |
| Micronucleus | Negative |
| HepG2 cytotoxicity | >100 μM |
| Drug-drug interactions | >10 μM |
| Off-target effects | <50% |
| In vivo PK profiling | |
| $t_{1/2}$ | <60 min |
| Oral bioavailability | >25% |
| Specificity of radiotracer to kidney | Yes |
| BBB permeability | No |

ADME assay (Eurofins Inc.). Briefly, stability of compounds will be conducted in liver microtomes (human and mouse) to account for interspecies variability. Solubility will be determined in buffered PBS (pH~7.4), ratios of DMSO/PBS, and simulated gastric and intestinal fluid. Protein binding will be determined by rapid equilibrium dialysis and absorption and cell membrane permeability will be conducted using Caco2 cells (typical cell line used for these studies (35)).

Toxicity screening assay (EuroFins Inc.). Toxicity of K-7 and lead analogues will be determined using the AMES and micronucleus assays (assess genotoxicity and the potential for mutagenesis), cardiotoxicity (using hERG screening), and hepatotoxicity (using HepG2 cells). Specifically, AMES assay will be used to measure DNA damage, micronucleus assay will be used to measure extent of double-stranded DNA breaks and disruption of mitotic cell division as previously reported (36), with positive control (mitomycin C). Cardiotoxicity will be determined using conventional patch-clamp assay to measure percent inhibition of the amplitude of hERG K+ channel current in KLF15 agonists as compared to E-4031, positive control. Hepatoxicity will be assessed in HepG2 cells and mitochondrial toxicity will be measured using seahorse assay, oxidative stress (DHE staining), and apoptosis (annexin V/PI FACS).

CYP-450 inhibition/induction assay. The extent that individual CP-450 isoforms contribute to the metabolism (via inhibition or induction) will be evaluated using recombinant CYPs for isoforms (3A4, 2B6, 2D6, 1A2, 2C8, 2C9, 2C19) and by measuring $IC_{50}$ as previously reported (37).

Blood-brain permeability. Brain tissue will be tested for deposition of KLF15 lead analogues and metabolites using LC-MS/MS.

Eurofin/Cerep Pan Labs assay. This assay will be utilized to assess off-target liabilities of lead analogues. This commercially available panel from Eurofins Inc. consists of 44 targets (such as kinases, ion channels, GPCRs, transporters, nuclear receptors) and is typically recommended for testing by the FDA and industry in a serum-free cell-based assay. % inhibition will be calculated for each of the 44 off-targets in each of the KLF15 analogues.

LC-MS/MS to determine compound activity. Briefly, samples will be injected in a volume of 10 μL into a C18 (2) LC column and separated by Ultimate 3000 System. After chromatographic separation using a multiple step gradient, mass spectrometry (MS) measurements will be performed on a TSQ Quantum Access MAX Triple-Stage Quadrupole Mass Spectrometer. In addition, to determine biologically active metabolites from the parent compound, MS spectra will be generated by collision-induced dissociation of the metabolite ions at normalized collision energy of approximately 35 eV according to the parent compound (as shown in FIG. 4A and FIG. 4B).

Figure 13A:
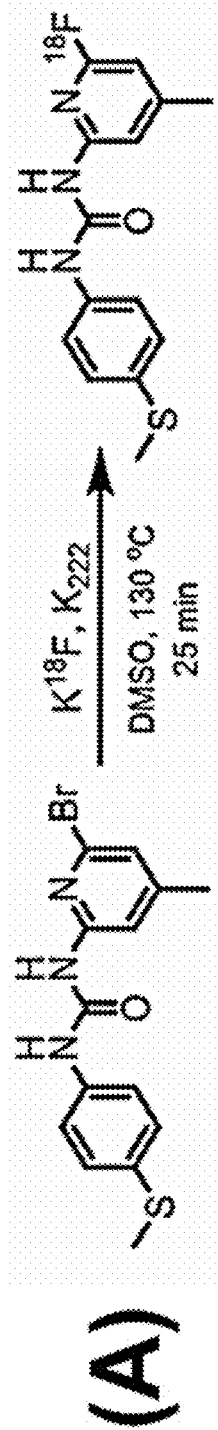
FIG. 13A and FIG. 13B show representative schema for radiolabeling of K-7 with 2-fluoro-pyridine (Step 1, FIG. 13A and Step 2, FIG. 13B).
Figure 13B:
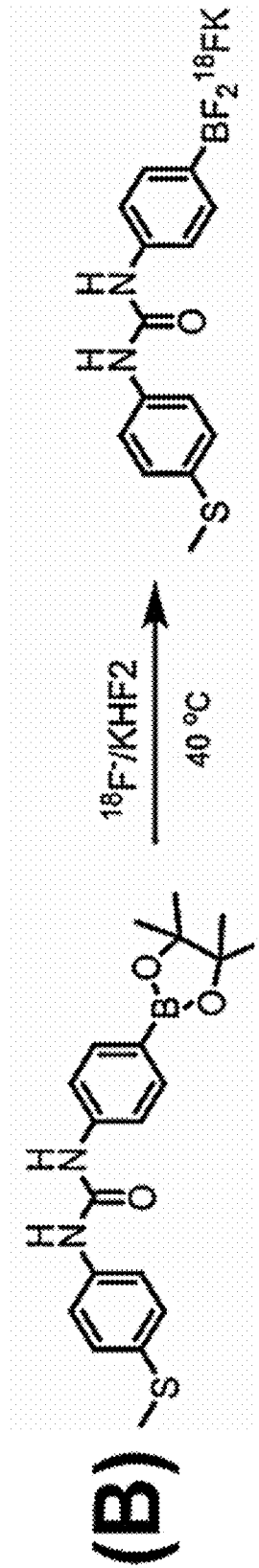

Strategy for radiolabeling of KLF15 agonists (K-7 and BT412). The proposed radiochemical synthesis will be performed according to scheme 1A and 1B in FIG. 13A and FIG. 13B. The radiolabeling of 2-fluoro-pyridine moiety (scheme 1A) has been well established and will be performed as previously reported (38) in one step by reacting the bromopyridyl derivative with $K^{18}F$. Additionally, the drug candidates that contain the dioxaborolan-2-yl moiety will be radiolabeled similar to previous studies (39). The HPLC separation methods will be developed and the radiolabeling and subsequent purification and quality control experiments performed to confirm the identity, to determine radiochemical purity, and to determine the specific activity of each tracer. A similar strategy will be employed for novel KLF15 analogues that advance through the stages of lead optimization.

PET imaging studies. PET imaging studies will be performed in mice similar to previous studies (40, 41). Mice will be anesthetized, placed in the microPET, and injected through the tail vein with ~0.1 mCi of tracer/mouse (n=8/tracer). Dynamic PET (Siemens Inveon, available at SBU core facility) imaging will be performed with emission data acquired initially for 180 min to determine tracer regional biodistribution and to test its ability to accumulate in the kidney. Specific targeting will also be determined via blocking study with the cold unlabeled compound. In addition, this will be used to determine the optimal dosing parameters via a dose curve (to establish the amount of cold drug needed to fully block the specific accumulation of the tracer in the injured kidney). The time-activity curve (TAC) and % injected dose per gram (% ID/g) and standard uptake values (SUV) will be calculated in the kidneys, and all visible major organs. Also, an ex-vivo biodistribution study will be performed by excising major organs and then counting the radioactivity using a gamma counter.

Alternative strategies. Radiotracer labelling experiments are expected to provide spatial resolution on specificity of KLF15 agonists as well as to provide a quantitative information on dosing parameters (to determine $t_{1/2}$), especially since LC-MS measurements can be challenging due to breakdown of parent compound to metabolites. However, it is recognized that radiolabeling of the compound can alter its biological activity. As such, efficacy and toxicity of radiolabeled analogues will be validated as compared to the parent compound.

2. Utilize a Mechanistic Approach to Optimize Selectivity of Klf15 Agonists.

Figure 14A:
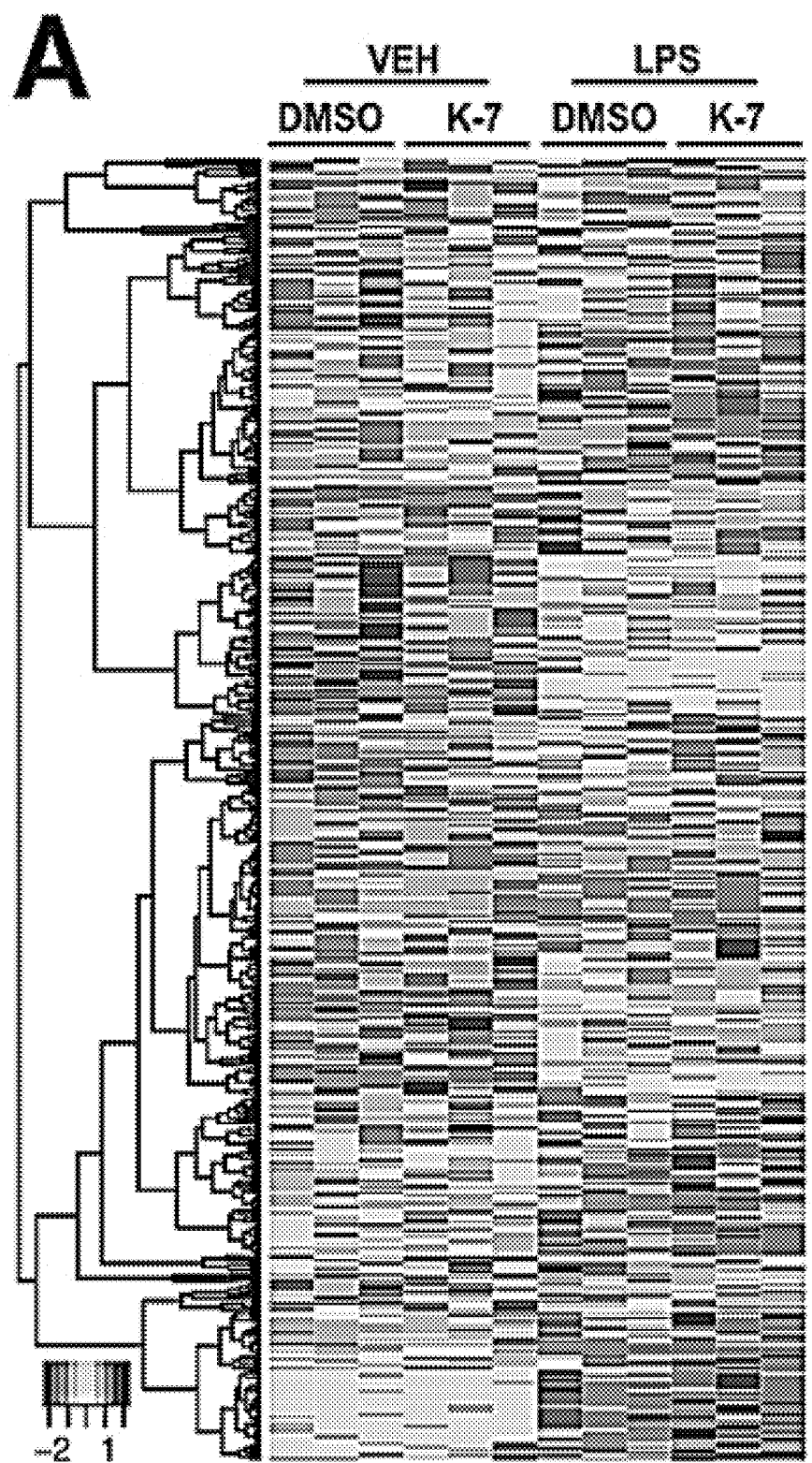
FIG. 14A-C show representative data illustrating the heatmap of DEGs between all four groups (FIG. 14A), gene enrichment analysis of downregulated DEGs in K-7, LPS as compared to DMSO/LPS-treated groups (FIG. 14B), and ChIP-enrichment analysis of DEGs (up and down between K-7/LPS and DMSO/LPS groups) shows binding sites for KLF15 (FIG. 14C).
Figure 14B:
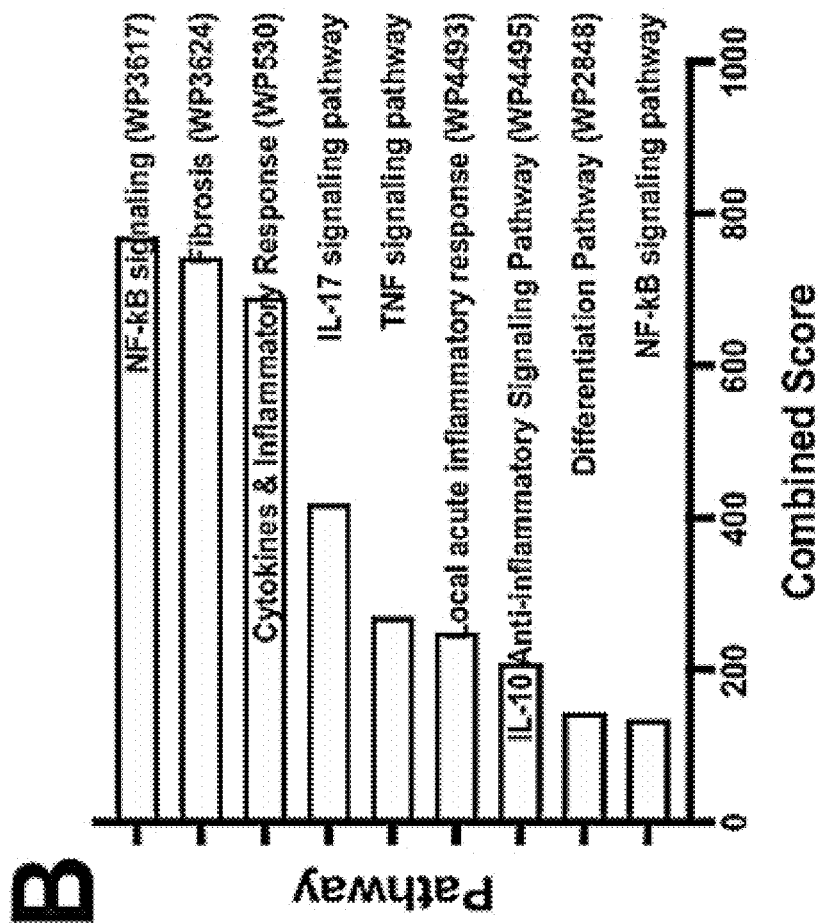
Figure 14C:
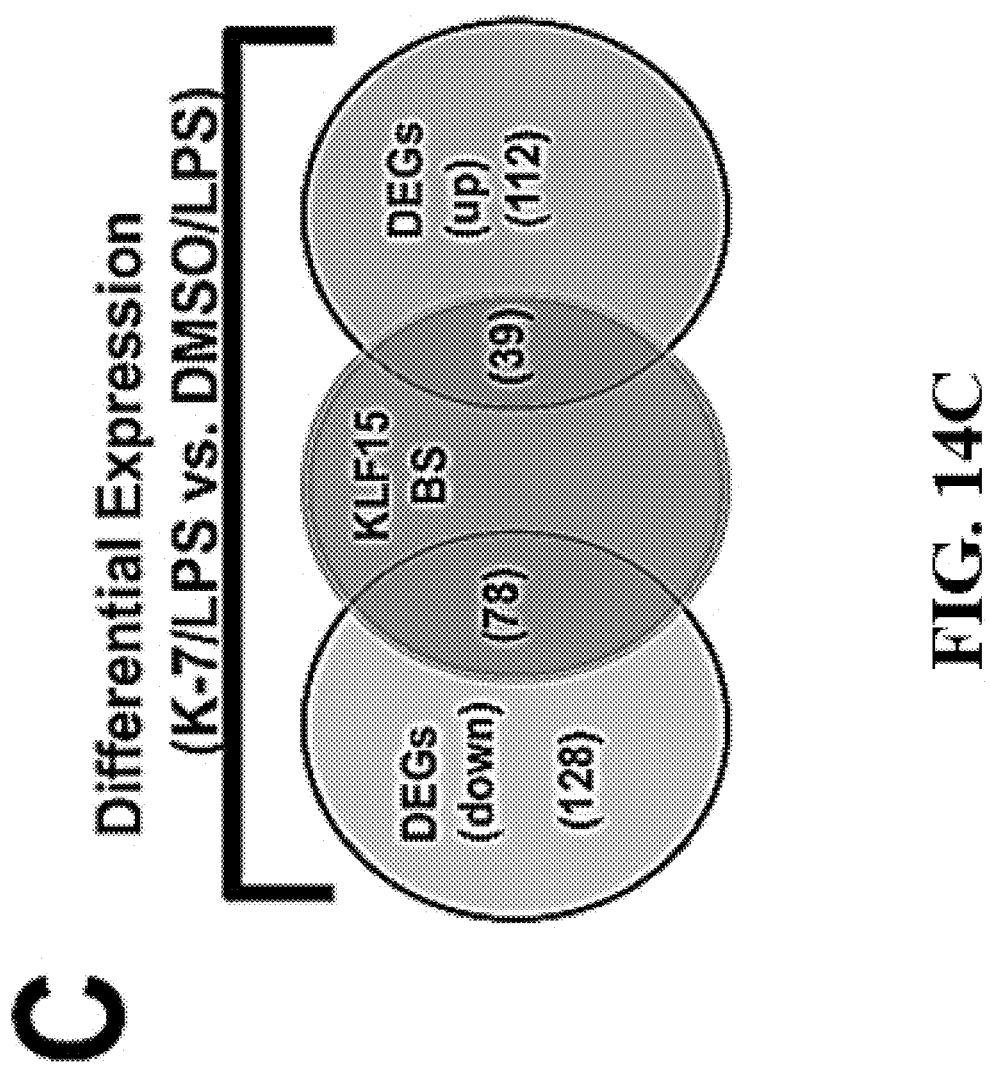
Figure 15:
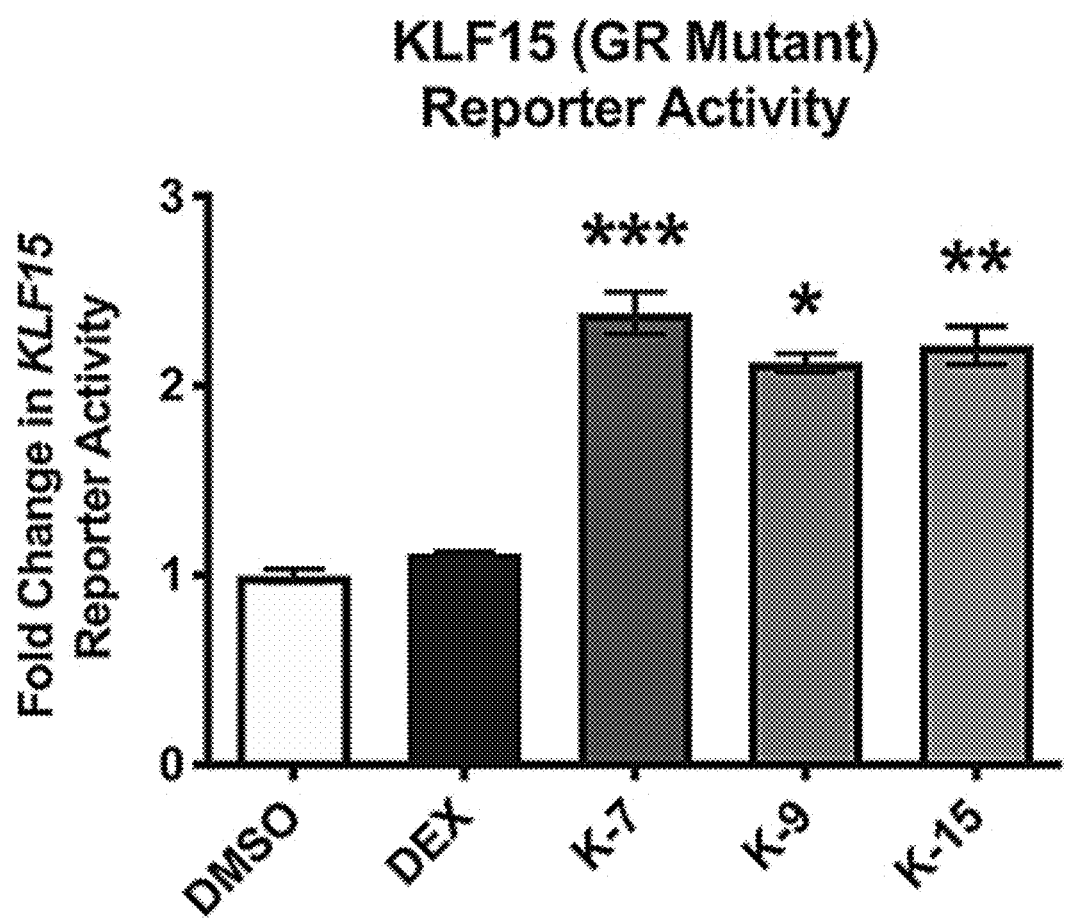
FIG. 15 shows representative data illustrating KLF15 reporter activity for lead KLF15 agonists K-7, K-9, and K-15 using GR-mutant reporter assay.

Preliminary data shows that the lead KLF15-agonist and related analogues (BT501, BT503, BT514, and BT412) demonstrate induced KLF15 promoter activity as well as improve podocyte survival under cell stress (FIG. 9 and FIG. 10A-C). To address the mechanism by which KLF15 expression is induced, RNA-seq was conducted on human podocytes treated with and without K-7 in the setting of LPS/DMSO (FIG. 14A). Subsequent, gene enrichment analysis was performed on differentially expressed genes (DEGs) downregulated in K-7 as compared to DMSO in LPS-treated podocytes against the gene set libraries: WikiPathways (42), and KEGG pathways (43). This revealed a significant decrease in genes involved in IL-17R and NF-κB signaling pathways, chemokine/inflammatory signaling, and fibrosis pathways (FIG. 14B). Interestingly, ChIP-enrichment analysis demonstrated that KLF15 binding sites occupy the promoter region of the majority of these DEGs involved in IL-17R signaling, suggesting direct and indirect mechanisms by which KLF15 regulates these genes (FIG. 14C). Since it was previously reported that glucocorticoid-response elements (GRE) occupy the promoter region of KLF15, the KLF15 promoter was mutated at the GR binding site and the initial leads (K-7, K9, K-15) were tested to demonstrate that they all induce KLF15 reporter activity independent of GR signaling (FIG. 15).

It is also proposed to optimize the selectivity of the lead analogues by utilizing the IL-17RA structure to optimize the selectivity of novel KLF15 agonists that induce KLF15 through direct inhibition of IL-17RA activity, and subsequently, utilizing the mechanism by which salutary effects of KLF15 agonists in podocytes are mediated through KLF15 and independent of GC signaling.

a. Utilize IL-17RA Structure to Optimize the Selectivity of Novel KLF15 Agonists that Induce KLF15 Through Direct Inhibition of IL-17RA Activity.

Figure 16:
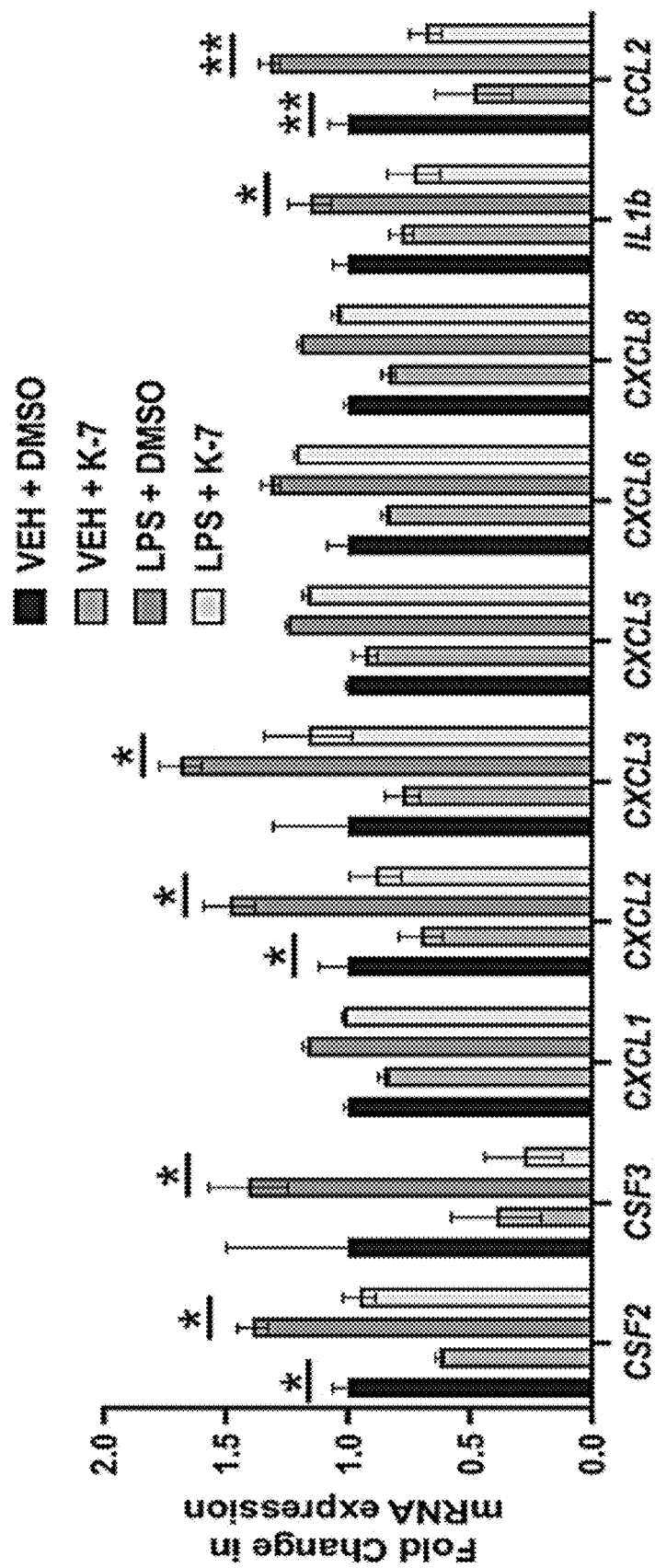
FIG. 16 shows representative data illustrating fold change in mRNA expression of genes downstream of IL-17RA signaling in human podocytes in four groups (VEH+DMSO, VEH+K-7, LPS+DMSO, and LPS+K-7).
Figure 17:
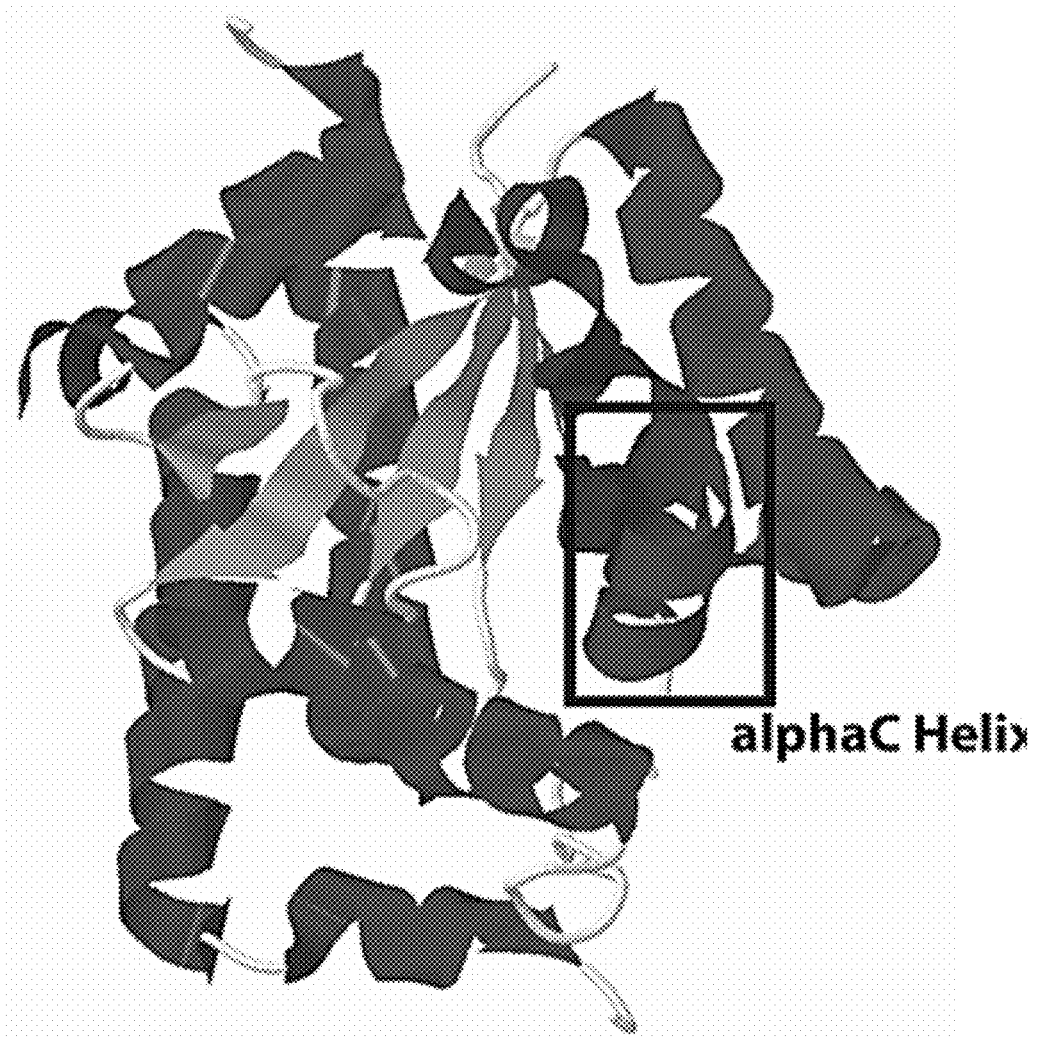
FIG. 17 shows a representative crystal structure illustrating the secondary structure of IL-17RA with location of alphaC Helix (location of NF-κB activator protein binding) and residues for mutation.

Rationale, approach, and strategy. It was observed that K-7 suppressed several key transcripts downstream of IL-17R signaling in cultured human podocytes in the setting of LPS treatment (CSF2, CSF3, CXCL2, CXCL3, CCL2, IL1β) (FIG. 16). Interestingly, other laboratories have recently reported the detrimental role of activated IL-17RA signaling in models of podocyte injury (44). Furthermore, genetic loss of function studies on IL-17RA attenuated podocyte injury in these models (45). In addition, activated IL-17RA signaling suppressed KLF15 expression through NF-κB signaling (46, 47). Collectively, this demonstrates a potential mechanism by which K-7 mediated inhibition of IL-17RA leads to induction of KLF15, leading to stabilization of actin cytoskeleton in the setting of cell stress. Based on the x-ray crystal structure of the receptor binding pocket of IL-17RA (PBD ID: 4NUX) (FIG. 17), it was recently identified that mutations in the alphaC helix of IL-17RA (residues: T483A/N488A/M489A), location of NF-κB activator 1 protein binding and upstream mediator of KLF15, significantly diminished downstream signaling of IL-17RA (48).

Based on these data, it is now proposed to optimize selectivity through the following experiments to test that the direct binding of K-7 and lead analogues to IL-17RA suppresses KLF15 expression: (1) Mutate select residues (T483A/N488A/M489A) on the alphaC helix of IL-17RA (IL-17RA$^{KT}$) and assess for KLF15 induction and the salutary effects of K-7 and lead analogues in human podocytes. Markers of podocyte injury, IL-RA signaling, KLF15 promoter activity and expression will also be measured for. (2) Test the binding affinity and receptor activity of wildtype IL-17RA and IL-17RA$^{KT}$ in the setting of treatment with K-7 and lead analogues by homogenous ELISA-like solid phase binding and surface plasmon resonance (SPR) assays, respectively. (3) Utilizing the go/no-go decision-making approach, results from these studies will be used to optimize lead analogues using GLIDE molecular docking program (Schrödinger Inc.) and Molsoft ICM to enhance the selectivity of IL-17RA inhibition by identifying analogues with higher docking score (Kd>7.0). Without wishing to be bound by theory, the goal is to utilize a mechanistic approach to optimize the selectivity of lead KLF15 analogues to advance for testing in preclinical murine models.

b. Utilize a Mechanistic Approach to Optimize the Selectivity of Novel KLF15 Agonists by Determining that the Salutary Effects of Lead KLF15 Agonists are Independent of GC Signaling.

Rationale, approach, and strategy. Since a major goal of novel therapeutics in proteinuric diseases is to mitigate the use of chronic GCs, it is essential that the selectivity of lead KLF15 analogues is optimized for their salutary effects independent of GC signaling. As demonstrated in FIG. 15, K-7 and lead analogues induce KLF15 reporter activity independent of GC signaling. As such, the following experiments are proposed to test that the salutary effects of K-7 and lead analogues are mediated through KLF15 and independent of GC signaling: (1) Test that KLF15 induction and the salutary effects of K-7 and lead analogues are not dependent on GR signaling using human podocytes with and without GR knockdown under LPS treatment. (2) Test that the salutary effects of K-7 and lead analogues are dependent on KLF15 using human podocytes with and without KLF15 knockdown under LPS treatment. (3) Utilizing the go/no-go decision-making approach, results from these studies will be used to optimize lead analogues to enhance the selectivity of KLF15 agonists that are independent of GR signaling and dependent of KLF15 signaling. Without wishing to be bound by theory, the goal is to utilize a mechanistic approach to optimize the selectivity (independent of GR signaling) of lead KLF15 analogues in the treatment of podocytopathies, independent of toxicity associated with chronic GC use.

Human podocytes. These will be grown under nonpermissive conditions for all studies as described above.

Mutant IL-17RA residues. These will be performed using a Crispr/Cas9-based system to mutate T483A/N488A/M489A in cultured human podocyte.

IL-17RAM and control podocyte lines. These will be conducted with Crispr/Cas9 based system using methodology previously described (49).

ELISA-like solid phase binding and SPR assays. These will be conducted to assess the binding affinity and receptor activity of IL-17RA in the setting of treatment with K-7 and lead analogues using methodology recently described (50-52).

Assess downstream IL17-RA mediated gene expression. This will be determined by measuring downstream gene expression based on the preliminary data in FIG. 16 (CSF2, CSF3, CXCL2, CXCL3, CCL2).

Assessment of podocyte injury. This will be conducted as detailed elsewhere herein.

Alternative strategies and future directions. (1) Based on the results of the binding affinity between KLF15 agonists and IL-17RA, future studies will focus on the identification of additional new scaffolds for inhibition of IL-17RA. Although the initial HTS was based on identification of KLF15 agonists, it was determined that the lead KLF15 agonist (K-7) mediates its effects upstream by potentially binding to cell surface receptor (IL-17RA), which is technically an easier target of action for a small molecule than a transcription factor that resides in the nucleus. As such, the go/no-go approach will utilize molecular docking programs (GLIDE, Molsoft) to expand the identification of additional binding pockets on IL-17RA for synthesis of novel scaffolds. Finally, future studies will focus on expanding these studies to identify additional scaffolds by LRD approach as well as by virtual screening ZINC databases (containing over 3 million compounds) as is typically used by industry. (2) Based on previous studies and preliminary data in the LPS model, inhibition of IL-17RA in the setting injury will be renoprotective. However, chronic inhibition is likely not beneficial as it is important for host defense mechanisms against bacterial and fungal infections. As such, the toxicity studies detailed herein will help mitigate these concerns.

3. Test the Therapeutic Role of Lead KLF15 Agonists in Mitigating and/or Reversing Kidney Injury in Preclinical Proteinuric Models.

Preliminary data suggests that novel KLF15 analogues exhibit salutary effects in cultured human podocytes under cell stress (FIG. 10A-C). Furthermore, it was demonstrated that K-7 restored KLF15 and synaptopodin expression, while restoring actin stress fiber formation in the setting of LPS treatment (FIG. 5A-D). In addition, it was observed that K-7 attenuated albuminuria in LPS-treated mice (FIG. 5A-D). Based on these data, it is now proposed to test the salutary role of novel KLF15 agonists in mitigating and/or reversing kidney injury in preclinical in vitro models (cultured human podocytes, human kidney organoids), and murine models (toxin-mediated (ADR, LPS), anti-glomerular antibody, HIV-1 transgenic (Tg26 mice)) of proteinuric diseases. Although GCs are often the initial therapy for primary glomerular diseases, they are riddled with systemic toxicities. As previously stated, it was recently reported that the salutary benefits of GCs in the podocyte are mediated, in part, by KLF15 (9). Furthermore, no significant systemic toxicity was observed with hKLF15 in mice (either with cell-specific induction using the Pod-rtTA mice or globally with CAG-rtTA mice) (10). In addition, it was observed that podocyte-specific induction of hKLF15 attenuated kidney injury in two preclinical proteinuric murine models (Tg26 mice (FIG. 1A-D), ADR-nephropathy (10)). Based on these data, it is proposed to test the hypothesis that novel KLF15 agonists minimize the cumulative GC dose necessary for its therapeutic effects in these preclinical models.

a. Determine the Therapeutic Effects of Lead KLF15 Agonists in Mitigating and/or Restoring Podocyte Injury in Human Podocytes and Preclinical Patient-Derived Human Organoids and Proteinuric Murine Models.

Rationale, approach, and strategy. Since an effective assay was developed using cultured human podocytes to screen and identify novel KLF15 agonists, this platform was initially utilized to demonstrate that treatment with lead KLF15 agonist (K-7) and analogues derived from the initial SAR restored KLF15 reporter activity in the setting of LPS treatment (FIG. 10A-C). Based on the KLF15 agonists (K-7, BT502, BT503, BT514, and BT412) that advanced from these studies, it is now proposed to validate these findings in human podocytes (under nonpermissive conditions) under an established podocyte injury model (puromycin aminoglycoside (PAN) treatment (16)) and assess for markers of podocyte injury, actin stress fiber formation, and podocyte loss.

Although the protective effects of KLF15 agonists were observed in cultured human podocytes (FIG. 10A-C), a major gap in the field is the lack of reliable in vitro models that recapitulate human proteinuric disease (53), which might contribute to many small molecules failing in the later stages of the drug discovery pipeline. Recent studies demonstrate the potential for human kidney organoids to serve as a platform for testing efficacy of small molecules (54). Based on this, it is proposed to test the efficacy of lead analogues in iPS-derived kidney organoids in the setting of podocyte injury (with and without PAN treatment). To demonstrate feasibility of human organoids to serve as viable platform to test the KLF15 agonists, immunostaining and single-cell RNA sequencing (scRNA-Seq) were conducted to demonstrate the presence of podocytes and tissue organization, an improvement from cell culture models. The initial focus is to test the KLF15 agonists (K-7, BT502, BT503, BT514, and BT412) that advanced from the preliminary SAR (FIG. 6, FIG. 7A-B, FIG. 8A-B, FIG. 9, and FIG. 10A-C). However, both of these in vitro platforms will be utilized for future studies to test the novel analogues that advance through the lead optimization (go/no-go strategy) (FIG. 11).

It is also propose to test the salutary benefits of K-7 and these lead KLF15 analogues in preventing and reversing kidney injury in established preclinical murine models (LPS (short-term study, 48 hours), anti-glomerular antibody (mid-term study, 2 weeks), and Tg26 mice (long-term study, 4 weeks)). To demonstrate feasibility, all of these models have been utilized to study the role of KLF15 in proteinuric diseases (9, 10). Furthermore, preliminary data that treatment with K-7 attenuated proteinuria and restore podocyte markers of injury in LPS-treated mice is provided (FIG. 5D). It was observed that dosing of K-7 every 12 hours (q12 hr, 5 mg/kg, IP) was effective at lowering albuminuria, and, therefore, will be the starting dosing regimen in all 3 preclinical models (details of duration of each model is described herein below). However, it is recognized that PK studies during the lead optimization will be utilized to optimize the dose, frequency, and route of administration. Without wishing to be bound by theory, the goal is to test the role of novel KLF15 agonists in preclinical models that consists of human podocytes, human kidney organoids, and proteinuric murine models.

Generation of human kidney organoids. The generation and validation of human organoids has been performed in partnership with StemCell Technologies (LOS), using their protocol. To demonstrate feasibility, cultured human kidney organoids and scRNA-seq were imaged to demonstrate the presence of podocyte population. Specifically, immunostaining of human kidney organoids for podocytes (WT1, PODXL), Prox. Tub (LTL), Distal Tub. (ECAD), and Nuclei (DAPI) was performed, and a UMAP plot of scRNA-seq was generated. A feature plot of NHPS1, NHPS2 enriched in cluster 8 (podocyte) was also prepared (data not shown).

scRNA-seq. Processing of single cells from human organoids will be conducted through 10× Genomics instrumentation and subsequent analysis will be performed as previously demonstrated (data not shown). Procedures will be performed using the 10× Genomics software and pipelines previously described (55). In an attempt to improve the cell type classification model, various imputation algorithms developed for scRNA-seq (56) were tested and the single cells visualized using Principal Component Analysis (PCA), DDRTree (57), and Uniform Manifold Approximation and Projection (UMAP) (57). Finally, to analyze the collective functions of the genes in each cluster, enrichment analysis will be performed with Enrichr (58, 59) against the gene-set libraries from KEGG pathways (60), WikiPathways (42), and Gene Ontology (GO) Biological Processes (61).

PAN treatment (in vitro setting). Dosing and duration of treatment with puromycin treatment will be conducted as recently reported (16).

LPS model (short-term study). Baseline urine was collected in mice at 10 weeks of age. All mice will be administered low dose LPS (10 µg/g) intraperitoneally at 0 and 24 hours as previously described (8, 62). At the 12-hour time point following the initial LPS injection, mice were administered either vehicle or KLF15 agonist (5 mg/kg, q12 hr, IP). An additional dose of KLF15 agonist or vehicle injection will be administered at the 36-hour time point. Urine was collected at 24-hour increments with 1 ml of normal saline boluses (IP). Mice will be euthanized at 48 hours. Rationale for dosing is supported by preliminary data in FIG. 5D and as reported with LPS and DEX protocol (9).

Figures 18A, 18B:
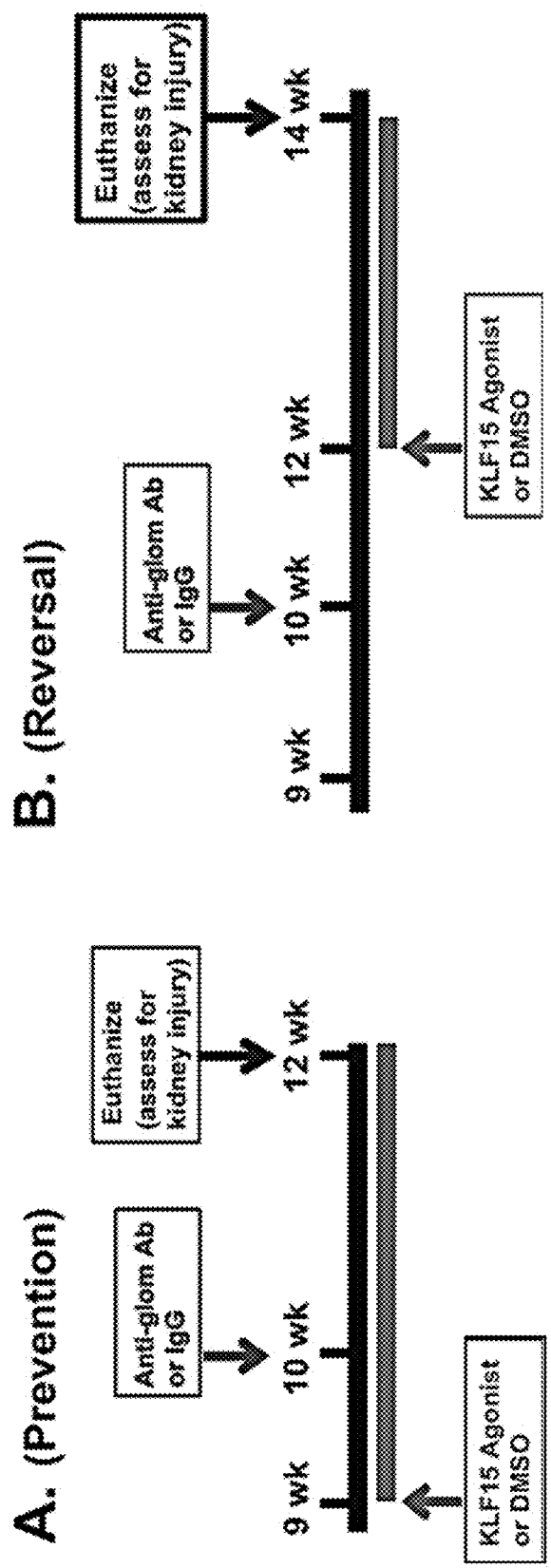
FIG. 18A and FIG. 18B show representative schema of prevention (FIG. 18A) and reversal (FIG. 18B) experimental model with anti-glom. Ab model. Timeline not to scale.

Anti-glomerular antibody (anti-glom Ab) murine model (mid-term study). Mice will be administered KLF15 agonist or vehicle (5 mg/kg, q12 hr, IP) at 9 weeks of age. Subsequently, all mice will be injected with anti-glom Ab or IgG (control) at week 10. Finally, at 12 weeks of age (2 weeks after anti-glom Ab treatment), all mice will be euthanized to assess whether KLF15 agonist prevents kidney injury (assessment for markers of injury is provided below) (FIG. 18A). Next, using a new set of mice, at 10 weeks of age, mice will be treated with anti-glom Ab or IgG (control) and at week 12 (i.e., 2 weeks post anti-glom Ab treatment), KLF15 agonist or vehicle will be administered. All mice will be euthanized at 14 weeks of age to determine whether KLF15 agonist reverses kidney injury observed in the anti-glom Ab-treated mice (FIG. 18B).

Anti-glom Ab dosing. Protocol for administration of sheep anti-glom Ab was based on the previously described methods (9, 63, 64). Briefly, mice will be administered sheep anti-glom Ab (5 mg per 20 g BW, IP) for 2 consecutive days. Rationale for duration of treatment is based on the observed course of injury as previously reported (9).

Figure 19A:
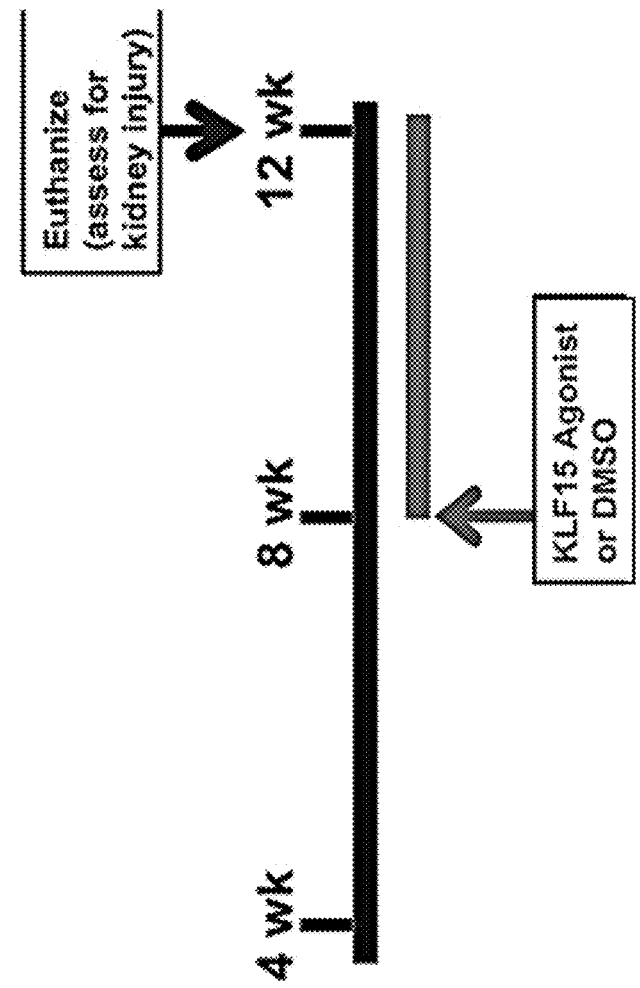
FIG. 19A and FIG. 19B show representative schema of prevention (FIG. 19A) and reversal (FIG. 19B) in the Tg26 model. Timeline not to scale.
Figure 19B:
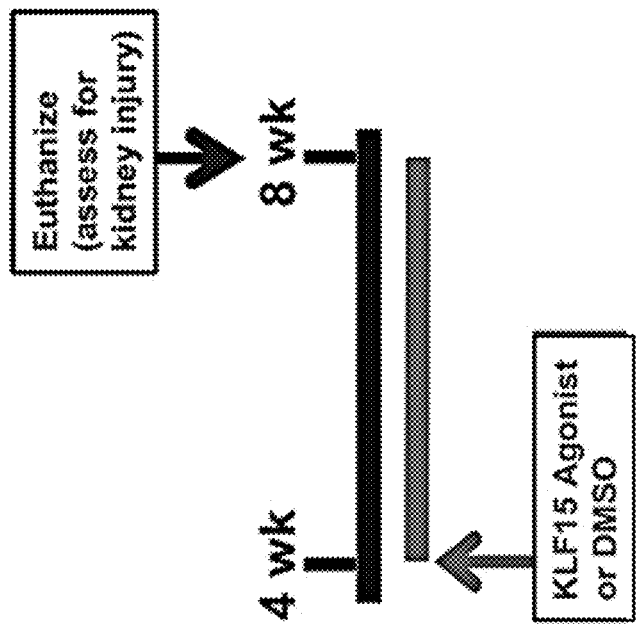

Collapsing FSGS murine model (long-term study). To test the hypothesis that KLF15 agonist prevents and reverses collapsing FSGS, Tg26 mice were utilized. Tg26 mice develop significant podocyte injury, extensive proteinuria, and collapsing FSGS starting at 4-6 weeks of age (65). Mice will be administered KLF15 agonist or vehicle (dosing regimen as above) at 4 weeks of age (approximately at weaning). Urine will be collected to assess for improvement in albuminuria weekly. Finally, at 8 weeks of age (4 weeks after initiation of treatment), all mice will be euthanized to assess whether KLF15 agonist prevents kidney injury (assessment for markers of injury is provided below) typically observed in the Tg26 mice (FIG. 19A). Next, using a new set of mice, at 8 weeks of age, KLF15 agonist or vehicle will be administered. All mice will be euthanized at 12 weeks of age to determine whether KLF15 agonist reverses kidney injury in Tg26 mice (FIG. 19B). Rationale for duration of treatment is based on the observed course of injury as reported (10).

Evaluation of markers of kidney injury. RT-PCR, western, and immunofluorescence (IF) will be used for podocyte differentiation markers (Nephrin, Synaptopodin, WT1, Podocin, p57). Albuminuria, glomerular isolation, RT-PCR, western blot, IHC, and EM will be performed as reported (66). Histomorphometric interpretation and scoring of kidney injury (FSGS, tubulointerstitial inflammation and fibrosis, CD68, Gr-1, αSMA, and Col1α1 staining) with evaluation of ultrastructural changes through EM will be conducted in a blinded fashion. Renal function will also be determined in all models by measuring serum urea nitrogen, creatinine, and transdermal measurement of GFR using FITC-sinistrin (MediBeacon) available at the Northport VAMC as previously reported (10, 67).

Alternative strategies and future directions. (1) It is recognized that intermittent IP dosing might require further optimization in these murine models; however the short-term LPS study does provide the rationale for this initial dosing regimen (FIG. 5D). Nonetheless, as an alternate strategy, it is proposed to utilize subcutaneous infusion via osmotic minipumps in the short-term LPS model initially to determine if continuous infusion is more efficacious than intermittent dosing. Furthermore, future studies will focus on testing the role of KLF15 agonists orally by gavage or in drinking water (if KLF15 analogues exhibit similar water solubility to lead K-7). Studies related to solubility and GI absorption will help optimize the route of administration and dosing frequency. (2) Since every in vitro model has advantages and disadvantages, two models are proposed (human podocytes and human kidney organoids). The immortalized podocytes model has the advantage of consistency and reliability but has the disadvantage that conditions and podocyte markers do not recapitulate the in vivo conditions. On the other hand, the human kidney organoid model has the advantage of recapitulating the tissue organization in the kidney (more representative than cell culture) as well as serving as a platform to test the effects of KLF15 agonists. However, there are disadvantages as it relates to degree of variability in organoid differentiation and mature cell types, which is mitigated, in part, by using standardized protocol and reagents provided by StemCell Technologies Inc. (LOS). By using a combination of both models, the rigor of the experimental studies is significantly improved and the efficacy of the analogues validated prior to advancing to expensive in vivo models (go/no-go strategy).

b. Determine the Role of Lead Klf15 Agonists in Minimizing the Cumulative GC Dose Necessary for its Therapeutic Effects in these Preclinical Models.

Figure 20C:
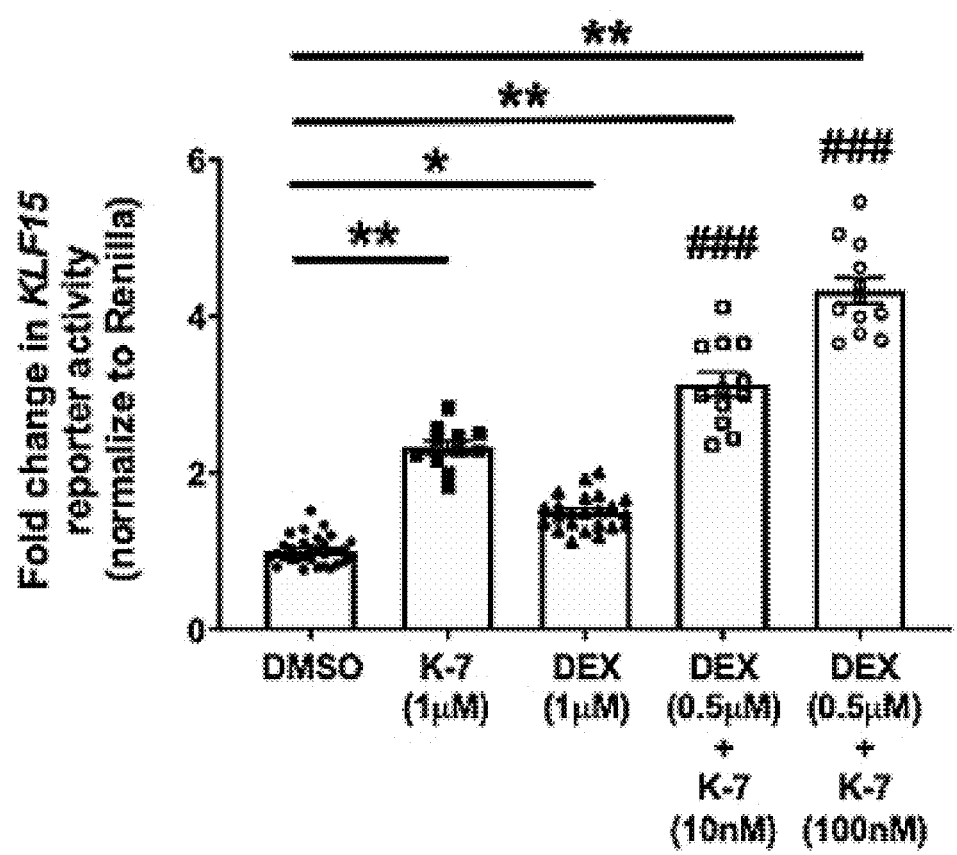

Rationale, approach, and strategy. Due to the systemic toxicity associated with GCs in primary glomerulopathies, identification of novel targets downstream of GC signaling that exhibit similar efficacy with lower toxicity will have a major impact in the field. As such, it was recently reported that the salutary effects of GCs in the podocytes are mediated through KLF15 using two preclinical murine models for proteinuric diseases (anti-glom Ab and LPS models) (9). In addition, it was observed that the podocyte-specific expression of KLF15 by immunostaining was associated with responsiveness to GCs in kidney biopsies with MCD and FSGS (9). Preliminary data also demonstrates that K-7 and lead analogues exhibit improved $EC_{50}$ and maximum effective dose as compared to DEX (FIG. 10A-C). Furthermore, it was observed that K-7 reduced the DEX dose required to induce KLF15 reporter activity, suggesting the synergistic benefits with combination therapy (FIG. 20A-C). Collectively, these data provide the rationale to test the effects of novel KLF15 agonists (K-7, BT502, BT503, BT514, and BT412) in minimizing the cumulative GC dose necessary for its therapeutic effects in these preclinical models.

To test this hypothesis, it is proposed to compare the in vivo efficacy (markers of kidney injury as described herein) of combination reduced dosing with DEX and KLF15 agonists as compared to DEX or KLF15 agonists alone in two preclinical proteinuric murine models (LPS, anti-glom. Ab). It was previously demonstrated that DEX treatment (2 mg/kg, IP, every 48 hr dosing) attenuated podocyte injury and kidney disease in LPS and anti-glomerular Ab treated mice (9), thereby providing the feasibility and rationale for the dosing regimen for these studies. Without wishing to be bound by theory, the goal is to test the hypothesis that a combination of KLF15 agonists and GCs will maintain efficacy while lowering the cumulative GC dose in these preclinical murine models.

LPS model. This model will be conducted as described herein, with addition of (KLF15 agonist (5 mg/kg, q12 hr, IP)+Reduced DEX dose (0.5 mg/kg, q12 hr, IP)), DEX alone (1 mg/kg, q12 hr, IP), and KLF15 agonist alone (5 mg/kg, q12 hr, IP) groups.

Figures 21A, 21B:
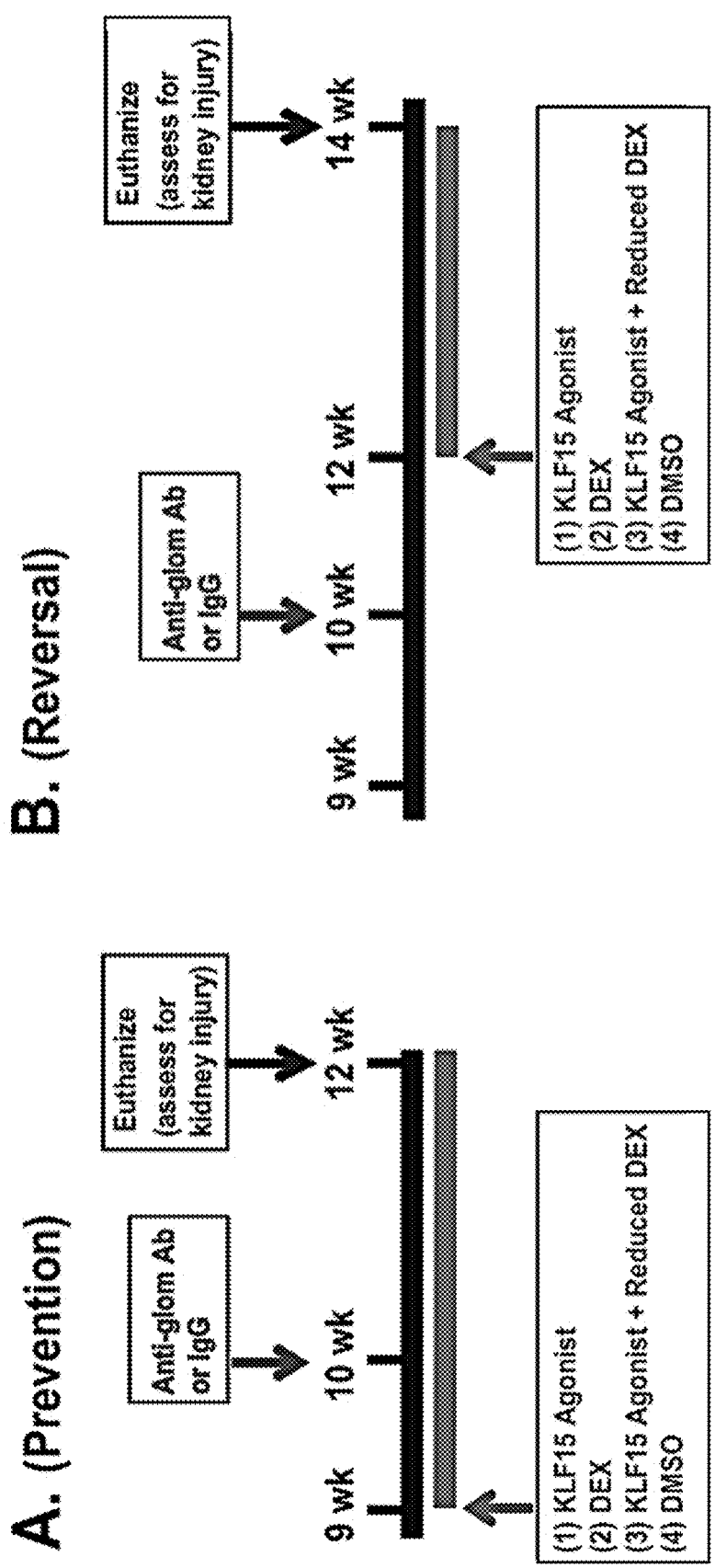
FIG. 21A and FIG. 21B show representative schema illustrating the prevention (FIG. 21A) and reversal (FIG. 21B) experimental model with anti-glom. Ab model using the combination treatment (Reduced DEX+KLF15 agonist). Timeline not to scale.

Anti-glomerular Ab model. This model will be conducted as described herein, with addition of combination (KLF15 agonist (5 mg/kg, q12 hr, IP)+Reduced DEX dose (1 mg/kg, q48 hr, IP)), DEX alone (2 mg/kg, q48 hr, IP), and KLF15 agonist alone (5 mg/kg, q12 hr, IP) treatment groups (FIG. 21A and FIG. 21B). Timing of initiating DEX treatment was based on previously described methodology (64). The dose and frequency of DEX dosing was extrapolated from patients receiving alternate day GC regimen for the treatment of primary glomerular disease (68) and tested previously (9).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

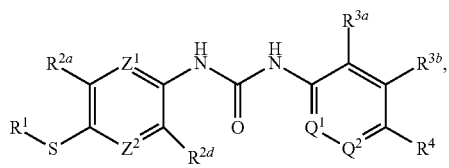

wherein each of $Q^1$ and $Q^2$, when present, is independently selected from N and $CR^{10}$;
wherein $R^{10}$, when present, is selected from hydrogen and halogen;
wherein $Z^1$ is selected from N and $CR^{2b}$;
wherein $Z^2$ is selected from N and $CR^{2c}$;
wherein $R^1$ is C1-C4 alkyl;
wherein each of $R^{2a}$, $R^{2b}$, $R^{2c}$, $R^{2d}$, $R^{3a}$, and $R^{3b}$, when present, is independently selected from hydrogen and halogen;
wherein $R^4$ is selected from halogen, —CN, —OH, C1-C4 alkyl, C1-C4 alkoxy, —B($R^{12}$)$_3$, and a structure:

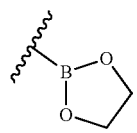 [SMILES: *B1OCCO1]

substituted with 0, 1, 2, 3, or 4 C1-C4 alkyl groups;
wherein each occurrence of $R^{12}$, when present, is independently halogen,
provided that when the compound has a structure represented by a formula:

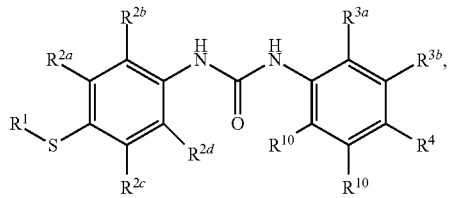

then $R^4$ is a structure:

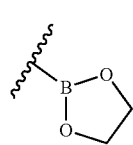 [SMILES: *B1OCCO1]

substituted with 0, 1, 2, 3, or 4 C1-C4 alkyl groups, and
provided that when the compound has a structure represented by a formula:

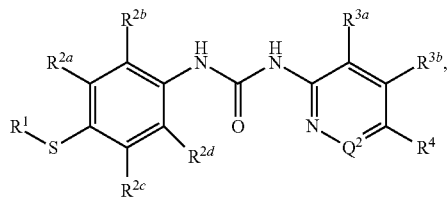

then $R^4$ is not halogen,
or a pharmaceutically acceptable salt thereof.

2. The compound of claim 1, wherein $R^4$ is selected from halogen, —CN, —OH, C1-C4 alkyl, C1-C4 alkoxy, and a structure:

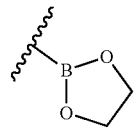 [SMILES: *B1OCCO1]

substituted with 0, 1, 2, 3, or 4 C1-C4 alkyl groups.

3. The compound of claim 1, wherein $R^1$ is methyl.

4. The compound of claim 1, wherein each of $R^{2a}$, $R^{2b}$, $R^{2c}$, $R^{2d}$, $R^{3a}$, and $R^{3b}$ is hydrogen.

5. The compound of claim 1, wherein the compound has a structure represented by a formula:

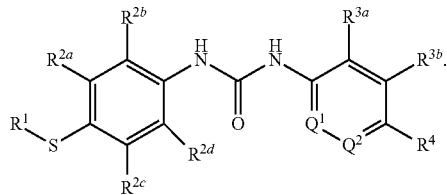

6. The compound of claim 5, wherein one of $Q^1$ and $Q^2$ is CH and one of $Q^1$ and $Q^2$ is N.

7. The compound of claim 5, wherein the compound has a structure represented by a formula:

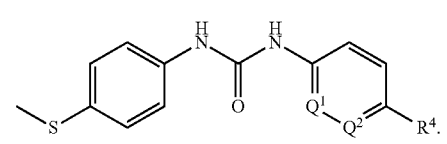

8. The compound of claim 5, wherein the compound is selected from:

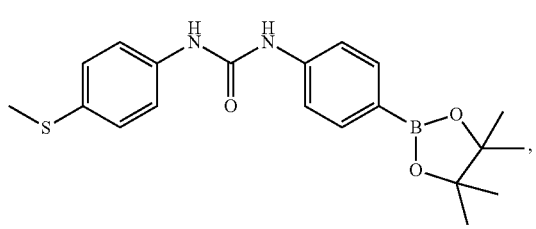

-continued
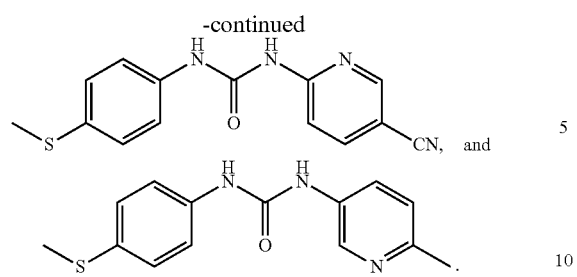
9. A pharmaceutical composition comprising an effective amount of the compound of claim 1, and a pharmaceutically acceptable carrier.
* * * * *